(12) United States Patent
Nowroozi et al.

(10) Patent No.: US 11,660,012 B2
(45) Date of Patent: May 30, 2023

(54) ASSESSMENT OF WOUND STATUS AND TISSUE VIABILITY VIA ANALYSIS OF SPATIALLY RESOLVED THZ REFLECTOMETRY MAPS

(71) Applicant: The Regents of the University of California, Oakland, CA (US)

(72) Inventors: Bryan Nowroozi, Oakland, CA (US); Warren S. Grundfest, Los Angeles, CA (US); Zachary Taylor, Oakland, CA (US); James Garritano, Los Angeles, CA (US); Priyamvada Tewari, Oakland, CA (US); Shijun Sung, Elk Grove, CA (US); Neha Bajwa, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 353 days.

(21) Appl. No.: 16/093,930

(22) PCT Filed: Apr. 17, 2017

(86) PCT No.: PCT/US2017/028003
§ 371 (c)(1),
(2) Date: Oct. 15, 2018

(87) PCT Pub. No.: WO2017/181200
PCT Pub. Date: Oct. 19, 2017

(65) Prior Publication Data
US 2019/0082998 A1 Mar. 21, 2019

Related U.S. Application Data

(60) Provisional application No. 62/323,449, filed on Apr. 15, 2016.

(51) Int. Cl.
*A61B 5/0507* (2021.01)
*A61B 5/00* (2006.01)
(Continued)

(52) U.S. Cl.
CPC .............. *A61B 5/0507* (2013.01); *A61B 5/00* (2013.01); *A61B 5/0035* (2013.01);
(Continued)

(58) Field of Classification Search
CPC ..... A61B 5/0507; A61B 5/0077; A61B 5/445; A61B 5/00; A61B 5/0035; A61B 5/05;
(Continued)

(56) References Cited

U.S. PATENT DOCUMENTS

| 4,021,031 A | 5/1977 | Meihofer et al. |
| 5,317,389 A | 5/1994 | Hochberg et al. |

(Continued)

FOREIGN PATENT DOCUMENTS

| EP | 3265863 A1 | 1/2018 |
| EP | 3442398 A1 | 2/2019 |

(Continued)

OTHER PUBLICATIONS

Tewari et al.; In vivo terahertz imaging of rat skin burns; published on Apr. 6, 2012; Journal of Biomendical Optics, 17(4), 040503 (2012) (Year: 2012).*

(Continued)

*Primary Examiner* — Chao Sheng
(74) *Attorney, Agent, or Firm* — KPPB LLP

(57) ABSTRACT

Systems, methods and apparatuses for performing wound analysis using THz imaging are provided. Due to the large complex component of water's dielectric constant in the THz regime, and the relative frequency invariance of non-aqueous tissue constituents, this modality is highly sensitive to the water content of tissue. It has been found that using THz imaging turns the presence of edema into a contrast mechanism, and allows for the use of the spatial distributions of edema to assess wound status immediately. Apparatus and methods enable earlier diagnosis of wound status (Continued)

which could result in accelerated treatment and shorter overall hospital stays.

32 Claims, 39 Drawing Sheets

(51) Int. Cl.
*A61B 5/05* (2021.01)
*G01B 11/24* (2006.01)
*A61B 5/055* (2006.01)

(52) U.S. Cl.
CPC .............. *A61B 5/0077* (2013.01); *A61B 5/05* (2013.01); *A61B 5/445* (2013.01); *A61B 5/0002* (2013.01); *A61B 5/0066* (2013.01); *A61B 5/0075* (2013.01); *A61B 5/055* (2013.01); *A61B 5/4878* (2013.01); *G01B 11/24* (2013.01)

(58) Field of Classification Search
CPC ..... A61B 5/0002; A61B 5/0066; A61B 5/055; A61B 5/4878; G01B 11/24
See application file for complete search history.

(56) References Cited

U.S. PATENT DOCUMENTS

| | | | |
|---|---|---|---|
| 9,295,402 B1* | 3/2016 | Arbab | G01N 21/3586 |
| 10,517,477 B2 | 12/2019 | Grundfest et al. | |
| 2001/0000978 A1 | 5/2001 | Hitzenberger et al. | |
| 2003/0130579 A1 | 7/2003 | McClane et al. | |
| 2006/0036181 A1 | 2/2006 | Treado et al. | |
| 2007/0114419 A1* | 5/2007 | Bastiaans | G01N 21/3563 250/341.8 |
| 2009/0048510 A1* | 2/2009 | Miller | G02B 21/367 600/426 |
| 2010/0195048 A1 | 8/2010 | Hammer et al. | |
| 2011/0005932 A1 | 1/2011 | Jovanovich et al. | |
| 2012/0198912 A1 | 8/2012 | Ewing et al. | |
| 2013/0070234 A1 | 3/2013 | Li et al. | |
| 2013/0162949 A1 | 6/2013 | Culjat et al. | |
| 2013/0190594 A1 | 7/2013 | Oraevsky et al. | |
| 2014/0103215 A1 | 4/2014 | Rahman et al. | |
| 2015/0090881 A1* | 4/2015 | King | G01N 21/3586 250/339.11 |
| 2015/0164327 A1 | 6/2015 | Yaroslavsky et al. | |
| 2015/0316511 A1 | 11/2015 | Guo | |
| 2017/0079530 A1* | 3/2017 | DiMaio | G06T 7/0012 |
| 2018/0020913 A1 | 1/2018 | Grundfest et al. | |
| 2018/0303347 A1 | 10/2018 | Grundfest et al. | |
| 2019/0117109 A1 | 4/2019 | Grundfest | |

FOREIGN PATENT DOCUMENTS

| | | |
|---|---|---|
| HK | 1248826 A | 10/2018 |
| WO | 8902718 A1 | 4/1989 |
| WO | 0078217 A1 | 12/2000 |
| WO | 2003023383 A2 | 3/2003 |
| WO | 2012083206 A1 | 6/2012 |
| WO | 2015195975 A1 | 12/2015 |
| WO | 2016131047 A1 | 8/2016 |
| WO | 2017181200 A1 | 10/2017 |
| WO | 2017181201 A1 | 10/2017 |

OTHER PUBLICATIONS

Federici, "Review of Moisture and Liquid Detection and Mapping using Terahertz Imaging", Journal of Infrared, Millimeter, and Terahertz Waves Feb. 1, 2012 (Feb. 1, 2012), vol. 33, pp. 97-126.
Ferguson et al., "Materials for terahertz science and technology", Nature Materials, vol. 1, No. 1, Sep. 1, 2002, pp. 26-33.
Fisher et al., "Assessment of Transient Changes in Corneal Hydration Using Confocal Raman Spectroscopy", Cornea, vol. 22, No. 4, May 2003, pp. 363-370.
Fitzgerald et al., "Terahertz Pulsed Imaging of Human Breast Tumors", Radiology, vol. 239, No. 2, May 2006, Electronic Publication: Mar. 16, 2006, pp. 533-540.
Frankel et al., "High-Voltage Picosecond Photoconductor Switch Based on Low-Temperature-Grown GaAs", IEEE Transactions on Electron Devices, vol. 37, No. 12, Dec. 1990, pp. 2493-2498.
Glass et al., "A Viscoelastic Biomechanical Model of the Cornea Describing the Effect of Viscosity and Elasticity on Hysteresis", Investigative Ophthalmology & Visual Science, vol. 49, No. 9, Sep. 2008, pp. 3919-3926.
Gromacki et al., "Central and Peripheral Corneal Thickness in Keratoconus and Normal Patient Groups", Optometry and Vision Science, vol. 71, No. 7, Jul. 1994, pp. 437-441.
Hinton et al., "A Fast Learning Algorithm for Deep Belief Nets", Neural Computation, vol. 18, 2006, pp. 1527-1554.
Hitzenberger et al., "Measurement of Corneal Thickness by Loser Doppler Interferometry", Investigative Ophthalmology & Visual Science, vol. 33, No. 1, Jan. 1992, pp. 98-103.
Hoshina et al., "Terahertz pulsed imaging of frozen biological tissues", Applied Physics Letters, vol. 94, No. 12, Mar. 23, 2009, 3 pgs.
Hu et al., "Terahertz radiation induced by subband-gap femtosecond optical excitation of GaAs", Physical Review Letters, vol. 67, No. 19, Nov. 4, 1991, 2709.
Huang et al., "Optical Coherence Tomography", Science, vol. 254, No. 5035, Nov. 22, 1991, pp. 1178-1181.
Izatt et al., "Micrometer-Scale Resolution Imaging of the Anterior Eye In Vivo With Optical Coherence Tomography", Archives of Ophthalmology, vol. 112, No. 12, Dec. 1994, pp. 1584-1589.
Jaskille et al., "Critical Review of Burn Depth Assessment Techniques: Part I. Historical Review", Journal of Burn Care & Research, vol. 30, No. 6, Nov. 1, 2009, pp. 937-947.
Jaskille et al., "Critical Review of Burn Depth Assessment Techniques: Part II. Review of Laser Doppler Technology", Journal of Burn Care & Research, vol. 31, No. 1, Jan. 1, 2010, pp. 151-157.
Johnson et al., "Novel Corneal Hydration Imaging Technology Using Terahertz Illumination", Investigative Ophthalmology & Visual Science, Association for Research in Vision and Ophthalmology (ARVO) Annual Meeting Abstract, vol. 52, No. 14, Apr. 2011, pp. 4092.
Karkkainen et al., "Effective Permittivity of Mixtures: Numerical Validation by the FDTD Method", IEEE Transactions on Geoscience and Remote Sensing, vol. 38, No. 3, May 2000, pp. 1303-1308.
Ketchen et al., "Generation of subpicosecond electrical pulses on coplanar transmission lines", Applied Physics Letters, vol. 48, No. 12, 1986, pp. 751-753.
King-Smith et al., "Tear Film Interferometry and Corneal Surface Roughness", Investigative Ophthalmology & Visual Science, vol. 55, No. 4, Apr. 2014, pp. 2614-2618.
King-Smith et al., "The Thickness of the Human Precorneal Tear Film: Evidence from Reflection Spectra", Investigative Ophthalmology & Visual Science, vol. 41, No. 11, Oct. 2000, pp. 3348-3359.
Klintworth, "Corneal dystrophies", Orphanet Journal of Rare Diseases, vol. 4, No. 7, Feb. 23, 2009, 38 pgs.
Knabl et al., "Controlled partial skin thickness burns: an animal model for studies of burnwound progression", Burns, vol. 25, No. 3, May 1999, pp. 229-235.
Lackner et al., "Repeatability and Reproducibility of Central Corneal Thickness Measurement With Pentacam, Orbscan, and Ultrasound", Optometry and Vision Science, vol. 82, No. 10, Oct. 2005, pp. 892-899.
Lamb, "Miscellaneous data on materials for millimetre and submillimetre optics", International Journal of Infrared and Millimeter Waves, vol. 17, No. 12, Dec. 1996, pp. 1997-2034.
Li et al., "Differences in Healing of Skin Wounds Caused by Burn and Freeze Injuries", Annals of Surgery, vol. 191, No. 2, Feb. 1980, pp. 244-248.

(56) References Cited

OTHER PUBLICATIONS

Liebe et al., "A Model for the Complex Permittivity of Water at Frequencies Below 1 THz", International Journal of Infrared and Millimeter Waves, vol. 12, No. 7, Jul. 1991, pp. 659-675.
Liu et al., "Evaluation of corneal thickness and topography in normal eyes using the Orbscan corneal topography system", British Journal of Ophthalmology, vol. 83, No. 7, Jul. 1, 1999, pp. 774-778.
Maccabi et al., "Reflectivity measurements of water and dioxane mixtures using a 100 GHz Gunn diode source", Proceedings of SPIE BiOS Terahertz and Ultrashort Electromagnetic Pulses for Biomedical Applications, San Francisco, California, vol. 8585, 2013, 7 pgs.
Malik et al., "Corneal confocal microscopy: a non-invasive surrogate of nerve fibre damage and repair in diabetic patients", Diabetologia, vol. 46, No. 5, May 2003, pp. 683-688.
Mandell et al., "Corneal Hydration Control in Fuchs' Dystrophy", Investigative Ophthalmology & Visual Science, vol. 30, No. 5, May 1989, pp. 845-852.
Manson et al., "The Role of Oxygen-free Radicals in Ischemic Tissue Injury in Island Skin Flaps", Annals of Surgery, vol. 198, No. 1, Jul. 1983, pp. 87-90.
Martin, "Wound Healing—Aiming for Perfect Skin Regeneration", Science, vol. 276, No. 5309, Apr. 4, 1997, pp. 75-81.
McCrackin et al., "Measurement of the Thickness and Refractive Index of Very Thin Films and the Optical Properties of Surfaces by Ellipsometry", Journal of Research of the National Bureau of Standards—A. Physics and Chemistry, vol. 67A, No. 4, Jul.-Aug. 1963, pp. 363-377.
McDonnell et al., "Corneal Thickness Changes After High-Risk Penetrating Keratoplasty", Archives of Ophthalmology, vol. 111, No. 10, Oct. 1993, pp. 1374-1381.
Meissner et al., "The Complex Dielectric Constant of Pure and Sea Water From Microwave Satellite Observations", IEEE Transactions on Geoscience and Remote Sensing, vol. 42, No. 9, Sep. 2004, pp. 1836-1849.
Meyer et al., "A standard burn model using rats", Acta Cirurgica Brasileira, vol. 14, No. 4, Oct./Dec. 1999, 8 pgs.
Ney et al., "Modeling of reflectometric and ellipsometric spectra from the skin in the terahertz and submillimeter waves region", Journal of Biomedical Optics, vol. 16, No. 6, Jun. 2011, pp. 067006-1-067006-15.
Niklasson et al., "Effective medium models for the optical properties of inhomogeneous materials", Applied Optics, vol. 20, No. 1, Jan. 1981, pp. 26-30.
Orfanidis, Sophocles J., "Electromagnetic Waves and Antennas", Rutgers University, Jun. 1, 2014, retrieved from http://www.ece.rutgers.edu/~orfanidi/ewa/, 610 pages (Presented in three parts).
Panda et al., "Corneal Graft Rejection", Survey of Ophthalmology, vol. 52, Issue 4, Jul.-Aug. 2007, pp. 375-396.
Park et al., "In vivo burn depth determination by high-speed fiber-based polarization sensitive optical coherence tomography", Journal of Biomedical Optics, vol. 6, No. 4, Oct. 2001, pp. 474-479.
Pavlin et al., "Clinical Use of Ultrasound Biomicroscopy", Ophthalmology, vol. 98, No. 3, Mar. 1991, pp. 287-295.
Pavlin et al., "Subsurface Ultrasound Microscopic Imaging of the Intact Eye", Ophthalmology, vol. 97, No. 2, Feb. 1990, pp. 244-250.
Payette et al., "Assessment of Skin Flaps Using Optically Based Methods for Measuring Blood Flow and Oxygenation", Plastic and Reconstructive Surgery, vol. 115, No. 2, Feb. 2005, pp. 539-546.
Pfeffer et al., "Myocardial Infarct Size and Ventricular Function in Rats", Circulation Research, vol. 44, No. 4, Apr. 1979, pp. 503-512.
Pickwell et al., "In vivo study of human skin using pulsed terahertz radiation", Physics in Medicine & Biology, vol. 49, No. 9, Apr. 2004, pp. 1595-1607.
Pickwell et al., "Simulation of terahertz pulse propagation in biological systems", Applied Physics Letters, vol. 84, No. 12, Mar. 22, 2004, pp. 2190-2192.
Pierce et al., "Collagen denaturation can be quantified in burned human skin using polarization-sensitive optical coherence tomography", Burns, vol. 30, No. 6, Sep. 2004, pp. 511-517.

Riazuddin et al., "Missense Mutations in TCF8 Cause Late-Onset Fuchs Corneal Dystrophy and Interact with FCD4 on Chromosome 9p", The American Journal of Human Genetics, vol. 86, No. 1, Dec. 31, 2009, pp. 45-53.
Richard et al., "Characterization of the Skin In Vivo by High Resolution Magnetic Resonance Imaging: Water Behavior and Age-Related Effects", Journal of Investigative Dermatology, vol. 100, No. 5, May 1993, pp. 705-709.
Richard et al., "In Vivo Proton Relaxation Times Analysis of the Skin Layers by Magnetic Resonance Imaging", Journal of Investigative Dermatology, vol. 97, No. 1, Jul. 1991, pp. 120-125.
Rietschel, "A Method to Evaluate Skin Moisturizers in Vivo", Journal of Investigative Dermatology, vol. 70, No. 3, Mar. 1978, pp. 152-155.
Ruminski et al., "Thermal Parametric Imaging in the Evaluation of Skin Burn Depth", IEEE Transactions on Biomedical Engineering, vol. 54, No. 2, Feb. 2007, pp. 303-312.
Sajadi et al., "Terahertz-field-induced optical birefringence in common window and substrate materials", Optics Express, vol. 23, No. 22, Oct. 28, 2015, pp. 28985-28992.
Sharma, "Microimaging of hairless rat skin by magnetic resonance at 900 MHz", Magnetic Resonance Imaging, vol. 27, No. 2, Feb. 2009, pp. 240-255.
Extended European Search Report for European Application No. 16750060.2, Search completed Nov. 12, 2018, dated Nov. 22, 2018, 7 Pgs.
Extended European Search Report for European Application No. 17783377.9, Search completed Oct. 30, 2019, dated Nov. 11, 2019, 09 Pgs.
International Preliminary Report on Patentability for International Application PCT/US2017/028006, Report dated Oct. 16, 2018, dated Oct. 25, 2018, 10 Pgs.
International Preliminary Report on Patentability for International Application PCT/US2017/028003, Report dated Oct. 16, 2018, dated Oct. 25, 2016, 10 Pgs.
International Preliminary Report on Patentability for International Application PCT/US2015/036518, Report dated Dec. 20, 2016, dated Dec. 29, 2016, 7 Pgs.
International Preliminary Report on Patentability for International Application PCT/US2016/017998, Report dated Aug. 15, 2017, dated Aug. 24, 2017, 8 Pgs.
International Search Report and Written Opinion for International Application No. PCT/US2016/017998, Search completed May 26, 2016, dated May 26, 2016, 10 Pgs.
International Search Report and Written Opinion for International Application No. PCT/US2017/028003, Search completed Jun. 7, 2017, dated Jul. 17, 2017, 14 Pgs.
International Search Report and Written Opinion for International Application No. PCT/US2017/028006, Search completed Jun. 7, 2017 dated Jul. 17, 2017, 14 Pgs.
International Search Report and Written Opinion for International Application PCT/US2015/036518, Report Completed Sep. 15, 2015, dated Sep. 15, 2015, 10 pgs.
"American National Standard for Safe Use of Lasers", American National Standards Institute, Inc., ANSI Z136.1, Mar. 16, 2007, 22 pgs.
"Gunn Oscillators", SpaceKLabs: MM-Wave Technology ISO 9001:2008 Certified, Retrieved from http://spaceklabs.com/cm/Products/Frequency_Sources/Gunn%20Oscillators.html on Sep. 12, 2015, 2 pgs.
"THz Detectors", gentec-eo, Retrieved from https://www.gentec-eo.com/products/thz-detectors on Nov. 28, 2012, 2 pgs.
Adamis et al., "Fuchs' endothelial dystrophy of the cornea", Survey of Ophthalmology, vol. 38, Issue 2, Sep.-Oct. 1993, pp. 149-168.
Alemdaroglu et al., "An investigation on burn wound healing in rats with chitosan gel formulation containing epidermal growth factor", Burns, vol. 32, No. 3, May 2006, pp. 319-327.
Arbab et al., "Terahertz reflectometry of burn wounds in a rat model", Biomedical Optics Express, vol. 2, No. 8, Jul. 21, 2011, pp. 2339-2347.
Arbab et al., "Terahertz spectroscopy for the assessment of burn injuries in vivo", Journal of Biomedical Optics, vol. 18, No. 7, Jul. 2013, pp. 077004-1-077004-7.

(56) References Cited

OTHER PUBLICATIONS

Azartash et al., "Pre-corneal tear film thickness in humans measured with a novel technique", Molecular Vision, vol. 17, Mar. 22, 2011, pp. 756-767.
Bajwa et al., "Reflective terahertz (THz) imaging: system calibration using hydration phantoms", Proceedings of SPIE Terahertz and Ultrashort Electromagnetic Pulses for Biomedical Applications, San Francisco, California, vol. 8585, 2013, 10 pgs.
Bajwa et al., "Reflective THz and MR imaging of burn wounds: a potential clinical validation of THz contrast mechanisms", Proceedings of SPIE Terahertz Emitters, Receivers, and Applications III, San Diego, California, vol. 8496, 2012, 7 pgs.
Bauer et al., "In Vivo Confocal Raman Spectroscopy of the Human Cornea", Cornea, vol. 18, No. 4, Jul. 1999, pp. 483-488.
Bauer et al., "Noninvasive Assessment of the Hydration Gradient across the Cornea Using Confocal Raman Spectroscopy", Investigative Ophthalmology & Visual Science, vol. 39, No. 5, Apr. 1998, pp. 831-835.
Bechmann et al., "Central Corneal Thickness Measurement with a Retinal Optical Coherence Tomography Device Versus Standard Ultrasonic Pachymetry", Cornea, vol. 20, No. 1, Jan. 2001, pp. 50-54.
Bennett et al., "Assessment of corneal hydration sensing in the terahertz band: in vivo results at 100 GHz", Journal of Biomedical Optics, vol. 17, No. 9, Sep. 2012, pp. 097008.1-097008.7.
Bennett et al., "Stratified Media Model for Terahertz Reflectometry of the Skin", IEEE Sensors Journal, vol. 11, No. 5, May 2011, pp. 1253-1262.
Bennett et al., "Terahertz Sensing in Corneal Tissues", Journal of Biomedical Optics, vol. 16, No. 5, May 2011, pp. 057003.1-057003.8.
Bennett et al., "Terahertz time-lapse imaging of hydration in physiological tissues", Proc. SPIE 7938, Terahertz Technology and Applications IV, Article 793808, Feb. 24, 2011, 9 pages; doi: 10.1117/12.882962.
Bittoun et al., "Advances in MR imaging of the skin", NMR in Biomedicine, vol. 19, No. 7, Oct. 31, 2006, pp. 723-730.
Borderie et al., "Outcome of Graft Central Thickness After Penetrating Keratoplasty", Ophthalmology, vol. 112, No. 4, Apr. 2005, pp. 626-633.
Brugin et al., "Central Corneal Thickness: Z-Ring Corneal Confocal Microscopy Versus Ultrasound Pachymetry", Cornea, vol. 26, No. 3, Apr. 2007, pp. 303-307.
Chakrabarti et al., "Comparison of corneal thickness measurements using ultrasound and Orbscan slit-scanning topography in normal and post-LASIK eyes", Journal of Cataract & Refractive Surgery, vol. 27, No. 11, Nov. 2001, pp. 1823-1828.
Cheung et al., "Excitation of Coherent Phonon Polaritons with Femtosecond Optical Pulses", Physical Review Letters, vol. 55, No. 20, Nov. 11, 1985, 4 pgs.
Crane et al., "Raman spectroscopic evidence for octacalcium phosphate and other transient mineral species deposited during intramembranous mineralization", Bone, 2006, vol. 39, pp. 434-442.
Cutting et al., "Wound infection, dressings and pain, is there a relationship in the chronic wound?", International Wound Journal, vol. 10, No. 1, Feb. 2013, Electronic Publication: May 28, 2012, 10 pgs.
De Souza et al., "Influence of Temperature and Humidity on Laser in situ Keratomileusis Outcomes", Journal of Refractive Surgery, vol. 17, No. 2, Mar.-Apr. 2001, pp. S202-S204.
Devgan et al., "Modalities for the Assessment of Burn Wound Depth", Journal of Burns and Wounds, vol. 5, Feb. 15, 2006, pp. 7-15.
Di Sieno et al., "Time-domain diffuse optical tomography using silicon photomultipliers: feasibility study", Journal of Biomedical Optics, vol. 21, No. 11, Nov. 2016, pp. 116002-1-116002-9.

Dong et al., "Measurement of central corneal thickness and pre-corneal tear film thickness of rabbits using the Scheimpflug system", International Journal of Ophthalmology, vol. 6, No. 5, Oct. 18, 2013, pp. 584-587.
Dougherty et al., "Excimer Laser Ablation Rate and Corneal Hydration", American Journal of Ophthalmology, vol. 118, No. 2, Aug. 1994, pp. 169-176.
Doughty et al., "Human Corneal Thickness and Its Impact on Intraocular Pressure Measures: A Review and Meta-analysis Approach", Survey of Ophthalmology, vol. 44, No. 5, Mar.-Apr. 2000, pp. 367-408.
Ehlers et al., "Central Thickness in Corneal Disorders", Acta Ophthalmologica, vol. 56, No. 3, Jun. 1978, pp. 412-416.
Epstein et al., "Cutaneous Wound Healing", New England Journal of Medicine, vol. 341, Sep. 2, 1999, pp. 738-746.
Evans et al., "Chemical imaging of tissue in vivo with video-rate coherent anti-Stokes Raman Scattering microscopy", PNAS, Nov. 15, 2005, vol. 102, No. 46, pp. 16807-16812.
Shijun et al., "Preliminary results 12-15 of non-contact THz imaging of cornea", Visual Communications and Image Processing, vol. 9362, Mar. 13, 2015, 6 pgs.
Singh et al., "Terahertz sensing of corneal hydration", Annual International Conference of the IEEE Engineering in Medicine and Biology, Buenos Aires, Argentina, Aug. 31-Sep. 4, 2010, 4 pgs.
Singh et al., "THz imaging of skin hydration: motivation for the frequency band", Proceedings of SPIE Advanced Biomedical and Clinical Diagnostic Systems VIII, San Francisco, California, vol. 7555, 2010, 8 pgs.
Srinivas et al., "Determination of burn depth by polarization-sensitive optical coherence tomography", Journal of Biomedical Optics, vol. 9, No. 1, Jan. 2004, pp. 207-212.
Sung, "Terahertz Imaging and Remote Sensing Design for Applications in Medical Imaging", A thesis submitted in partial satisfaction of the requirements for the degree Master of Science in Electrical Engineering of University of California, 2013. See pp. 1-50 and figures 1-4 to 4-1 (c).
Sung et al., "Fast-scanning THz medical imaging system for clinical application", Proceedings of SPIE Terahertz Emitters, Receivers, and Applications III, San Diego, California, 2012, 7 pgs.
Taylor, "Active THz Imaging for Medical Applications", Ph.D, Electrical and Computer Engineering, UC Santa Barbara, Santa Barbara, 2009, 201 pgs.
Taylor et al., "A Reflection Based, Pulsed THz Imaging System with 1 mm Spatial Resolution", IEEE/MTT-S International Microwave Symposium, Honolulu, Hawaii, Jun. 3-8, 2007, 4 pgs.
Taylor et al., "A scanned beam THz imaging system for medical applications", Proceedings of SPIE Terahertz Emitters, Receivers, and Applications II, San Diego, California, vol. 8119, 2011, 7 pgs.
Taylor et al., "Active THz medical imaging using broadband direct detection", Proceedings of SPIE Terahertz, RF, Millimeter, and Submillimeter-Wave Technology and Applications VI, San Francisco, California, vol. 8624, 2013, 10 pgs.
Taylor et al., "Analysis of Pulsed THz Imaging Using Optical Character Recognition", IEEE Sensors Journal, vol. 9, No. 1, Jan. 2009, pp. 3-8.
Taylor et al., "Pseudophakic Bullous Keratopathy", Ophthalmology, vol. 90, Issue 1, Jan. 1983, pp. 19-24.
Taylor et al., "THz and mm-Wave Sensing of Corneal Tissue Water Content: Electromagnetic Modeling and Analysis", IEEE Transactions on Terahertz Science and Technology, vol. 5, Issue 2, Mar. 2015, pp. 170-183.
Taylor et al., "THz and mm-Wave Sensing of Corneal Tissue Water Content: In Vivo Sensing and Imaging Results", HHS Public Access, Author Manuscript, Jul. 7, 2015, 38 pgs. Published as: IEEE Transactions on Terahertz Science and Technology, vol. 5, Issue 2, Mar. 2015, pp. 184-196.
Taylor et al., "THz imaging based on water-concentration contrast", Proceedings of SPIE Terahertz for Military and Security Applications VI, Orlando, Florida, vol. 6949, 2008, 8 pgs.
Taylor et al., "THz Medical Imaging", 6th ESA Workshop on Millimeter Wave Technology and Applications, 4th Global Symposium on Millimeter Waves, Helsinki, Finland, 2011, 6 pgs.

(56) References Cited

OTHER PUBLICATIONS

Taylor et al., "THz Medical Imaging: in vivo Hydration Sensing", IEEE Transactions on Terahertz Science and Technology, vol. 1, No. 1, Sep. 2011, pp. 201-219.
Tewari et al., "Advances in biomedical imaging using THz technology with applications to burn-wound assessment", Proceedings of SPIE Terahertz Technology and Applications V, San Francisco, California, vol. 8261, 2012, 8 pgs.
Tewari et al., "In vivo terahertz imaging of rat skin burns", Journal of Biomedical Optics, vol. 17, No. 4, Apr. 2012, pp. 040503-1-040503-3.
Tonouchi, "Cutting-edge terahertz technology", Nature Photonics, vol. 1, No. 2, Feb. 2007, pp. 97-105.
Ucakhan et al., "Corneal thickness measurements in normal and keratoconic eyes: Pentacam comprehensive eye scanner versus noncontact specular microscopy and ultrasound pachymetry", Journal of Cataract & Refractive Surgery, vol. 32, No. 6, Jun. 2006, pp. 970-977.
Ung et al., "High-refractive-index composite materials for terahertz waveguides: trade-off between index contrast and absorption loss", Journal of the Optical Society of America B, vol. 28, No. 4, Apr. 2011, pp. 917-921.
Wallace et al., "Terahertz Pulsed Spectroscopy of Human Basal Cell Carcinoma", Applied Spectroscopy, vol. 60, No. 10, Oct. 2006, pp. 1127-1133.
Whitcher et al., "Corneal blindness: a global perspective", Bulletin of the World Health Organization, Special Theme—Blindness, vol. 79, No. 3, 2001, pp. 214-221.
Woodward et al., "Terahertz pulse imaging in reflection geometry of human skin cancer and skin tissue", Physics in Medicine and Biology, vol. 47, Oct. 17, 2002, pp. 3853-3863.
Xu et al., "0.15-3.72 THz absorption of aqueous salts and saline solutions", Applied Physics Letters, vol. 90, No. 3, Jan. 18, 2007, 3 pgs.
Yeh et al., "Electromagnetic propagation in periodic stratified media. I. General theory", Journal of the Optical Society of America, vol. 67, No. 4, Apr. 1977, pp. 423-438.
Ytteborg et al., "Corneal Edema and Intraocular Pressure: II. Clinical Results", Archives of Ophthalmology, vol. 74, No. 4, Oct. 1965, pp. 477-484.
Yue et al., "Histochemical studies of keratoconus", Current Eye Research, vol. 7, No. 1, 1988, pp. 81-86.
Arbab et al., "Characterization of burn injuries using terahertz time-domain spectroscopy", Proceedings of the Advanced Biomedical and Clinical Diagnostic Systems IX, vol. 7890, Feb. 21, 2011, 7 pgs.
Bajwa et al., "In vivo Confirmation of Hydration Based Contrast Mechanisms for Terahertz Medical Imaging using MRI", Proceedings of SPIE Terahertz Emitters, Receivers, and Applications V, San Diego, California, vol. 9199, 2014, 8 pgs.
Bamashmus et al., "Reasons for Not Performing Keratorefractive Surgery in Patients Seeking Refractive Surgery in a Hospital-Based Cohort in "Yemen"", Middle East African Journal of Ophthalmology, vol. 17, No. 4, Oct. 13, 2010, pp. 349-353.
Bergkvist et al., "Assessment of microcirculation of the skin using Tissue Viability Imaging: A promising technique for detecting venous stasis in the skin", Microvascular Research, vol. 101, Sep. 2015, pp. 20-25.
Brown et al., "THz Imaging of Skin Tissue—Exploiting the Strong Reflectivity of Liquid Water", IEEE 35th International Conference on Infrared, Millimeter, and Terahertz Waves, Rome, Italy, Sep. 5-10, 2010, 2 pgs.
Chen et al., "Timing of Presentation of the First Signs of Vascular Compromise Dictates the Salvage Outcome of Free Flap Transfers", Plastic and Reconstructive Surgery, vol. 120, No. 1, Jul. 2007, pp. 187-195.
Demling, "The Burn Edema Process: Current Concepts", Journal of Burn Care & Research, vol. 26, No. 3, May 1, 2005, pp. 207-227.
Ehlers et al., "Corneal thickness: measurement and implications", Experimental Eye Research, vol. 78, No. 3, Mar. 2004, pp. 543-548.
Gambichler et al., "Applications of optical coherence tomography in dermatology", Journal of Dermatological Science, vol. 40, No. 2, Nov. 2005, pp. 85-94.
Hoeksema et al., "Accuracy of early burn depth assessment by laser Doppler imaging on different days post burn", Burns, vol. 35, No. 1, Feb. 2009, pp. 36-45.
Jeng et al., "Laser Doppler imaging determines need for excision and grafting in advance of clinical judgment: a prospective blinded trial", Burns, vol. 29, No. 7, Nov. 2003, pp. 665-670.
Li et al., "Corneal Pachymetry Mapping with High-speed Optical Coherence Tomography", Ophthalmology, vol. 113, No. 5, May 2006, pp. 792-799.e2.
Malone et al., "Design of a thermal imaging diagnostic using 90-degree off-axis parabolic mirrors", Proceedings of the SPIE Optics + Photonics, San Diego, California, vol. 6288, Sep. 2006, 9 pgs.
Mirrashed et al., "In vivo quantitative analysis of the effect of hydration (immersion and Vaseline treatment) in skin layers using high-resolution MRI and magnetisation transfer contrast", Skin Research and Technology, vol. 10, No. 1, Jan. 20, 2004, pp. 14-22.
Monstrey et al., "Assessment of burn depth and burn wound healing potential", Burns, vol. 34, No. 6, Sep. 2008, pp. 761-769.
Sung et al., "Reflective measurement of water concentration using millimeter wave illumination", Proceedings of SPIE Health Monitoring of Structural and Biological Systems, San Diego, California, Apr. 18, 2011, 6 pgs.
Taylor et al., "Reflective terahertz imaging of porcine skin burns", Optics Letters, vol. 33, No. 11, Jun. 1, 2008, pp. 1258-1260.
Tewari et al., "Terahertz Imaging of Biological Tissues", Studies in Health Technology and Informatics, vol. 163: Medicine Meets Virtual Reality 18, 2011, pp. 653-657.

\* cited by examiner $$R(t_m) = \frac{1}{\Delta x}\int_{\Delta x} R(t_m, x)dx$$

$$N(t_m, d_n) = \frac{1}{\Delta x}\int_{\Delta x} N(t_m, d_n, x)dx$$

ASSESSMENT OF WOUND STATUS AND TISSUE VIABILITY VIA ANALYSIS OF SPATIALLY RESOLVED THZ REFLECTOMETRY MAPS

CROSS REFERENCE TO RELATED APPLICATIONS

This application is a U.S. National Stage Application of PCT Application No. PCT/US2017/028003, entitled "Assessment of Wound Status and Tissue Viability Via Analysis of Spatially Resolved THz Reflectometry Maps" to Nowroozi et al., filed Apr. 17, 2017, which application claims priority to U.S. Provisional Application No. 62/323, 449, entitled "Assessment of Wound Status and Tissue Viability Via Analysis of Spatially Resolved THz Reflectometry Maps" to Taylor et al., filed Apr. 15, 2016, the disclosures of which are hereby incorporated by reference in their entireties.

STATEMENT OF FEDERAL FUNDING

This invention was made with Government support under EB016896, EB015084 awarded by the National Institutes of Health. The Government has certain rights in the invention.

FIELD OF THE INVENTION

The present invention relates to spatially resolved hydration mapping enabled by THz imaging capable of forming highly sensitive contrast maps for wound analysis, which may include of assessment of severity or viability.

BACKGROUND OF THE INVENTION

Wounds are a serious public health issue. The worldwide burden of surgical wounds and burn injuries is estimated to be ~40-50 million and ~7-10 million people, respectively (K. F. Cutting, R. J. White, and P. Mahoney, "*Int. Wound J.,* 10(1):79-86, 2013, the disclosure of which is incorporated herein by reference). Early and accurate assessment of a wound and/or its healing potential are the most important determinants of the therapeutic management of patients sustaining a cutaneous injury. The difficulty lies in distinguishing wounds or surgical tissue replacements, especially at the early stages, that will heal well without clinical intervention from those that require excision and/or surgical re-exploration to prevent necrosis. A false negative assessment has important clinical consequences: slower healing times, greater chances of infection, increased length of hospital stay, higher treatment costs, as well as a reduced functional and aesthetic outcome.

In the case of both burns and tissue flaps, which have become essential for the surgical reconstruction of patients with large soft tissue defects like burns, the difficulty with their evaluation stems from the traditional diagnostic markers of wound severity and/or viability: the appearance of the wound and sensitivity of the wound to touch. This method, which relies on the experience of a surgeon, has a poor diagnostic accuracy and can only be applied to assess the severity of burn wounds that have reached their final healing state and the viability of tissue flaps that immediately show gross signs of necrosis. Inaccurate clinical inspection can often result in unnecessary operations or delay of grafting/flap procedures. More quantitative, adjunct methods for both burn wound and tissue viability assessment primarily include tissue perfusion measurements.

SUMMARY OF THE INVENTION

Many embodiments are directed to an apparatus for assessing wound status including a Terahertz imager configured to produced spatially resolved tissue maps from a target wound area of a patient.

Several embodiments are directed to a method for THz imaging of the total water content of a wound, which may include generating a THz illumination beam having a frequency that is variable about at least one central wavelength greater than 100 GHz; illuminating a wound area with the THz illumination beam at a frequency to produce a plurality of reflected signals therefrom; detecting the plurality of reflected signals; and combining the plurality of reflected signals to obtain a THz reflectivity map of the wound area, said THz reflectivity map having a combined signal variation indicative of at least the spatially resolved total water content of the wound area.

In more embodiments, the frequency may be varied between 100 GHz and 1 THz.

In several more embodiments, the frequency is between 400 and 700 GHz.

In even more embodiments, the THz illumination beam is broadband or narrowband.

In several more embodiments, the method may also include imaging the wound area with a visible light camera to obtain a visible light image and superimposing the THz reflectivity map onto the visible light image.

In even more embodiments, the method may also include marking the wound area with a fiducial marker to align the visible light image and the superimposed THz reflectivity map.

In several more embodiments, the illumination source is one of either pulsed or continuous wave.

In even more embodiments, the illumination beam is passed through at least one dielectric window prior illuminating the wound area.

In several more embodiments, the dielectric window is comprised of at least one material that is selected from the group consisting of Mylar and quartz.

In even more embodiments, the reflectivity maps are further correlated with a separately obtained spatially imaging data selected from the group consisting of visible light imagery and magnetic resonance imaging.

In several more embodiments, the method may also include contemporaneously imaging an ideal reflector to obtain a maximum THz reflectivity and normalizing the THz reflectivity map to the maximum THz reflectivity.

In even more embodiments, the ideal reflector is an aluminum calibration target.

In several more embodiments, the reflectivity map elucidates the nature of the tissue water content gradient of the wound, and wherein the tissue water content gradient is used to identify spatial distribution of edema in the wound area.

In even more embodiments, the identification of the spatial distribution of edema includes information on the depth of edema formation in the wound area.

In several more embodiments, the identification of the spatial distribution of edema is used to medically assess a status of the wound.

In even more embodiments, the type of wound is selected from the group consisting of burns and surgical flaps.

Many embodiments are directed to a THz total water content imaging apparatus comprising, which may include a THz emission source configured to generate a THz illumination beam having a frequency that is variable about at least one central wavelength greater than 100 GHz; a detector configured to receive and record a THz signal; one or more transmission optics disposed in optical alignment between the THz emission source and a target wound area, and configured such that the transmission optics directs the THz illumination beam to impinge upon a target area on the surface of the wound area, and gathers a reflected THz signal from the target wound area and transmits the reflected THz signal to the detector; and an analyzer for using a plurality of reflected THz signals obtained of at least one illumination beam frequency to produce a plurality of reflectivity maps of the wound area, said reflectivity maps having a combined signal variation indicative of at least the total water content of the wound area.

In more embodiments, the one or more transmission optics utilize compact reflective geometries.

In many more embodiments, the apparatus is capable of producing at least one reflectivity map of the wound area in under ten minutes.

In even more embodiments, the frequency may be varied between 100 GHz and 1 THz.

In many more embodiments, the apparatus may also include a visible light camera to obtain a visible light image of the wound area.

In even more embodiments, the reflectivity maps are further correlated with a separately obtained spatially imaging data selected from the group consisting of visible light imagery and magnetic resonance imaging.

In many more embodiments, at least one dielectric window is provided atop the wound area and is configured such that the illumination beam passes therethrough in illuminating the wound area.

In even more embodiments, the at least one dielectric window is comprised of material that is selected from the group consisting of Mylar and quartz.

In many more embodiments, an ideal reflector exists within the at least one dielectric window to provide maximal reflectivity.

In even more embodiments, the ideal reflector is an aluminum calibration target.

In many more embodiments, the transmission optics at least comprise at least two 90° off-axis parabolic mirrors arranged such that the clear apertures of the parabolic mirrors are parallel and such that their focal spots overlap.

In even more embodiments, the off-axis parabolic mirror is a low f/# off-axis parabolic mirror.

In several more embodiments, the illumination beam is collimated.

In even more embodiments, the illumination source is one of either pulsed or continuous wave.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein.

DETAILED DESCRIPTION OF THE DISCLOSURE

Figure 1A:
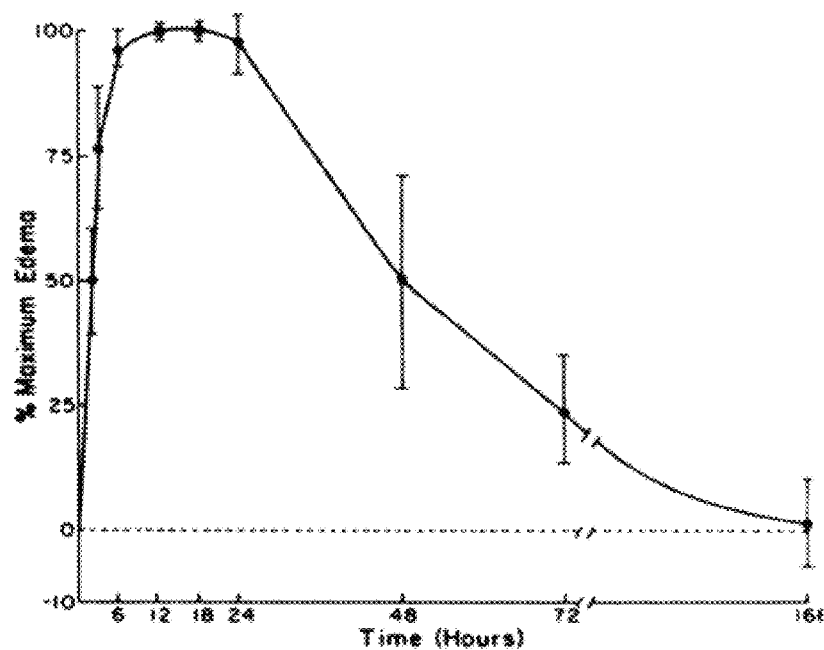
FIGS. 1A and 1B provide a chart displaying edema profiles for (A) partial thickness and (B) full thickness burn wounds.

The embodiments of the invention described herein are not intended to be exhaustive or to limit the invention to precise forms disclosed. Rather, the embodiments selected for description have been chosen to enable one skilled in the art to practice the invention.

Turning now to the drawings, systems, methods, and apparatuses for assessing wound status based on the analysis of spatially resolved tissue maps acquired with Terahertz (THz) imaging are provided. In many embodiments, terahertz imaging utilizes electromagnetic energy with frequencies between ~0.1-1 THz to generate novel contrast. In some embodiments, 400 to 700 GHz frequencies are used such that a balance is reached between scattering, sensitivity to water concentration gradients, and maximum spatial resolution. More embodiments are also directed to a THz imager that utilizes reflective geometry to illuminate and detect a sample. In even more embodiments, a THz imager utilizes an active illumination source to generate THz ray beams. Several more embodiments are directed to a THz imager that is sensitive to the detection of water, and more specifically to tissue water content. Various embodiments are also directed to measurement of relative water content in an individual's skin. In some embodiments, the measured tissue water content informs a diagnosis relative to medical conditions, such as, for example, wound status, including, for example, burn wound or surgical flap viability.

Wound Status

Quantitative, remote sensing of wound status is an active area of research with a small but quickly expanding clinical presence. Systems can easily be broken into two types: morphological and non-morphological. Morphological systems such as optical coherence tomography (OCT) and scanning confocal microscopy generate 3D resolved maps of tissue structure. These maps do take into consideration tissue function and thus the acquired morphological information may not correlate at all to the wound status. Non-morphological systems attempt to acquire functional information of the tissue of interest. The most popular of these assess blood perfusion through Laser Doppler imaging (LDI) processing. LDI is a useful technique for studying and estimating perfusion characteristics of burn wounds as well as tissue flaps in vivo only after wound-associated edema (i.e., fluid accumulation within and swelling of wounded tissue) has completely subsided (W. Eichhorn, T. Auer, E.-D. Voy, and K. Hoffmann, *J. Cranio-Maxillofac. Surg.*, 22(5):301-06, 1994; A. D. Jaskille, et al., *J. Burn Care Res.*, 31(1):151-57, 2010; S. A. Pape, C. A. Skouras, and P. O. Byrne, *Burns*, 27(3):233-39, 2001; the disclosures of which are incorporated herein by reference). This is typically ~48 hours in advance of clinical judgment, indicating clinical experience alone requires at least 3-4 days of elapsed time to arrive at sufficient prediction accuracy. Although the overall accuracy of burn depth and flap viability assessment using LDI techniques has been reported to be as high as 92% compared to histology, it is still significantly confounded by the presence of edema in the wound bed during the acute stages (i.e., the first 24 hrs) of injury. Excess tissue water content (TWC) in the wound affects wound temperature by increasing tissue heat capacity and heat conductivity, which can alter flow readings and perturb laser illumination fluence and the detection of Doppler shifted signals.

Figure 1B:
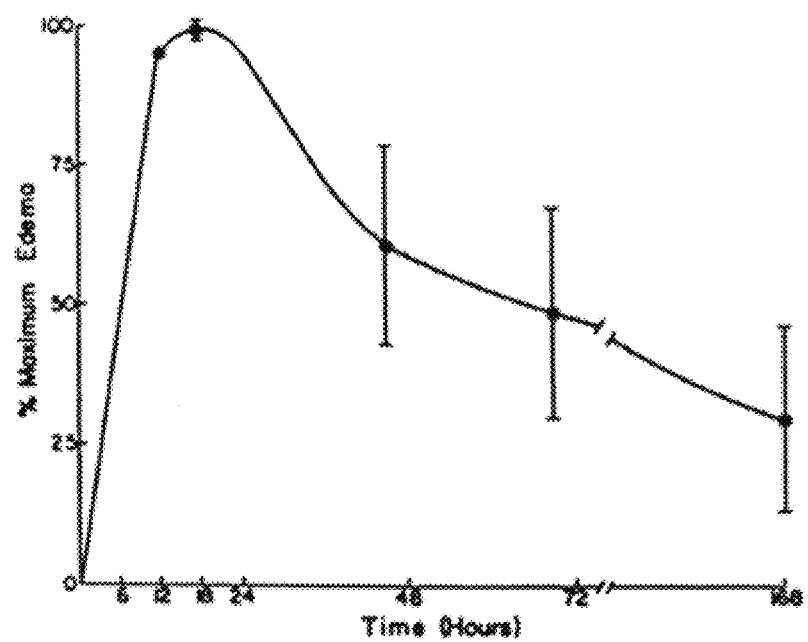

Profound tissue edema, or swelling, is a well-recognized entity following injury. Edema is most prominent in or directly surrounding injured tissues, however, edema formation can also be found in non-traumatized tissues nearby. The rate of edema formation is very rapid. Using the noninvasive photon scanning technique, it has been reported that most (90%) of the edema was present by 4 hours after a partial thickness limb burn (R. H. Demling, *J. Burn Care*, 3(3):138-49, 1982, the disclosure of which is incorporated herein by reference). The maximum edema was present at 12 hours (FIG. 1A), when the rate of edema formation was mitigated by the rate of edema dissipation (R. H. Demling, *J. Burn Care Res.*, 26(3):207-27, 2005, the disclosure of which is incorporated herein by reference). In full thickness burns, edema occurs slower, likely due to decreased dermal perfusion in severally damaged tissue (FIG. 1B).

Significant data in the literature confirms the accumulation, organization, and resporption of tissue edema following injury of surface tissue. This data also suggests that wound status may correlate with the level of edema, but currently no methods using tissue edema exist due to the difficulties of sensing tissue water content in vivo with high sensitivity and specificity. Indeed, wound status assessment is, in many cases, confounded by the presence of tissue edema. Because tissue edema is often strongly pronounced immediately following injury, this limitation in conventional systems can prevent early and accurate assessment of a wound. In many cases, medical practitioners must wait for the edema to resorb before evaluating a wound, which can be days until after the original injury.

Embodiments of THz Imaging Apparatus

Many embodiments are directed to THz systems and methods configured to utilize the terahertz spectral region (i.e., 0.1-1 THz) to characterize the molecular dynamics of water and to determine the effects of water in biological systems. Many of these embodiments utilize measurements of water that may be analyzed in terms of the complex dielectric constant c*(w) in EQ. 1, where w denotes the angular frequency, or the complex refractive index n*(w) in EQ. 2 where:

$$\varepsilon^* = \varepsilon(\omega) - i\varepsilon(\omega) \qquad \text{EQ. 1}$$

$$n^* = n(\omega) - iK(\omega) \qquad \text{EQ. 2}$$

With ε, ε' and n, K denoting the real and complex components of ε* and n*, respectively. Simple dielectric relaxation models for permittivity and conductivity, specifically the Double Debye model, agree with the experimentally derived complex dielectric constant of water up to at least 1 THz, accordance with multiple embodiments.

Figure 2:
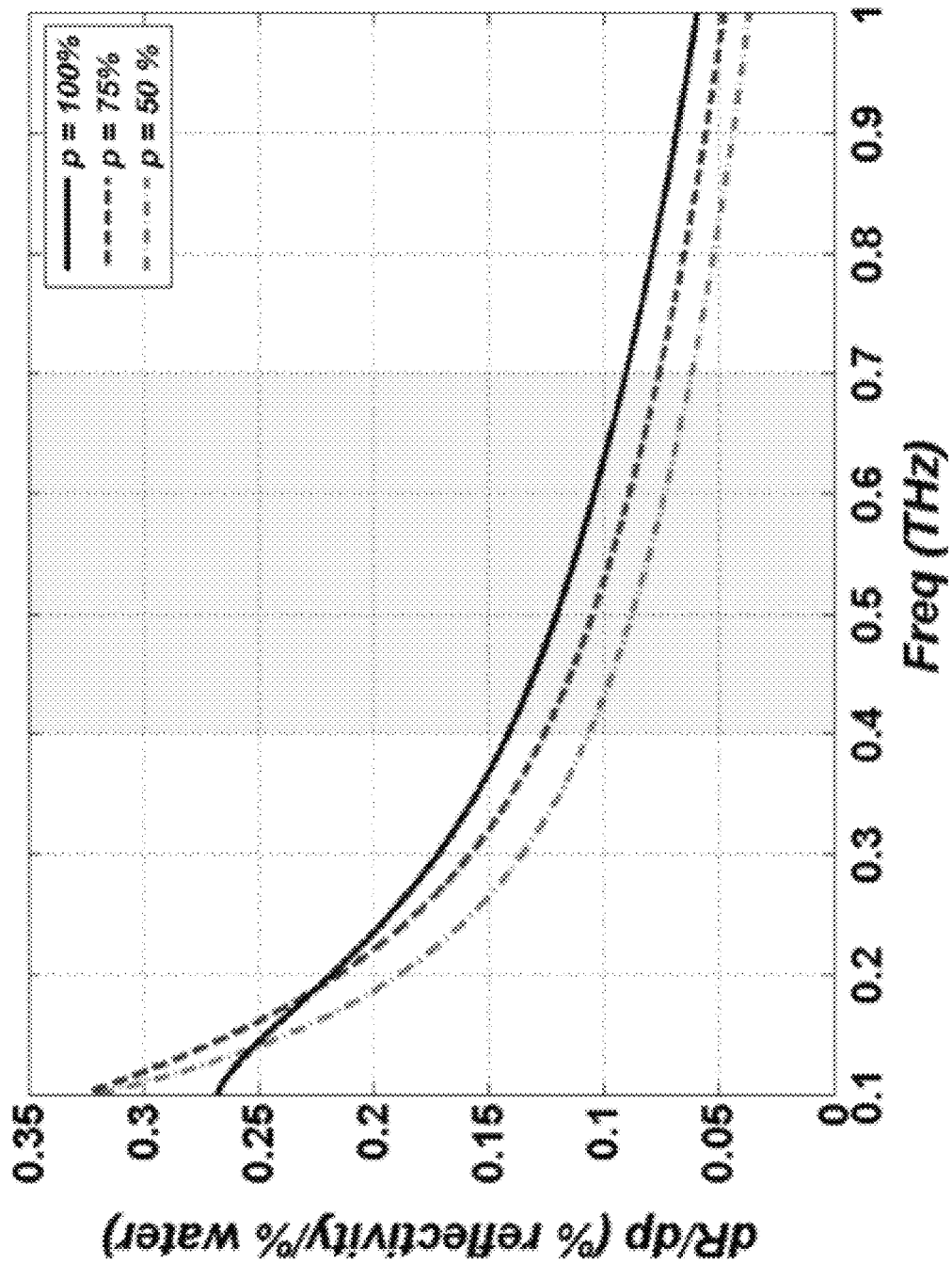
FIG. 2 provides a data graph displaying intrinsic hydration sensitivity as a function of water concentration and illumination frequency using the double Debye dielectric model and Bruggeman effective media theory, which is utilized in accordance with various embodiments.

Accordingly, several embodiments are directed to THz imaging that are configured to utilize the dielectric properties of water to provide sensitivity to water concentration and changes in water concentration in an imaged region. In specific embodiments, the intrinsic hydration sensitivity is a function of water concentration and illumination frequency may be determined using the Debye dielectric model and/or the Bruggeman effective media theory. In FIG. 2, reflectivity trends based on the Debye dielectric model and Bruggeman effective media theory are displayed. As shown, lower frequency illumination provides greater reflectivity and produces greater changes in reflectivity for a given change in water contrast with 6 times more sensitivity at 100 GHz as compare to 1 THz. Accordingly, various embodiments incorporate the use of lower frequency THz frequency, to provide better water concentration sensitivity.

In many embodiments, the energy levels associated with THz wavelength imaging result in large absorption when transmitted through water and large return powers when reflected from water. Conversely, most other non-aqueous, non-conductive materials such as non-water tissue constituents are nearly transparent. These unique properties enable embodiments of imaging systems based on THz illumination to acquire highly sensitive maps of variations in TWC of an area that are robust to confounders typically faced in in vivo imaging (skin thickness variation, hair, curvature, etc.). Many embodiments of systems and methods leverage this capability to generate hydration maps from a range of tissue types and pathologies including burns.

Figure 3:
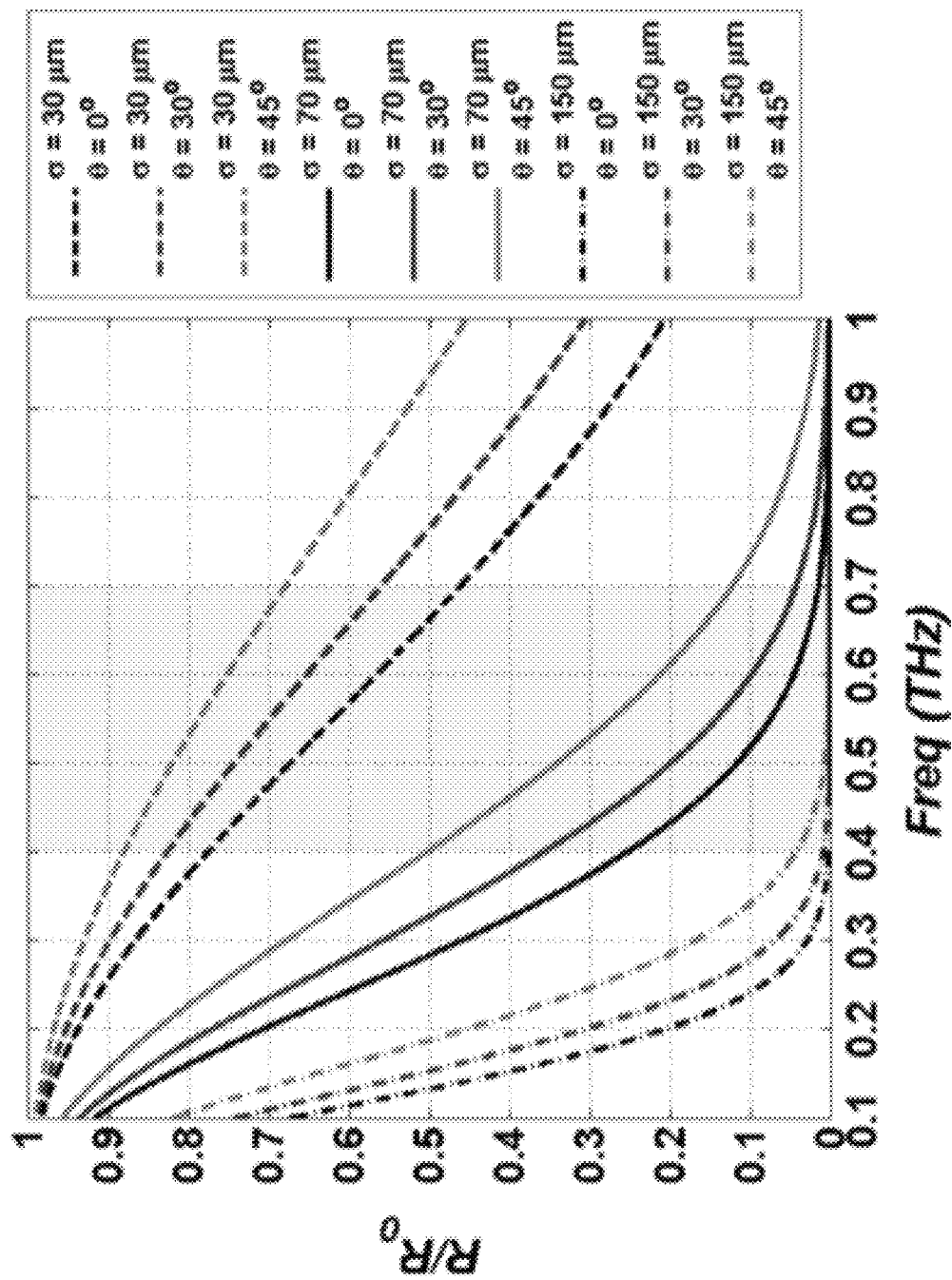
FIG. 3 provides a data graph displaying simulations of Rayleigh scattering for pairs of root mean square (RMS) surface roughness and incidence angle, which is utilized in accordance with various embodiments.

Many more embodiments are directed to overcoming the inherent scattering of THz imaging. Scattering from rough surfaces is a well-known problem often observed in optics. In THz medical imaging, particularly the imaging of skin, typical target feature sizes approach hundreds of micrometers, placing them directly in the middle of the wavelength bands of interest. This poses a significant problem for hydration sensing, where small changes in hydration dependent reflectivity may be masked by random scattering due to target geometry. Accordingly, embodiments are direct to the use of the Rayleigh roughness factor to model frequency dependent scattering in the THz regime. Further embodiments utilize lower frequencies, which are much more robust to scattering than higher frequencies, and tissues appear more specular in the millimeter wave range (e.g., below 700 GHz) than they do in the sub-millimeter (as demonstrated in FIG. 3).

Figure 4:
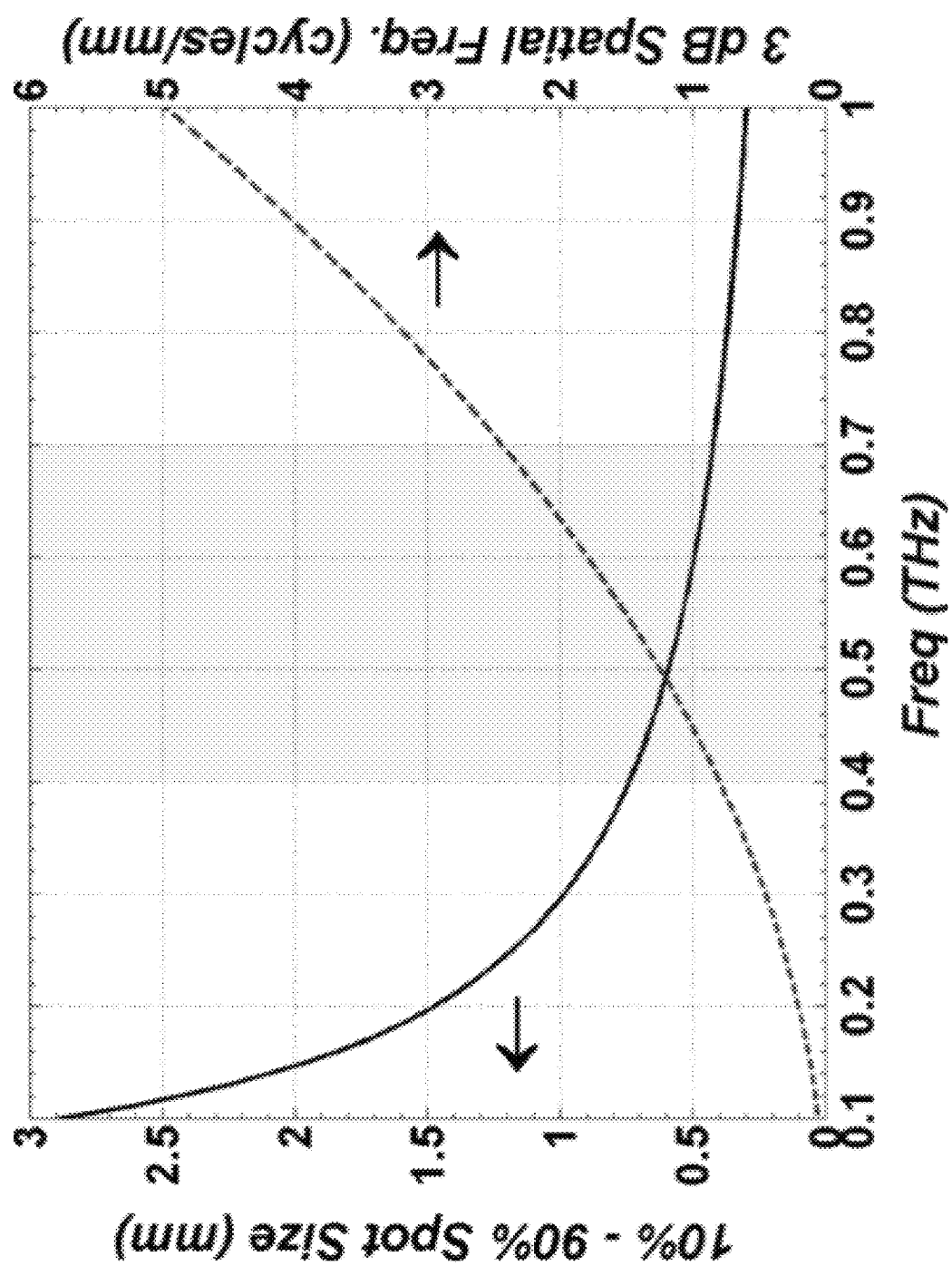
FIG. 4 provides a data graph displaying THz imaging system resolution as a function of frequency, which is utilized in accordance with various embodiments.

Various embodiments are also directed to THz imaging systems having improved spatial resolution that are capable of sensing small changes in hydration in proximate spatial discrimination. Theoretical spatial resolution limits were calculated using Gaussian beam theory and provided in FIG. 4. For the purposes of this simulation, a high numerical aperture, 25.4 mm effective focal length off-axis parabolic mirror with a 25.4 mm clear aperture 90% filled by the THz beam was used, but any appropriate inputs would yield similar results. As can be seen from the simulation, higher frequencies produce a smaller spot size for a given optic and hence are able to resolve higher spatial frequencies. Accordingly, various embodiments are directed to systems and methods utilizing higher frequencies to improve spatial resolution.

Figure 5:
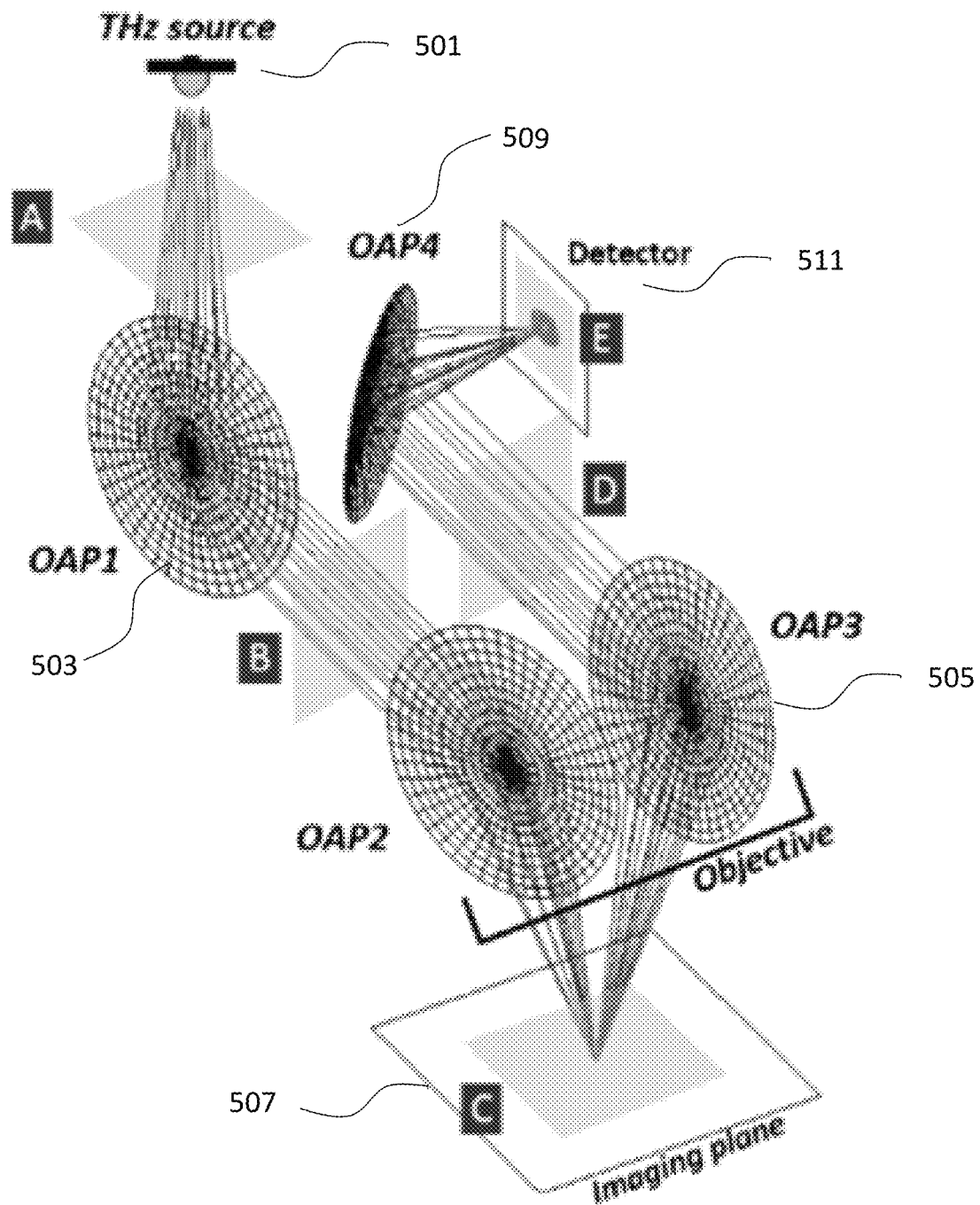
FIG. 5 provides a ray diagram of a THz imaging system with optics and receiver components in accordance with various embodiments.

In many embodiments, THz imaging systems utilize an optical reflection geometry where an incident light source is reflected off the surface of a target wound area, and where the reflected light is then gathered and analyzed (as shown in FIG. 5). In number embodiments, the THz system operates in a reflection mode at between 0.1 and 1 THz (e.g., 0.5 THz with ~125 GHz bandwidth), which is illuminated from an appropriate source (501). The resulting THz source beam is collimated by an effective focal length (EFL) optic. In several embodiments, the THz source beam is collimated utilizing a clear aperture off-axis parabolic (OAP) mirror (503).

Figure 6:
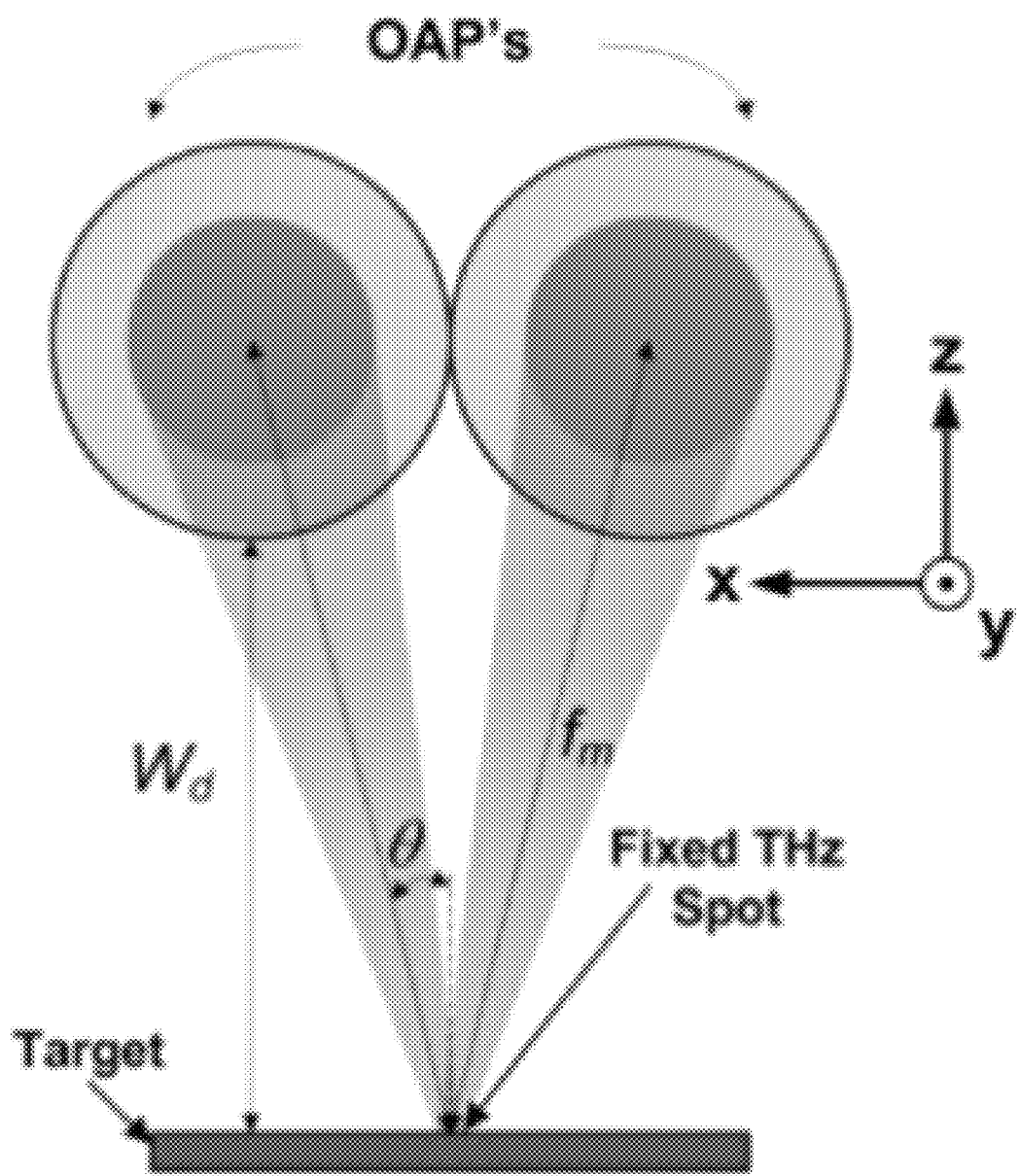
FIG. 6 provides a schematic of illumination geometry, where the incidence angle and working distance are function of the OAP length and clear aperture in accordance with various embodiments.

In more embodiments, the system employs a THz reflective objective where 2 identical OAP mirrors are mounted such that their clear apertures normal vectors are parallel and their focal spots overlap (505). This objective takes in a collimated source beam and focuses the THz on target (507), collects the diverging reflection, and outputs a collimated beam towards another OAP mirror (509) and the detector optics (511). A front on view of the geometry is displayed in FIG. 6, where $f_m$ is the mirror effective focal length (EFL) and $W_d$ is the working distance of the objective assembly. Multiple embodiments are also directed to THz objectives which allow OAPs of varying EFL to be changed without needing to realign the THz beam. In addition, various embodiments are directed to designs of systems that minimize laser alignment and robust to misalignment. More embodiments of THz imagers are compact, improving the portability of the system. Embodiments utilizing these reflection geometries have several advantages, including clinically feasible geometries that render in vivo imaging possible, sufficient spatial resolutions, and rapid acquisition rates.

Numerous embodiments of THz systems utilize active illumination sources, which can enhance the signal-to-noise ratio and reduce the sensitivity requirement. In other embodiments a passive system can be used in accordance with various embodiments when an appropriate level of THz emission is detectable. Table 1 below describes various parameters that may be used in choosing between active and passive imaging in accordance with embodiments.

TABLE 1

PROS AND CONS OF ACTIVE AND PASSIVE IMAGING

| | Active Imaging | Passive Imaging |
| --- | --- | --- |
| Detector sensitivity | Low | High |
| Sensitivity to environment | Relatively low | High |
| Detection range | Limited by source-object distance | Relatively long |
| Image interpretation | Difficult due to coherent artifacts | Easy |
| Covert operation | No | Yes |
| Safety concern | None based on testing | No |

In several embodiments, the THz sources can be narrowband or broadband, dependent on need. Narrowband THz sources can improve high-resolution spectroscopy applications. On the other hand, broadband sources are typically higher speed, which can be beneficial when performing in vivo imaging. Any appropriate generation of THz spectra can be used in accordance with numerous embodiments. For example, photoconduction and optical rectification are two common approaches for generating broadband pulsed THz beams (B. Ferguson and X. C. Zhang *Nat. Mater.*, 1(1):26-33, 2002, the disclosure of which is incorporated herein by reference).

In multiple embodiments, active THz systems can use either pulsed or continuous wave (CW) illumination. In some of these embodiments, pulsed imaging and spectroscopy is preferred for biomedical applications, which may exhibit high signal-to-noise ratios (SNR) and provide depth information. In other embodiments, CW illumination can be employed, which affords a compact, simple, fast and relatively low-cost system. Examples of pulsed and CW THz imaging systems are provide in FIG. 7 and FIG. 8, respectively.

Figure 7:
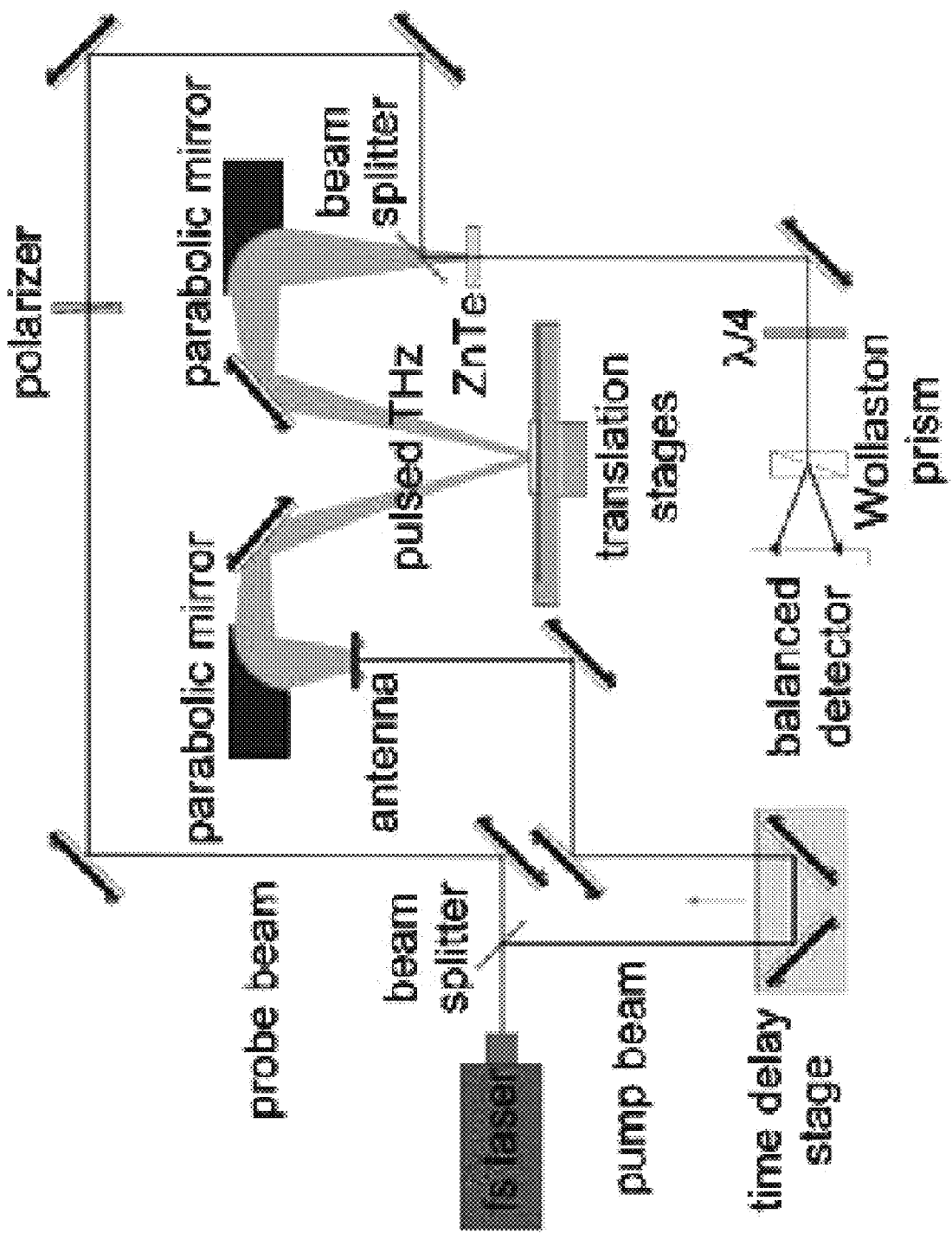
FIG. 7 provides a schematic block diagram of a pulsed THz imaging system in accordance with various embodiments.
Figure 8:
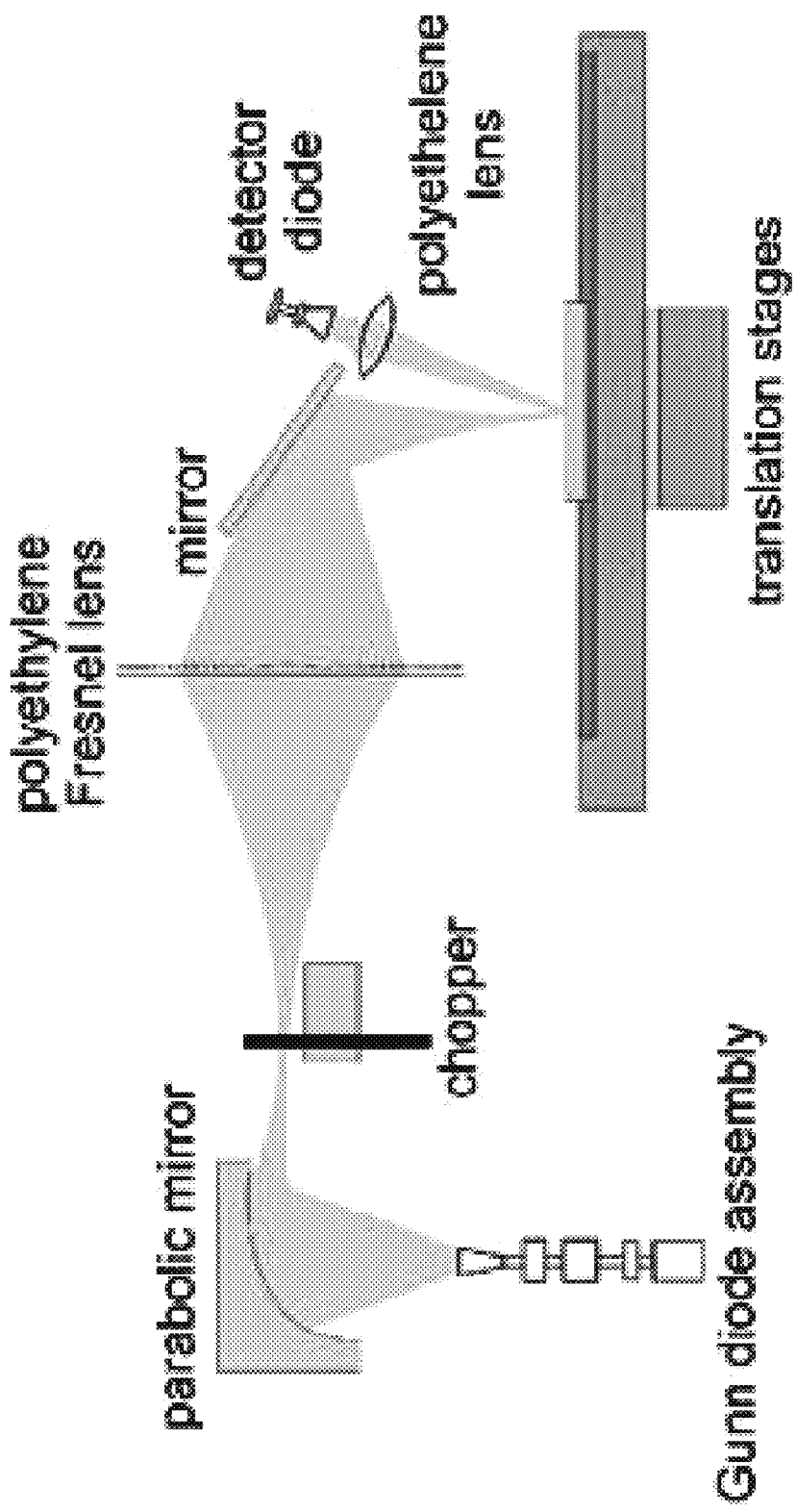
FIG. 8 provides a schematic block diagram of a continuous wave THz imaging system in accordance with various embodiments.

Various embodiments of THz pulsed systems are comprised of a femtosecond laser, THz source, pair of optical transducers, and a detector (FIG. 7). In many of these embodiments, the laser pulse is split into two components—pump and probe. The pump is used to excite the THz source, which, in several embodiments, is either a photoconductive antenna or a non-linear crystal. Using parabolic mirrors, the generated THz pulse is focused onto a target and the reflected beam is collimated and focused into a detector where it is mixed with the laser probe beam. The signal is then amplified, down converted to radio frequency range, and detected.

Figure 9:
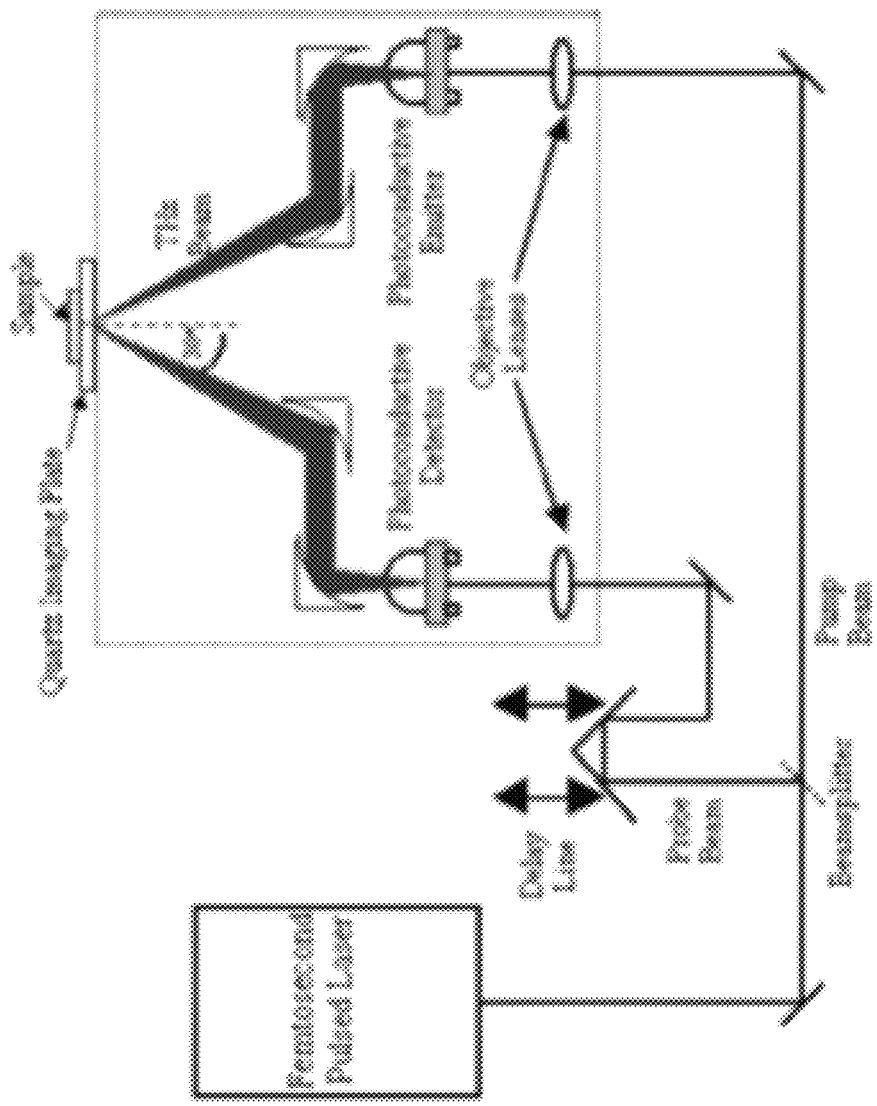
FIG. 9 provides a schematic block diagram of a THz time domain imaging system in accordance with various embodiments.

In more embodiments, time domain THz imaging is utilized when a large amount of data is to be obtained (e.g., hyperspectral imaging). An example of time domain imaging system is portrayed in FIG. 9. The receiver and transmitter are usually identical photoconductive switches. A femtosecond pulsed 780 nm laser is split into two arms: 1) a pump beam, which is sent to a biased photoconductive emitter; and 2) a probe beam, which is passed through a variable delay line and then sent to an unbiased photoconductive detector. The biased photoconductive emitter generates THz radiation, which is directed to the target and then back to photoconductive detector. The probe pulse modulates the resistance of the photoconductive detector switch for a very short time, allowing optoelectronic sampling of the electric field of the incoming THz pulse in the form of a photo current. The optical delay line is then swept and the entire pulse is sampled as a function of delay line position and hence time.

Embodiments of THz systems can use various THz detectors, appropriate for the application and use, which can range from superconductor bolometers to heterodyne sensors. In many embodiments, coherent detectors are used for biomedical imaging and spectroscopy. Two commonly used schemes for coherent detection are photoconductive detection and electro-optical sampling. Both detection schemes involve mixing the THz pulse with a part of the original laser pulse. An optical delay line ensures the simultaneous arrival of both pulses.

Several embodiments are directed towards non-contact THz imaging systems. Several other embodiments are instead directed to the use dielectric substrate windows. In many of these embodiments, dielectric substrate windows are used to minimize confounding effects from surface roughness, non-planar geometries, and respiratory artifacts associated with an in vivo target. In accordance with several embodiments, both high and low dielectric substrates can be used, including, but not limited to, quartz, sapphire, and Mylar film. In more embodiments, the dielectric substrate thickness can vary, from roughly 5 µm to 1000 µm, dependent on the substrate and the application. In specific embodiments, the dielectric window is roughly 12.7 µm Mylar. In other embodiments, the dielectric window is roughly 50 µm quartz.

Embodiments using various dielectric windows may be configured to yield unique TWC image contrast maps. For example, in accordance with various embodiments, THz reflectivity associated with the burn contact region of a wound with respect to uninjured tissue results may increase THz reflectivity and decrease THz reflectivity when imaged with a Mylar and quartz window, respectively. However, despite the difference in the generated contrast maps, Mylar and quartz dielectric windows each yield an accurate diagnosis of wound edema, because THz burn contrast associated with each window is both unique and consistent with known TWC trends in burn edema pathogenesis. Accordingly, various embodiments are directed to window-driven, high-speed THz imaging for the detection and monitoring of pathological conditions that lead to tissue edema.

Many more embodiments are directed to the simultaneous use of a THz imager and a visible light camera (e.g., single lens reflex (SLR) camera) to take a visible light images (i.e., photographs) of the tissue. Accordingly, the THz-generated contrast maps can be superimposed onto photographs sharing a similar focal plane. In a number of embodiments, external fiducial markers are used to align THz images to their respective visible pictures.

Various embodiments also utilize contrast mechanisms to identify water content in an image. In several of these embodiments, THz reflectivity values of contours are normalized to a maximum and a minimum THz reflectivity acquired. In a number of embodiments, an ideal reflector (e.g., aluminum calibration target) is used as a maximum THz reflectivity. In more embodiments, THz reflectivity measured in the absence of a reflecting target (i.e. air) to obtain a minimum reflectivity. In even more embodiments, the reflectivity values are determined on a pixel-by-pixel basis.

Methods for Wound Analysis Using THz Imaging

Multiple embodiments are also directed to utilizing the THz-imager generated data for medical assessment. Accordingly, many embodiments are directed to the use of hydration mapping to assess wound status. Specifically, in several embodiments, variations in spatiotemporal THz measurements directly correlate with tissue water content. Accordingly, various embodiments are directed to building THz-TWC maps on tissue in vivo. More embodiments utilize generated THz-TWC maps to identify edema in certain locality within a tissue. It has been found that using THz imaging turns the presence of dermal edema into a contrast mechanism, and allows for the use of the spatial distributions of edema to assess wound status immediately. Accordingly, in further embodiments, THz systems and methods are capable diagnosing of wounds using the spatiotemporal THz measurements that identify wound-associated edema. In some of these embodiments, medical assessment occurs within an hour of injury. In more embodiments, medical assessment occurs within ten minutes of injury. In further embodiments, combined MRI-THz fusion methods may be utilized.

In many such embodiments, THz-TWC maps gathered from reflective THz imaging of burn wounds may be used to diagnose wound severity acutely and to predict future wound outcomes based on resolving spatial distributions of edema. It is now known that utilizing a reflective THZ imaging system, various burns can be delineated based on their image contrast. For example, in accordance with many embodiments, full thickness burns (i.e., burn depth into subcutaneous tissue) exhibit decreased THz reflectivity at the contact site compared to partial thickness burns (i.e., burn depth into reticular region) when imaged with a thin Mylar window. These differences are due to the innermost region skin tissue containing irreversibly damaged cells and possible damage to the vasculature in full thickness burns, thus not allowing water to flow to the contact area to form edema. Accordingly, various embodiments are directed to utilizing THz imaging systems to diagnose the depth of damage based on the relative amount of TWC at the contact site. In some other embodiments, an algorithm is provided to differentiate partial thickness burns and full thickness burns using imaging data and pathological assessments. Using such embodiments in accordance to embodiments allow for the diagnosis of an unknown injury severity status by examining both the patch of skin and concentric rings of skin surrounding the unknown area. In many embodiments the algorithm may use the reflectivities of the patch and the surrounding rings to differentiate between partial and full thickness burns.

In other such embodiments, THz-TWC maps gathered from reflective THz imaging of surgically excised flaps may be used to diagnose viability and health and to enable expedited surgical re-exploration and potential salvage of failing tissue flaps prior to irreversible ischemia. In many of these embodiments, THz reflectivity profiles can be generated along the surgical flap margin to assess whether fluid content is able to flow back into the repaired flap as early as immediately following surgery. When utilizing a thin Mylar window, in accordance with multiple embodiments, high THz reflectivity indicates robust water content associated with uninjured and/or repaired tissue. in accordance of more embodiments, statistically significant variation in THz reflectivity between a flap survival and flap failure is observed twenty-four hours prior to observable gross changes in tissue viability using clinical inspection alone. Accordingly, embodiments are directed to the post-surgical diagnosis of flap assessment, wherein a lack TWC suggests insufficient hydration and gradual procession to necrosis and poor clinical outcome.

In many embodiments, methods for spatially assessing wound status are provided. In such embodiments, a specific region of tissue is assessed by examining the statistical properties of the tissue in a THz image grouped by a segmentation performed on a coregistered visible image. This coregistration allows the assessment to superimposed on the visible image.

In many embodiments, systems are provided whereby manifolds with varying radius and concentric to the tissue area of interest tissue are superimposed on Terahertz tissue water maps. Pixels within specific manifolds are grouped, features identified, and classifiers based on these features are generated. These classifiers can be used to delineate, with a high degree of sensitivity and specificity, what tissues are in need of intervention, what tissues will heal, what tissues are necrotic, etc. Further, in many embodiments these parameters can be predicted with good spatial localization for any area in the field of view many days beyond the initial image acquisition time.

Exemplary Embodiments

The following sections set forth certain selected embodiments related to the above disclosure. It will be understood that the embodiments presented in this section are exemplary in nature and are provided to support and extend the broader disclosure, these embodiments are not meant to confine or otherwise limit the scope of the invention.

Example 1: THz Imaging Burn Analysis

In many embodiments, methods and apparatus are provided that utilize THz tissue water content (TWC) mapping of burns to predict wound tissue viability and produce THz viability maps with the goal of improving burn wound outcome. The overarching goal of burn wound diagnostics is to rapidly distinguish tissues in the wound that are viable from those that are not. Such advancements in THz burn imaging translate to identification of key clinical outcomes, specifically which areas will heal spontaneously without medical intervention and which areas require debridement.
State of the Art Wound Imaging Several burn wound imaging systems under investigation use optical technologies because, in general they provide spatially resolved burn wound assessment. These include vital dyes, polarization sensitive optical coherence tomography (PS-OCT), and thermal imaging. (See, e.g., J. E. Gatti, et al., *J Trauma*, vol. 23, pp. 202-6, March 1983; B. H. Park, et al., "*J Biomed Opt*, vol. 6, pp. 474-9, October 2001; M. C. Pierce, et al., *Burns*, vol. 30, pp. 511-7, September 2004; A. G. Hargroder, et al., "Infrared imaging of burn wounds to determine burn depth," 1999, pp. 103-108; and J. Ruminski, et al, *IEEE Trans Biomed Eng*, vol. 54, pp. 303-12, February 2007, the disclosures of which are incorporated herein by reference.)

Laser Doppler Imaging (LDI), the only currently FDA approved technique for burn wound assessment, infers burn wound depth through measurements of blood perfusion in the wound bed. (See, e.g., S. A. Pape, et al., *Burns*, vol. 27, pp. 233-9, May 2001; A. J. Holland, H. C. Martin, and D. T. Cass, *Burns*, vol. 28, pp. 11-7, February 2002; J. C. Jeng, et al., *Burns*, vol. 29, pp. 665-70, November 2003; H. Hoeksema, et al., *Burns*, vol. 35, pp. 36-45, February 2009; and A. D. Jaskille, et al., *J Burn Care Res, vol.* 31, pp. 151-7, January-February 2010, the disclosures of which are incorporated herein by reference.) The accuracy of LDI is confounded significantly by the presence of wound edema and excess fluid in the interstitial spaces of both the dermis and epidermis. Excess wound hydration perturbs wound temperature by increasing tissue heat capacity and heat conductivity which can alter flow readings. Additionally, wound edema occurs throughout tissue including the epidermal/dermal junction which perturbs laser illumination fluence and the detection of Doppler shifted signals. All these factors limit the clinical application of LDI.

Vital dyes techniques are adept at detecting necrosis which is a predictor of burn wound depth. However, normal skin controls are necessary and the images have relatively low intrinsic contrast and spatial resolution. (See, A. D. Jaskille, et al., *J Burn Care Res, vol.* 30, pp. 937-47, November-December 2009, the disclosure of which is incorporated herein by reference.) Vital dye contrast is also often unusable in the acute phase because the dye can leak out from damage blood vessels and edema can perturb the illumination fluence and emission intensities. Dye can also permeate the interstitial space in the wound beds due to the increased presence of water.

PS-OCT systems can assess burn depth through the information through depth resolved measurements of polarization rotation induced by collagen denaturation. Additionally, tissue edema can perturb polarization rotation sensing as the swelling of collagen fibers due to excess water will change the polarization resolved signature of the bulk tissue. (See, e.g., T. Gambichler, et al., *Journal of Dermatological Science*, vol. 40, pp. 85-94, November 2005; and S. M. Srinivas, et al., "*Journal of Biomedical Optics*, vol. 9, pp. 207-212, 2004, the disclosures of which is incorporated herein by reference.) However the imaging fields are too small and the depth of penetration is limited to a few millimeters. While progress is being made no large scale clinical application of PS-OCT for burn assessment has been reported.

The following provides results from significant in vivo work measuring gradients in tissue water content (TWC) with applications to both burn wound severity diagnosis. (See, e.g., J. Y. Suen, et al., "Reflective, pulsed THz system for biomedical imaging," in *International Workshop on Optical Terahertz Science and Technology*, Santa Barbara, Calif., 2011; Z. D. Taylor and W. S. Grundfest, "Medical imaging and Therapeutics at UCLA," in *Univeristy of California Biophotonics Alliance (UCBA)*, Lake Tahoe, N V, 2011; B. N. Nowroozi, et al., "Preliminary Evaluation of Full and Partial Thickness Burn wounds in vivo using Terahertz Imaging," in *Advanced Technology Applications to Combat Casualty Care: ATACC*, Fort Lauderdale, Fla., 2012; N. Bajwa, et al., *SPIE Terahertz Emitters, Receivers, and Applications III*, San Diego, Calif., 2012, pp. 84960X-84960X; P. Tewari, et al., *SPIE Terahertz Technology and Applications V*, San Francisco, Calif., 2012, pp. 82610T-82610T; S. Sung, et al., *SPIE Terahertz Emitters, Receivers, and Applications III*, San Diego, Calif., 2012, pp. 84960S-84960S; N. Bajwa, et al., *SPIE Terahertz and Ultrashort Electromagnetic Pulses for Biomedical Applications I*, San Francisco, 2013; Z. D. Taylor, et al., *SPIE Terahertz, RF, Millimeter, and Submillimeter-Wave Technology and Applications VI*, San Francisco, 2013; Z. D. Taylor, et al., "THz Medical Imaging," in 6th *ESA Workshop on millimetre Wave technology and applications and 4th Global symposium on millimeter Waves*, Helsinki, Finland, 2011; Z. D. Taylor, et al., *SPIE Terahertz Emitters, Receivers, and Applications II*, San Diego, Calif., 2011, pp. 811906-811906; R. S. Singh, et al., *SPIE Advanced Biomedical and Clinical Diagnostic Systems VIII*, San Francisco, Calif., 2010, pp. 755513-755513; E. R. Brown, et al., *Infrared Millimeter and Terahertz Waves (IRMMW-THz)*, 2010 35th International Conference on, 2010, pp. 1-2; Z. D. Taylor, et al., *Microwave Symposium*, 2007. *IEEE/MTT-S International*, 2007, pp. 1161-1164; Z. D. Taylor, et al., *SPIE Terahertz for Military and Security Applications VI*, Orlando, Fla., USA, 2008, pp. 69490D-8; R. D. Johnson, et al., "Novel corneal hydration imaging technology using Terahertz Illumination," in *Association for Research in Vision and Ophthalmology (ARVO) Annual Meeting,* 2011; R. S. Singh, et al., "Terahertz sensing of corneal hydration," in *Engineering in Medicine and Biology Society (EMBC),* 2010 Annual International Conference of the IEEE, 2010, pp. 3021-3024; D. Bennett, et al., *Journal of Biomedical Optics,* vol. 17, pp. 097008-1, 2012; and D. B. Bennett, et al., *Journal of Biomedical Optics,* vol. 16, pp. 057003-057003, 2011, the disclosure of each of which are incorporated herein by reference.)

Several key observations can be made regarding the currently available armamentarium of diagnostic technologies. First, all of the technologies, save for PS-OCT, focus on either a direct or indirect measurement of blood perfusion and flow. PS-OCT focuses only on differential changes in the ordered structure of collagen. The physical depth of damage is not explicitly measured but inferred from knowledge of physiology combined with the measured physiologic parameter. Further, several of the studies were correlated with pathology and researchers observed that quantitative measurements of depth did not always correlate with time to heal. (See, S. Monstrey, et al., *Burns,* vol. 34, pp. 761-769, September 2008, the disclosure of which is incorporated herein by reference.) This suggests that physical depth information, while a marker to determine the severity and healing viability of the burn, is not necessarily a key clinical parameter. Further, this also suggests that physiologic (structural and functional) markers may be used to directly predict tissue viability.

Second, every quantitative diagnostic technique that has been researched for burns is confounded by the presence of wound edema. (See, S. Monstrey, et al., *Burns,* vol. 34, pp. 761-9, September 2008, the disclosure of which is incorporated herein by reference.) Increased tissue hydration perturbs wound temperature, pressure, blood perfusion, and the properties of light reflected from the wound bed. If left untreated, wound edema rises significantly in the first 12 hours for both superficial second and deep second degree burns, peaks sometime in the first 24 hours, and then begins to resorb throughout day 2. (See, R. H. Demling, R. B. Mazess, and W. Wolberg, *J Trauma,* vol. 19, pp. 56-60, January 1979, the disclosure of which is incorporated herein by reference.) To this end, many researchers conclude that the dynamic properties of burn wound status and wound edema prevents quantitative analysis in the first 48 hour following injury. Note that LDI has been shown to determine the need for excision and grafting ~48 hours in advance of clinical judgment indicating that clinical experience alone requires at least 3-4 days of elapsed time to arrive at sufficient prediction accuracy.

Embodiments of THz imaging methods and apparatus can identify burn wound severity as early as 30 minutes following thermal insult, and the technique maintains diagnostic power throughout the first 8 hours post injury. This identification is at least 48 hours earlier than that of all incumbent burn diagnostic imaging techniques. (See, e.g., N. Bajwa, et al., *IEEE,* 2014; and P. Tewari, et al., "*IEEE,* 2014, the disclosures of which are incorporated herein by reference.)

Predictive Nature of Wound Edemas

Pathohistologic studies and osmotic pressure measurements have documented the dynamic changes of wound edema in superficial second, deep second, and third degree burns. (See, e.g., T. Lund, H. Onarheim, and R. K. Reed, *World J Surg,* vol. 16, pp. 2-9, January-February 1992; and G. Arturson, *Burns,* vol. 22, pp. 255-274, June 2096, the disclosures of which are incorporated herein by reference.) Although these studies employed point measurements and are more prone to sampling error than imaging techniques, they elucidate significant buildup and reorganization of interstitial hydration during the first 24-48 hours following burn injury. Furthermore, differences in both buildup rate and peak levels were observed suggesting predictive power.

The healing viability prediction power of wound bed hydration was first explored with Nuclear Magnetic Resonance (NMR). (See, M. J. Koruda, et al., *J Surg Res,* vol. 40, pp. 475-81, May 1986, the disclosure of which is incorporated herein by reference.) Animal studies were performed that determined spin-lattice ($T_1$) and spin-spin ($T_2$) relaxation times of tissue excised from both second and third degree burns in rat models. Tissue water content (TWC) was determined from these relaxation times and correlated with thermogravimetric analysis. Both second degree and third degree burns displayed significant elevations of TWC 3 hr after injury ($p<0.001$). At 48 hours postburn the TWC of the second degree burn group had decreased to control values while the TWC of all third degree burns remained significantly elevated as compared to both the control and the 48-hr second degree burn TWC ($p<0.001$). These results demonstrate the predictive power of wound hydration. Furthermore, it shows that, contrary to the conventional view, wound edema can be leveraged as a contrast mechanism, not a confounder. However, this technique has not translated successfully to the clinic due to the prohibitive cost, time, and practical issues inherent in NMR.

THz Imaging of Burn Wounds

In accordance with embodiments imaging systems and novel prognostic tools based on this system are provided to evaluate burn wounds. In many embodiments THz imaging systems for burn wound mapping capable of distinguish spatiotemporal differences in reflectivity between partial and full thickness burns are provided. (See, e.g., P. Tewari, C., et al., *Journal of Biomedical Optics,* vol. 17, pp. 040503-3, 2012; P. Tewari, et al., *Journal of Biomedical Optics,* vol. 17, p. 040503, 2012; and Z. D. Taylor, et al., *Opt. Lett.,* vol. 33, pp. 1258-1260, 2008, the disclosures of which are incorporated herein by reference.) Embodiments of parallel MR and THz imaging studies are also provided to demonstrate the feasibility of side-by-side 7 T MRI and THz monitoring of burn wounds and validation of hydration as the principle source of contrast in THz burn imaging. In many embodiments, MRI-THz parallel imaging is provided to detect spatially resolved burn severity in vivo using either imaging modality.

Figure 10:
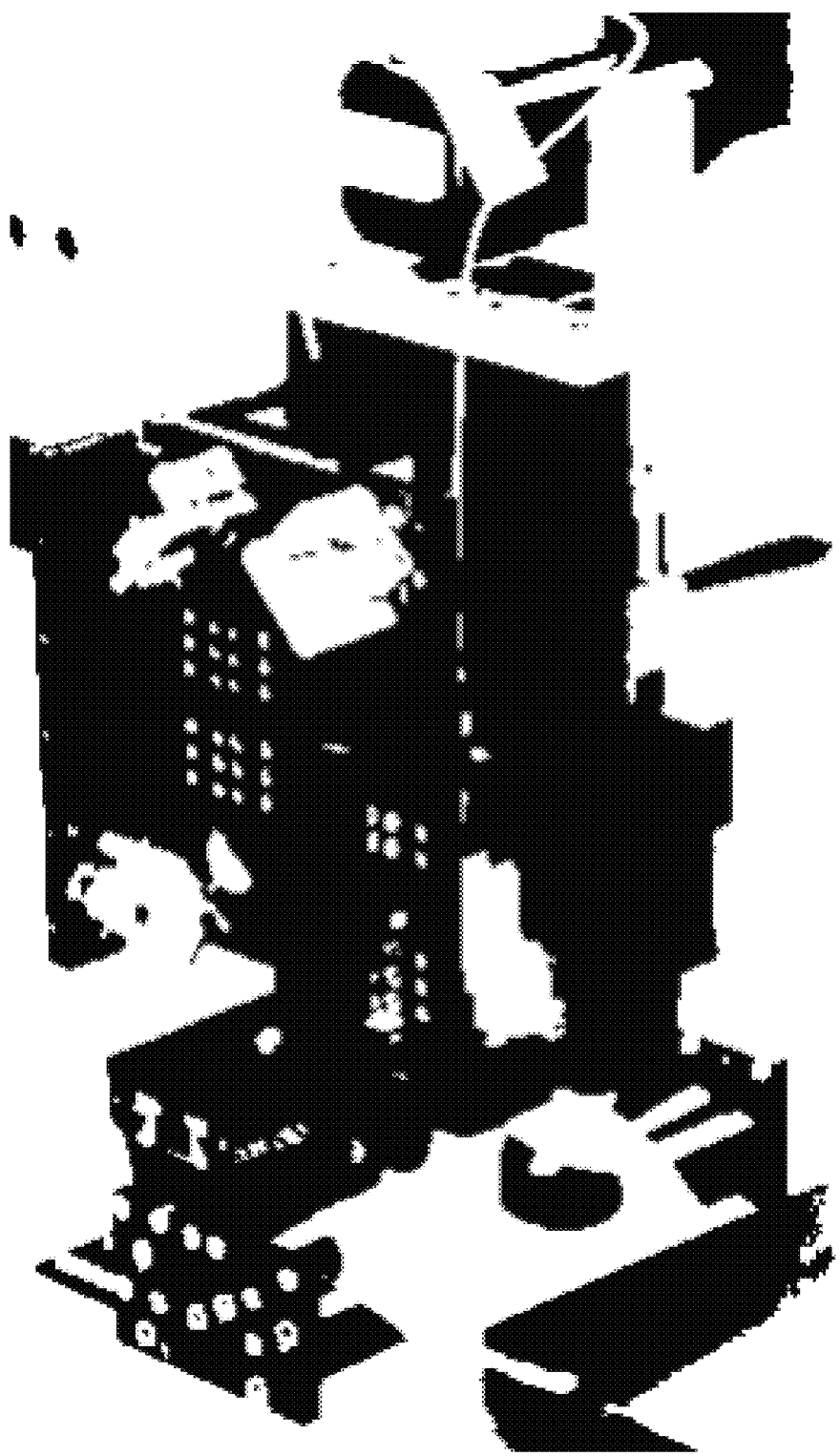
FIG. 10 provides a photograph of an exemplary THz imaging system in accordance with various embodiments.

In accordance with a number of embodiments, the exemplary THz system employed in the various examples and experiments described within generates pulsed THz radiation with a mode locked laser and photoconductive switch, detects the reflected radiation with a waveguide mounted, 0-bias Schottky diode detector, and operates in the frequency band of ~400 GHz-700 GHz (FIG. 10).

In several embodiments, the exemplary reflective THz imaging system employs a photoconductive switch as the source for THz radiation. Photoconductive switches are the most commonly used devices for the generation of broadband THz radiation in a myriad of applications, including THz imaging and spectroscopy (B. Ferguson and X.-C. Zhang, 2002, cited supra; M. Tonouchi, *Nat. Photonics,* 1(2):97-105, 2007; the disclosures of which are incorporated herein by reference). Although not deemed the most powerful of available sources, photoconductive switches demonstrate the highest conversion efficiency amongst conversion and down conversion techniques (K. P. Cheung and D. H. Auston, *Phys. Rev. Lett.,* 55(20):2152, 1985; B. B. Hu, X.-C. Zhang, and D. H. Auston, *Phys. Rev. Lett.,* 67(19):

2709, 1991; M. B. Ketchen, et al., *Appl. Phys. Lett.*, 48(12): 751-53, 1986; M. Y. Frankel, et al., *IEEE Trans. Electron Devices*, 37(12):2493-98, 1990; the disclosures of which are incorporated herein by reference). Numerous embodiments are directed to the use of GaAs as photoconductor, which can be attributed to many improved performance due to its high carrier mobility, high breakdown field, and high resistivity. The addition of a composite film of ErAs particles in the semi-insulating GaAs substrate (ErAs:GaAs), in accordance with multiple embodiments, further decreases the photocarrier lifetime and increase the breakdown voltage as well as provides a high resistivity necessary for THz generation and propagation. In some embodiments, the photoconductive switch is pumped by a 780 nm laser pulse, causing it to take the form of current flowing between the bias pads generated by a bias voltage, and, in turn, gives rise to broadband THz radiation.

Figure 11A:
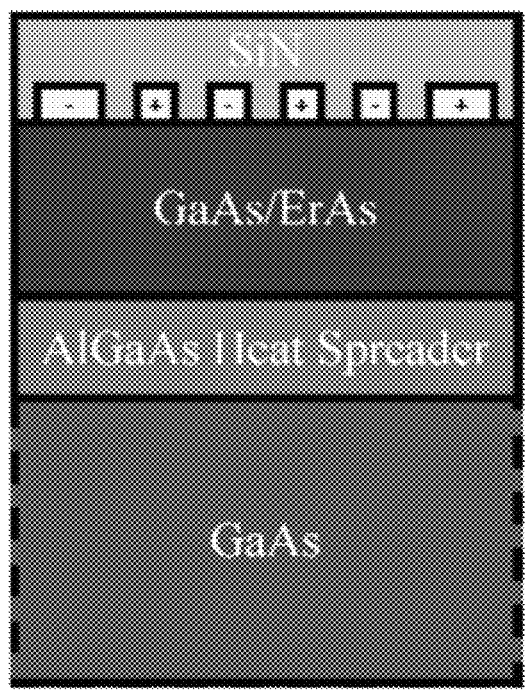
FIGS. 11A and 11B provide (A) material structure of a photoconductive source and (B) a schematic (left) and microscopic image (right) of a spiral antenna patterned atop photoconductive material in accordance with various embodiments.

In accordance with several embodiments, the material structure of the photoconductive switch is shown in FIG. 11A. As shown in this exemplary figure, the switch is grown on a semi-insulating GaAs substrate starting with an AlAs: AlGaAs reflector and an AlAs heat spreader. This is overlaid with a thin photoconductive carrier generation region comprised of a single-crystal ErAs nanoparticles in GaAs via molecular beam epitaxy (MBE). A gold, square spiral antenna and bias pads are patterned atop the active region and capped with silicon nitride to protect the device from oxidation and provide an anti-reflection coating. The antenna structure serves to effectively radiate THz current into free space once it has been generated in the photoconductive gap.

Figure 11B:
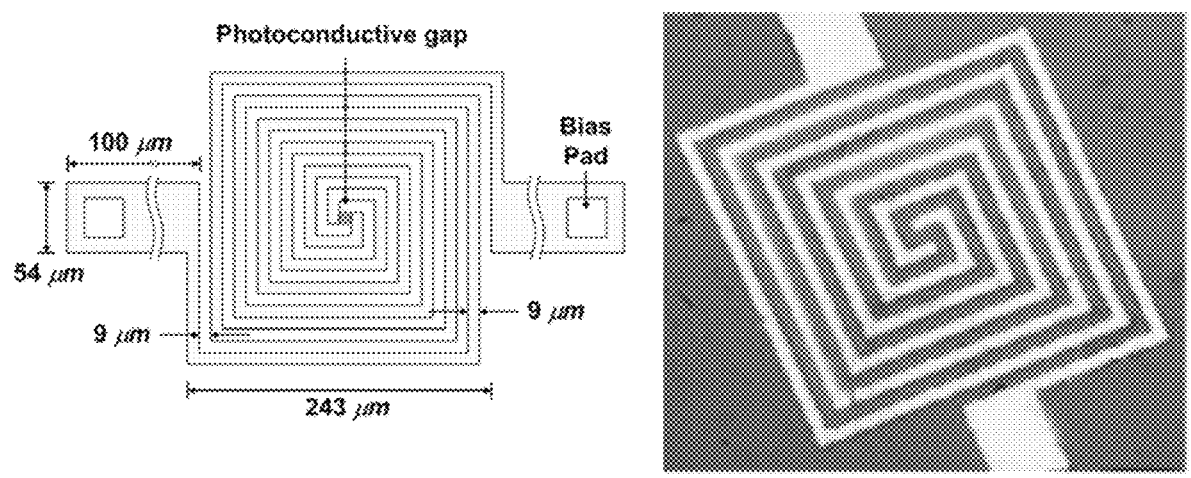

In accordance with more embodiments, the unit cell of the exemplary THz source measures 9 μm×9 μm with a 9 μm gap between each adjacent arm (FIG. 11B). The square spiral acts like a sequence of progressively longer dipoles that results in a high driving point resistance across a large bandwidth and good coupling to the high impedance photoconductive gap. At the termination of the three-turn spiral arms are two bias lines extending 540 μm end to end. The 48 μm width of these lines is wide enough for wire bonding and electrical biasing and has negligible effect on antenna performance. A Golay cell with an optical sensitivity of ~10 mV/μW and a specific optical Noise Equivalent Power (NEP) of ~2×10-10 W/Hz1/2 at a chopped frequency of 16 Hz is used to perform power measurements. At high DC-bias fields (200 V/9 m gap 222 kV/cm) the source produces an optical to quasioptical (THz) conversion efficiency of 1% yielding average powers of up to 46 uW across 1 THz of bandwidth.

The exemplary THz system operates in reflection mode at 0.5 THz with ~125 GHz bandwidth in accordance with even more embodiments. In this exemplary system, the photoconductive switch (PCS) based THz source is pumped by a 780 nm pulse train created by a frequency-doubled 1550 nm mode-locked laser with a 230 fs pulse width and 20 MHz repetition frequency. The PCS is mounted on the back side of a high resistivity silicon hyper-hemisphere for the free-space output. The resulting THz source beam is collimated by a 76.2 mm effective focal length (EFL), 25.4 mm clear aperture off-axis 90° parabolic (OAP) mirror. This system employs a novel THz reflective objective where 2 identical OAP mirrors are mounted such that their clear apertures normal vectors are parallel and their focal spots overlap. This objective takes in a collimated source beam and focuses the THz on target, collects the diverging reflection, and outputs a collimated beam towards the detector optics. A front on view of the geometry used in the exemplary system is the same as displayed in FIG. 6, where $f_m$ is the mirror effective focal length (EFL) and $W_d$ the working distance of the objective assembly. Through clever design and machining the exemplary system, which has a geometry in accordance of the embodiments shown in FIG. 5, is equipped with a THz objective that allows OAPs of varying EFL to be changed without needing to realign the THz beam.

For in vivo THz imaging, in this exemplary system, a 50.8 mm EFL OAP objective mirror at a 14° incidence angle is used to focus the beam onto the target, in accordance with various embodiments. The reflected THz radiation is then collected and collimated by a second 50.8 mm EFL OAP. Finally, a 25.4 mm EFL OAP couples the collected signal to the feedhorn of a WR1.5 waveguide mounted Zero-bias Schottky diode detector (ZBSD). Waveguide mounted, ZBSD are convenient detectors in the THz regime as these devices offer high room temperature responsivity (1000 V/W), low NEP (100 pW/Hz), and extremely broad video bandwidth (1-14 GHz). THz pulses are detected and rectified by the ZBSD. Resulting THz signals are coupled to a gated receiver referenced to split the original optical pulses, that are detected with a 1550-nm high-speed photodiode. The THz imaging system acquires pixel-by-pixel data with a 1 ms integration time. The THz image is generated by raster scanning the region of interest beneath a fixed, focused THz beam using x and y stepper motors. An image with a 6 cm×6 cm FOV and 0.5 mm isotropic resolution can be acquired in ~10 min.

In accordance with multiple embodiments, system characterization studies have shown that this exemplary system architecture yields an effective THz operational band and only requires few optical components. In many embodiments, this simple design minimizes laser alignment and down-converts the THz signal to baseband immediately, rendering the system more robust to misalignment. The overall compact size (12 cm×10 cm×8 cm) of the THz imager and the robust optical layout improves the portability of the system and enables reliable operation in both animal operating suites, and future clinical settings, in accordance with several embodiments.

Optical Characterization and Frequency Analysis of the THz Imaging System

Figure 12:
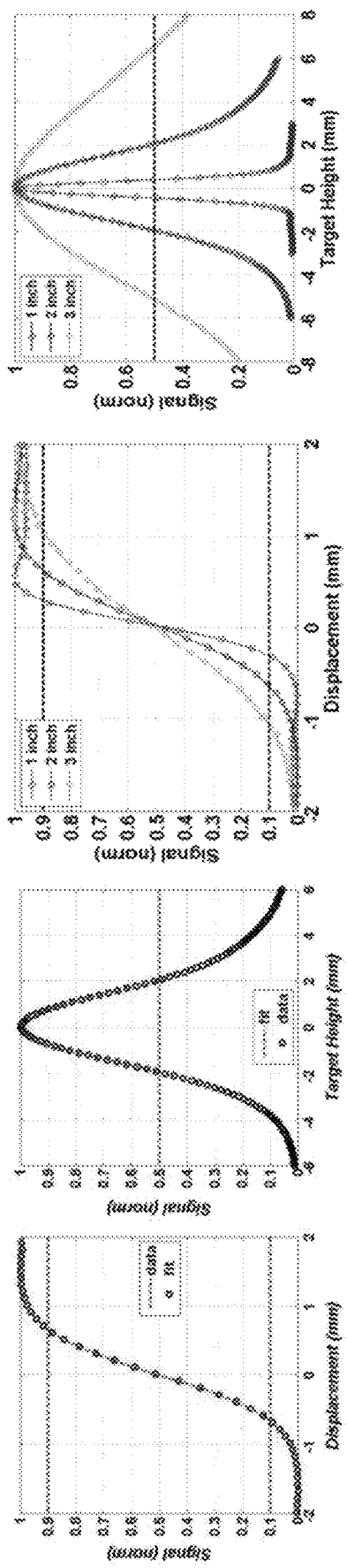
FIG. 12 provides (left) optical characterization of 2" effective focal length (EFL) parabolic mirror and (right) spot size and depth of focus measurements of 1", 2", and 3" EFL off-axis parabolic mirrors (OAPs), generated in accordance with various embodiments.

In accordance with various embodiments spot size and depth of focus measurements of an exemplary 2" focal length mirror (often used in the THz imaging examples herein) and some exemplary EFLs (1", 2", and 3") are displayed on the left and right in FIG. 12, respectively. The spot was measured using a knife edge target with edge swept through the beam (in the x-direction), and is defined with the standard 10-90 edge response criteria. The data follows the fit (dotted line) predicted by the 2D integration of TEM Gaussian beam and yields a 10-90 dimension of 1.1 mm for a 2" EFL mirror. The depth of focus (DOF) was measured by translating a polished metal reflector in and out of the focal plane and the OAP EFLs and measures a total of 4 mm full width at half maximum (FWHM) for a 2" EFL mirror. Superimposed on the data is a Gaussian fit whose shape is predicted by Gaussian beam transverse mode matching. The DOF is limited primarily by the optics of the system and not the pulse multiplication of the receiver. The delay line was manually scanned at the extremum of the DOF sweep and found to have minimal effect on the synchronicity of the rectified THz pulse and reference pulse. Table 2 summarizes the parameters of the 3 OAP THz objectives and their predicted 10%-90% THz spot sizes, in accordance with many embodiments.

TABLE 2

OPTICAL CHARACTERIZATION OF THZ OAPS

| OAP EFL (mm) | $W_d$ | Θ (deg) | 10-90% Spot Size (mm) | DOF (mm) |
|---|---|---|---|---|
| 25.4 | 9.3 | 30 | 0.8 | 0.8 |
| 50.8 | 36.5 | 14 | 1.5 | 4 |
| 76.2 | 62.4 | 9 | 2.5 | 11.7 |

Figure 13:
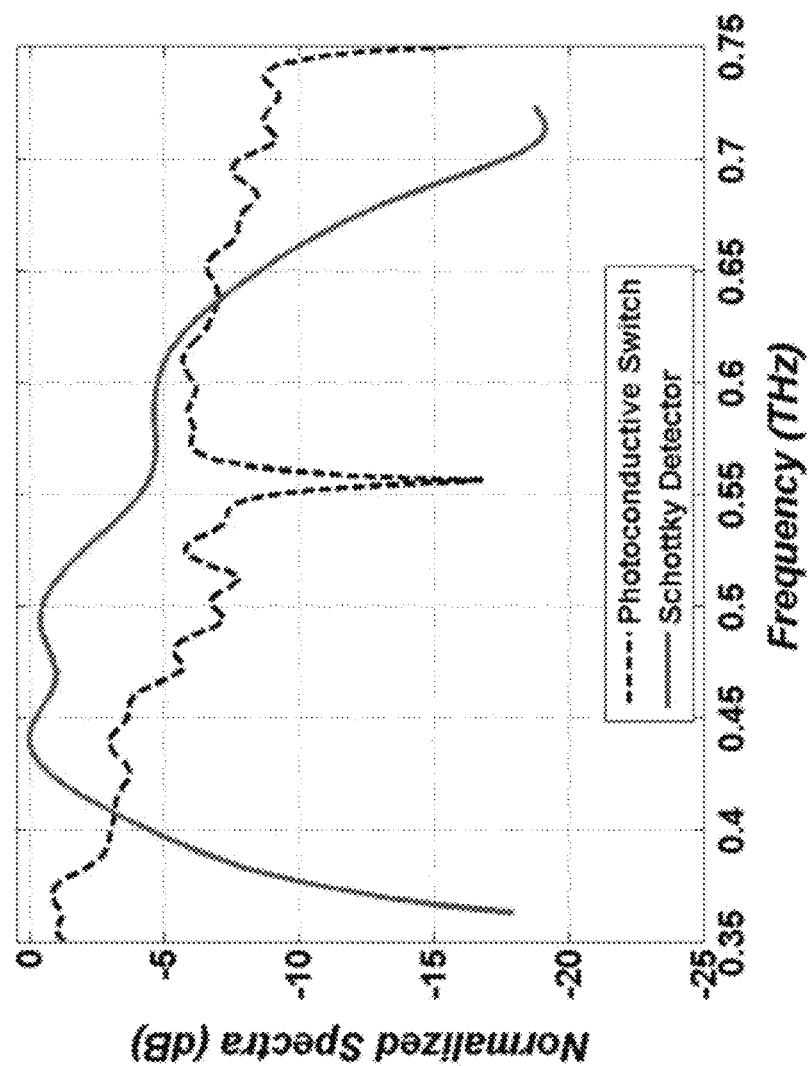
FIG. 13 provides a data graph displaying THz imaging system spectra where the dotted line is the normalized photoconductive switch power spectral density and the solid line is the Schottky diode normalized spectral responsivity, generated in accordance of various embodiments; the response peaks at 440 GHz and the total width reflects the operation band of a WR1.5 waveguide.

In several embodiments, the effective center frequency and bandwidth of the system are constrained by the switch power spectral density (PSD) the detector spectral responsivity. The normalized power spectral density of the photoconductive switch is displayed in FIG. 13 superimposed on the normalized Schottky diode spectral responsivity. The switch spectrum was acquired with a Fourier Transform Infrared (FTIR) spectrometer and He-cooled composite bolometer. The detector spectral responsivity was measured with a THz photomixing setup. A center frequency of 525 GHz with 125 GHz of 3 dB bandwidth is observed, and utilized in many embodiments. This bandwidth is sufficient to overcome speckle from standing waves between the source and detector as well as provides sensitivity to changes in water concentration and good spatial resolution, in accordance with several embodiments.

Dielectric Window Selection

Figure 14:
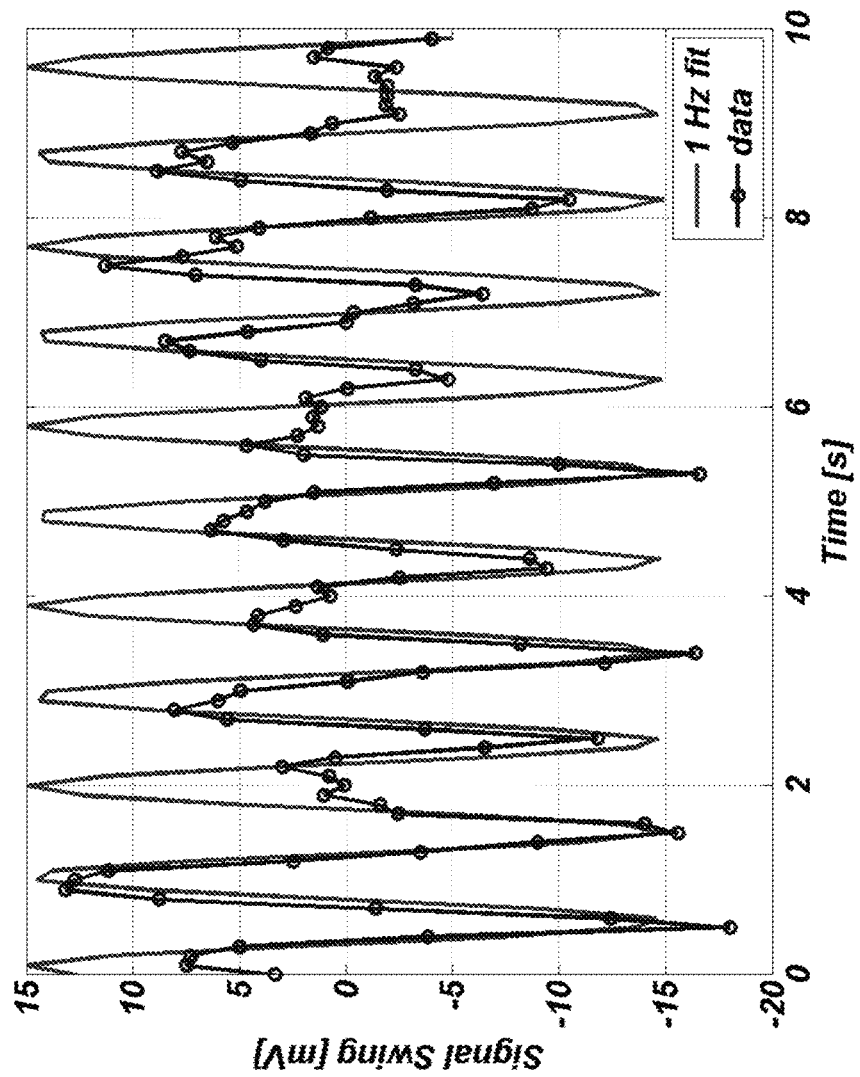
FIG. 14 provides a data graph displaying signal swing in relation to time, which demonstrated thin flexible windows provide significant motion artifacts for time domain systems, generated in accordance with various embodiments.

Although windowless burn wound assessment may be preferred, in accordance with many embodiments, windows can be utilized in THz imaging to minimize confounding effects from surface roughness, non-planar geometries, and respiratory motion artifacts in vivo (A. Wagner-Gentner, et al. *Infrared Phys. Technol.*, 48(3):249-53, 2006; H. Hoshina, et al. *Appl. Phys. Lett.*, 94(12):123901, 2009; the disclosures of which are incorporated herein by reference). Both high and low dielectric substrates, including quartz, sapphire, and thin stretched Mylar film, can be used to flatten the imaging target in accordance with various embodiments (Z. D. Taylor, et al., *Terahertz Sci. Technol. IEEE Trans. On*, 1(1)201-19, 2011; V. P. Wallace, et al., "*Appl. Spectrosc.*, 60(10): 1127-33, 2006; B. E. Cole, et al., *Photonics West* 2001-LASE, pp. 1-10 2001; A. J. Fitzgerald, et al., *Radiology*, 239(2):533-40, 2006; M. Sajadi, M. Wolf, and T. Kampfrath, *Opt. Express*, 23(22):28985-28992, 2015; B. Ung, et al., *JOSA B*, 28(4):917-21, 2011; the disclosures of which are incorporated herein by reference). As shown in FIG. 14, slight perturbations in THz signal are evident even with window-driven motion correction. In addition, the thickness of windows contributes substantially to the overall observed electromagnetic properties of the target of interest. Consequently, the distribution of water along the coronal axis (both in the thickness of tissue layers and the layer composition) alters the tissue's reflectivity.

Figure 15:
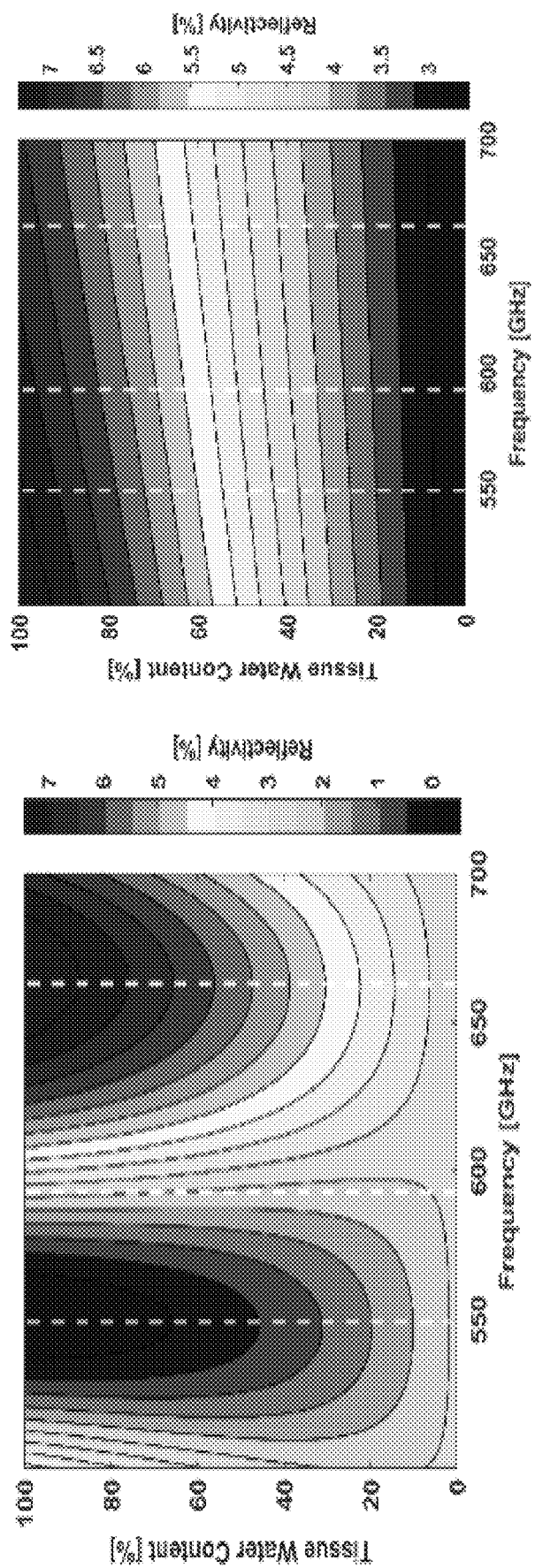
FIG. 15 provides electromagnetic models of dielectric substrates (left) thick Mylar of 500 μm and (right) thin Mylar of 12 μm, utilized in accordance with various embodiments.

As an example, two cases were considered: a 500 μm thick Mylar window and a 12 μm thick Mylar window (FIG. 15). Electromagnetic modeling predicted that the power reflectivity of a tissue system under thick Mylar illuminated at a 14° incidence angle was frequency-dependent, and, therefore, varied non-linearly with respect to increasing tissue water content.

In other words, over the aforementioned frequency range, reflectance may vary from high-to-low or high-to-low-to-high with increasing tissue water content. Conversely, in the case of thin Mylar, a positive correlation was suggested between increases in TWC and THz reflectivity. Given that implementation of an optical window is currently necessary in THz burn imaging, a 12 μm Mylar was selected to enable more predictable electromagnetic modeling behavior for in vivo burn imaging. Accordingly, various embodiments utilize a thin dielectric window and other embodiments utilize a thick window to achieve the desired properties.

Example 2: Electromagnetic Model and Expected Behavior of Burn Wounds

Various prior art has commented on the accuracy of using the double Debye model as a baseline and perturbing the relaxation time until the fit converges with the observed spectra (D. B. Bennett, et al., *IEEE Sens. J.*, 11(5):1253-62, 2011; H. J. Liebe, G. A. Hufford, and T. Manabe, "*Int. J. Infrared Millim. Waves*, 12(7):659-75, 1991; E. Pickwell, et al., *Appl. Phys. Lett.*, 84(12):2190-92, 2004; Z. D. Taylor, et al., *IEEE Trans. Terahertz Sci. Technol.*, 5(2):170-83, 2015; A. Maccabi, et al., 8585:85850X-85850X-, 2013; the disclosures of which are incorporated herein by reference). Here, in accordance with various embodiments, it is proposed to employ effective media theory to compute tissue dielectric properties through the use of the estimated fill factor of water to tissue. When the tissue water content is changed by thermal insult and the subsequent physiologic response, the fill factor can be modified to compute the effective dielectric function at the tissue hydration of interest. This methodology models what is thought to occur in burn wounds and serves as a good starting point when performing system design calculations for expected reflectivity, sensitivity, etc. The methodology for simulating the frequency dependent aggregate properties of skin has been presented in prior publications (Z. D. Taylor et al., 2011, cited supra; E. Pickwell, et al., 2004, cited supra; M. Ney and I. Abdulhalim, *J. Biomed. Opt.*, 16(6):67006, 2011; the disclosures of which are incorporated herein by reference). A brief summary of this method is provided below.

Summary of Model

The frequency dependent dielectric properties of water are captured by the Double Debye model (EQ. 3) with the constitutive parameters and corner frequencies ($\varepsilon_0$, $\varepsilon_1$, $f_1$, $f_2$).

$$\varepsilon_w(f) = \varepsilon_\infty + \frac{\varepsilon_0 - \varepsilon_1}{1 - j2\pi f/f_1} + \frac{\varepsilon_1 - \varepsilon_\infty}{1 - j2\pi f/f_2} \qquad \text{EQ. 3}$$

As mentioned previously, the skin is composed entirely of collagen and water which allows the implementation of a binary mixture Bruggeman model (EQ. 4) where Ebb is the frequency invariant dielectric constant of the non-water tissue constituents termed biologic background (bb), $\varepsilon_w$ is the frequency dependent dielectric constant computed with (EQ. 3), $p_w$ is the water volume fraction, and $\hat{\varepsilon}$ is the effective permittivity of the layer that satisfies the equivalence relation in (EQ. 4). The water volume fractions can be adjusted to match any hypothesized distribution. Further, when tissue water content is perturbed by thermal insult and subsequent physiologic response, the fill factors can be modified to compute the change in dielectric function and overall expected change in THz reflectivity.

$$\hat{\varepsilon} \text{ s.t. } p_w\left(\frac{\hat{\varepsilon} - \varepsilon_w}{\varepsilon_w + 2\hat{\varepsilon}}\right) + (1 - p_w)\left(\frac{\hat{\varepsilon} - \varepsilon_{bb}}{\varepsilon_{bb} + 2\hat{\varepsilon}}\right) = 0 \qquad \text{EQ. 4}$$

Figure 16:
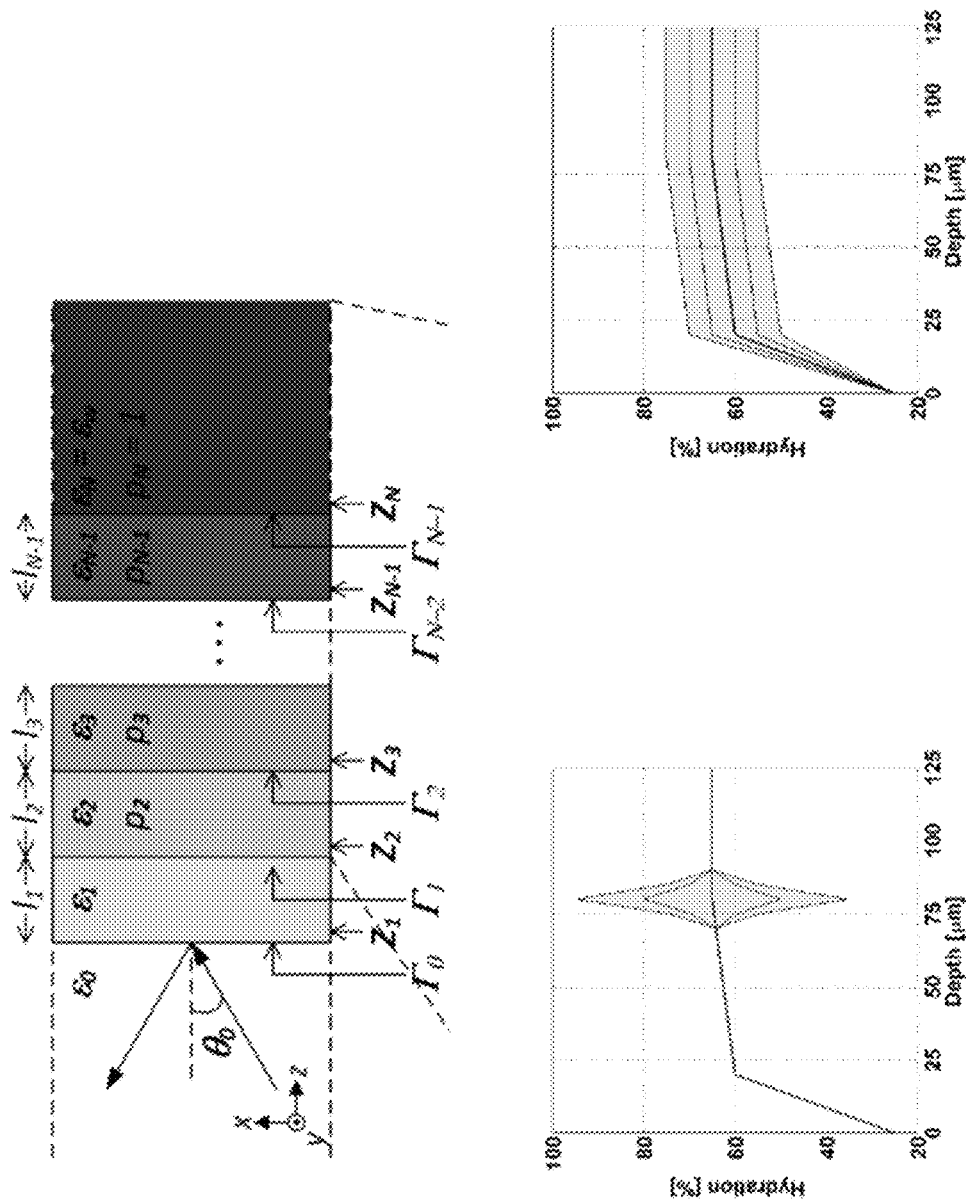
FIG. 16 provides a schematic of the effective media model and TWC perturbations, utilized in accordance of various embodiments.

In accordance with various embodiments, the stratified media and effective media methodologies used to simulate the THz frequency properties of skin are shown in FIG. 16. To illustrate the variability of the skin electromagnetic properties, two candidate variation types were explored. FIG. 16 (bottom-left panel) contains an example of a localized TWC perturbation where the edema occurs primarily at the epidermis/dermis interface. FIG. 16 (bottom-right panel) shows an example of global variation with fixed surface hydration where the edema penetrates all the skin layers but the top surface remains intact.

While researchers have hypothesized that burn wound edema is expressed in some layers more strongly than others, there is a general consensus that the TWC of all layers are effected to some degree (R. H. Demling, 2005, cited supra; R. H. Demling, 1982, cited supra; T. Lund, H. Onarheim, and R. K. Reed, *World J. Surg.*, 16(1):2-9, 1992; the disclosures of which are incorporated herein by reference). This notion suggests that burn wounds experience perturbations that are some combination of the distributions in FIG. 16. The effective electrical length of the layer i is written (EQ. 5) where is the complex, effective permittivity of layer i computed with (6) and θi is the complex angle of refraction computed with Snell's law.

$$\delta_i = \frac{2\pi}{\lambda} l_i \sqrt{\hat{\varepsilon}_i} \cos(\theta_i) \quad \text{EQ. 5}$$

For the simulations presented below the discretized layer thickness was set at ~10 μm where reflectivity simulation results with varying layer thicknesses converged to a differential less than 10-3. Thinner layers results in insignificant increases in accuracy at the expense of increases in computational complexity.

$$\rho_i = \frac{\sqrt{\hat{\varepsilon}_{i-1}} \cos(\theta_{i-1}) - \sqrt{\hat{\varepsilon}_i} \cos(\theta_i)}{\sqrt{\hat{\varepsilon}_{i-1}} \cos(\theta_{i-1}) + \sqrt{\hat{\varepsilon}_i} \cos(\theta_i)} \quad \text{EQ. 6}$$

$$\Gamma_i = \frac{\rho_i + \Gamma_{i+1} e^{-j2\delta_i}}{1 + \rho_i \Gamma_{i+1} e^{-j2\delta_i}} \text{ where } \Gamma_N = \rho_N \quad \text{EQ. 7}$$

The Fresnel reflection coefficient from layer i−1 to layer i each interface can be written as a function of the complex effective dielectric constants and the complex refractive indexes. Note that the Fresnel coefficient has been written for TE polarization. This polarization has been shown to produce reflectivities and hydration sensitivities larger than the TM polarization for any incidence angle. The total aggregate electric field Γ reflection coefficient from layer i+1 to N is given in (EQ. 7) where $\Gamma_N$ is defined as the Fresnel coefficient between the final layer of the stratum corneum and dermis and $\Gamma_0$ is the total reflection coefficient of the window covered burn wound.

For the analysis, two different quantities as a function of hydration and frequency were computed; the expected reflectivity of the burn wound (EQ. 8) and the expected change in reflectivity per change in hydration (EQ. 9).

$$\text{Power reflectivity} = \mathcal{R} = |\Gamma_0|^2 \quad \text{EQ. 8}$$

$$\text{Hydration Sensitivity} = \Delta H = \left|\frac{d\mathcal{R}}{dp}\right| \quad \text{EQ. 9}$$

Although significant research has been undertaken to understand the physiology of burn wounds, the depth dependent tissue hydration of burns throughout the healing process are not entirely known. This is due in part to the lack of imaging tools that are sensitive to hydration.

Simulations of the computed reflectivity over the system operational band have been performed in accordance with various embodiments. The key difference observed is that the global perturbation displays a positive correlation between TWC increase and THz reflectivity while the localized perturbation displays areas of positive and negative increase. In other words, increasing TWC at a particular depth can lead to a decrease in THz reflectivity, which is a phenomena utilized in various embodiments described within.

Example 3: THz In Vivo Imaging in Pre-Clinical Rat Model

To test various embodiments of the invention, rats were used as an pre-clinical model for in vivo THz burn wound imaging (W. A. Dorsett-Martin, Wound Repair Regen., 12(6):591-99, 2004, the disclosure of which is incorporated herein by reference). Among the available burn wound parameters, skin thickness is most pertinent for understanding the wound depth as an aspect of wound healing. The thicknesses of rat and human skin layers are most similar compared to those of other animal skin (Table 3), and therefore rats are frequently used as cutaneous injury models (T. N. Meyer and A. L. da Silva, "*Acta Cirúrgica Bras.,* 14(4):0-0, 1999; R. K. Cribbs, M. H. Luquette, and G. E. Besner, *J. Surg. Res.,* 80(1):69-74, 1998; T. Kaufman, et al., *Burns,* 16(1):13-16, 1990; J. S. Knabl, et al., *Burns,* 25(3): 229-35, 1999; the disclosures of which are incorporated herein by reference). In addition to the availability of a broad knowledge base on rat wound healing, rats are readily available, inexpensive, and easy to manage. Lastly, large numbers of these pre-clinical models can be used to achieve statistically significant measurements.

TABLE 3

HUMAN AND ANIMAL SKIN THICKNESS MEASUREMENTS

| Type of Skin | Stratum Corneum (μm) | Epidermis (μm) | Whole Skin (mm) |
| --- | --- | --- | --- |
| Human | 16.8 ± 0.7 | 46.9 ± 2.3 | 2.97 ± 0.28 |
| Pig | 26.4 ± 0.4 | 65.8 ± 1.8 | 3.43 ± 0.05 |
| Rat | 18.4 ± 0.5 | 32.1 ± 1.3 | 2.09 ± 0.07 |
| Hairless mouse | 8.9 ± 0.4 | 28.6 ± 0.9 | 0.70 ± 0.02 |
| Mouse | 5.8 ± 0.3 | 12.6 ± 0.8 | 0.84 ± 0.02 |

In accordance with various embodiments, a 12.7 μm Mylar window suspended from a brass frame was lowered onto the shaved abdomen of anesthetized rats to flatten the imaging field. The THz reflectivity was maximized off animal's skin for every individual. Visible images of the uninjured abdomen were captured with a SLR camera and control scans covering a 2.5×2.5 cm field of view (FOV) were initiated with the THz imaging system. Image acquisition time was estimated to be ~10 minutes. The window was then removed, and a 2 mm×19 mm rectangular brass brand secured to a thermocouple—to accurately monitor the absolute temperature—was heated to 200° C. and 130° C. using a hot plate, positioned between the three black circular dots on the abdomen, and manually applied with a constant pressure for 10 seconds to induce a full thickness and partial thickness burn, respectively. 5 rats received partial thickness wounds, and the remaining 5 rats received full thickness burn wounds. The Mylar window was repositioned on the burn and concomitant visible and THz imagery were continuously acquired every 15 min for the first hour and every 30 min for the remaining 7 hrs. The Mylar window was kept stationary during continuous scanning to remove any discrepancies in z settings arising from removing the window between scans. Upon scan completion, the rat was awoken and returned to the vivarium in care fresh bedding to ensure minimum discomfort to the wound. An antibiotic, Trimethoprim-Sulfamethoxazole, was administered orally to prevent possible infection ensuing burn injury. Follow up visible and THz imagery were acquired at 24 hr, 48 hr and 72 hr post burn induction, at which point the animal was euthanized.

Three sections of skin along the rostrocaudal axis were harvested from the left, center and right regions of the burn and transferred to 10% formalin solution; these tissue specimens contained both uninjured and injured tissue, providing a control area which the burned area could be compared to. The skin samples were then submitted for histological embedding, sectioning (8 μm thickness), and staining with hematoxylin and eosin (H&E). Light microscopy was used to examine the burn slices, followed by analysis of the observed structural tissue damage to assign burn severity.

In accordance with multiple embodiments, external fiducial markers were used to align THz images to their respective visible pictures. Two triangular painter's tape pieces positioned on diametrically opposite sides of the brass frame of the Mylar window served as fiducial markers. The triangles were visible in the THz image and visible picture acquired prior to the THz scan. Additionally, the markers on the visible picture were aligned with the corresponding view on the THz images with respect to location and size of the markers. Because the Mylar window was kept stationary during continuous scanning, all THz images are registered to one another during the 7 hr period. Interpatient registration was performed by selecting the center of the burn to be the intrinsic fiducial marker. Setting the center as the point of origin, THz images across all rats were rotated and translated to line up in the same orientation.

Figure 17:
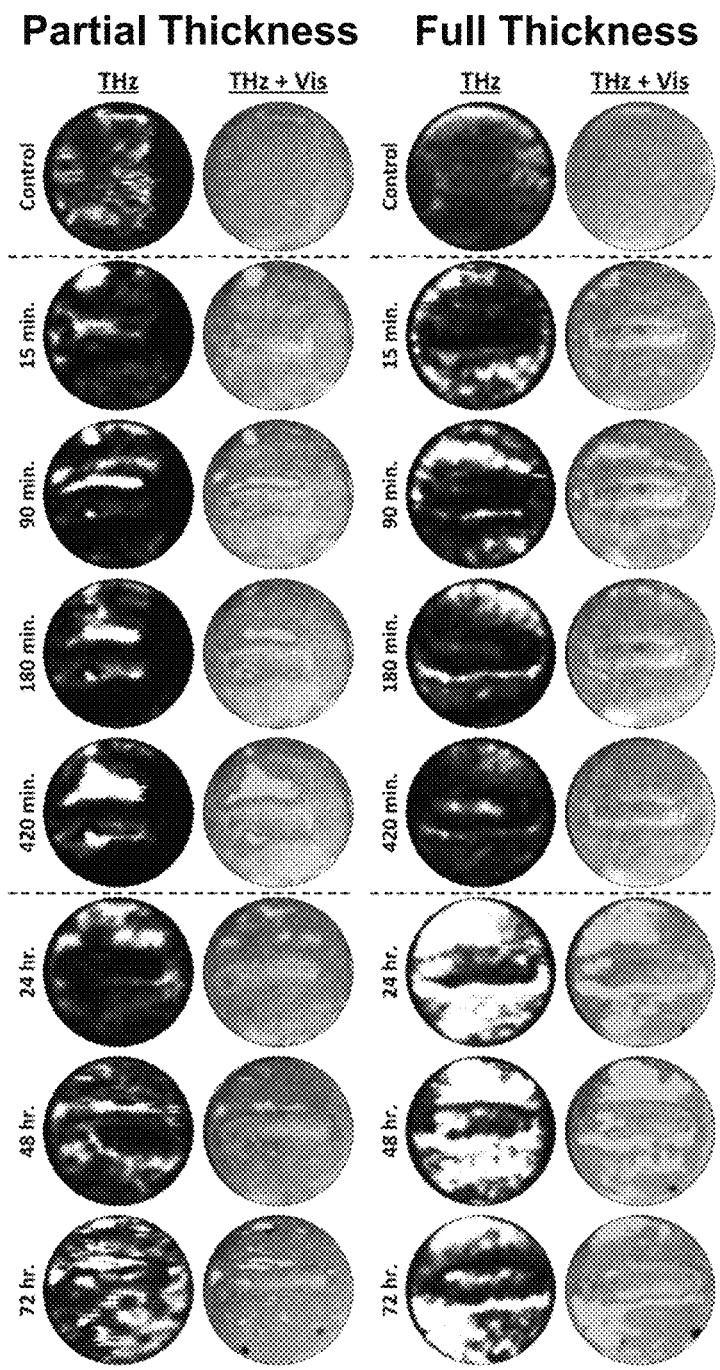
FIG. 17 provides a panel of time series THz imagery of partial and full thickness burns, generated in accordance of various embodiments; the left images are a hot color map and the right images are superimposed THz/Visible imagery.

As shown in FIG. 17, in accordance with various embodiments, burn wounds were imaged under a thin film Mylar window, and THz images and superimposed THz-Visible images were generated using a hot color map and cyan color scale, respectively. The hot color map transforms black to the global minimum THz reflectivity and white to the global maximum THz reflectivity for all burns, and the cyan color map denotes tissue edema. With respect to the THz imaging observations, various embodiments are directed to the positive correlation between water concentration increase and THz reflectivity suggested by stratified media and effective media modeling of a global perturbation in tissue water content under a thin film Mylar window. More embodiments are also directed to the dominant contrast mechanism of THz imaging was TWC.

Following burn induction, partial thickness burns demonstrate a TWC variation within the contact area and low level desiccation in the surrounding tissue while full thickness burns undergo an overall increase in surrounding TWC and the contact region experiences a noticeable drop in TWC. High TWC levels can be ascribed to previously reported TWC increases of up to 75% in the burned tissue compared to uninjured skin that occur 30 minutes post injury. The rapid image acquisition time (~10 minutes) of THz imaging is on the same order as burn pathophysiology, and therefore enables the visualization of these immediate post burn events.

Upon visual inspection of THz imagery in FIG. 17, two features are evident at the wound center: a central area enveloped by a thin annulus. These image features are first apparent by the 1.5 hr mark and are starkly visible in full thickness burns and much less visible, but still present, in partial thickness wounds. TWC of the annulus, in particular, is consistently low for longitudinal THz burn imagery in both partial and full thickness burns. The zone of stasis—the intermediate region between the central zone of devitalized tissue and the outermost zone of hyperemia—is similarly known to be characterized by low perfusion, and therefore it is strongly hypothesized that this ring of low TWC to correspond to this zone.

FIG. 17 displays the central wound area varies with wound severity. From 1.5 hours up to 7 hours post induction, partial thickness injuries demonstrate significant reduction of TWC in the central contact area and a significant yet somewhat localized increase in TWC in the adjacent regions. Full thickness burns also initially display increases in TWC in the adjacent tissue, however the effect is less localized and instead appears to fill the entire FOV. Furthermore, the central contact area of a full thickness wound begins to fill in and approach the TWC of the adjacent tissues. By Days 1-3, fluid redistribution resurfaces in THz imagery of both a partial and full thickness burn wound. This resorption of fluid begins ~24 hours post injury and may be responsible for the reduced contrast observed at Day 3 in the partial thickness wound. Accordingly, several embodiments utilize THz-derived data to assess wound edema status.

To explore the spatial information contained in the imaging data sets, features inspired by burn wound physiology were identified and classifiers based on these features were used to delineate between burn severity groups. Burn pathophysiology is commonly characterized by three typically concentric regions; the zones of coagulation, stasis, and hyperemia, and each is representative of tissue viability. The innermost region (coagulation) contains irreversibly damaged cells and depending on the severity of injury and damage to the vasculature. This is surrounded by the zone of stasis which is characterized by mixed viability tissue and the zone of hyperemia which contains affected but likely salvageable tissue. Accompanying these zones are local and systemic fluid shifts, with water concentrations that may vary by up to 80% within 10 minutes of the injury. Accordingly, embodiments are directed to utilizing THz imaging data to identify burn pathophysiology (i.e., the zones of coagulation, stasis, and hyperemia) and diagnose tissue viability. In some of these embodiments, tissue viability diagnosis occurs within an hour of injury. In more embodiments, tissue viability diagnosis occurs within ten minutes of injury.

Figure 18:
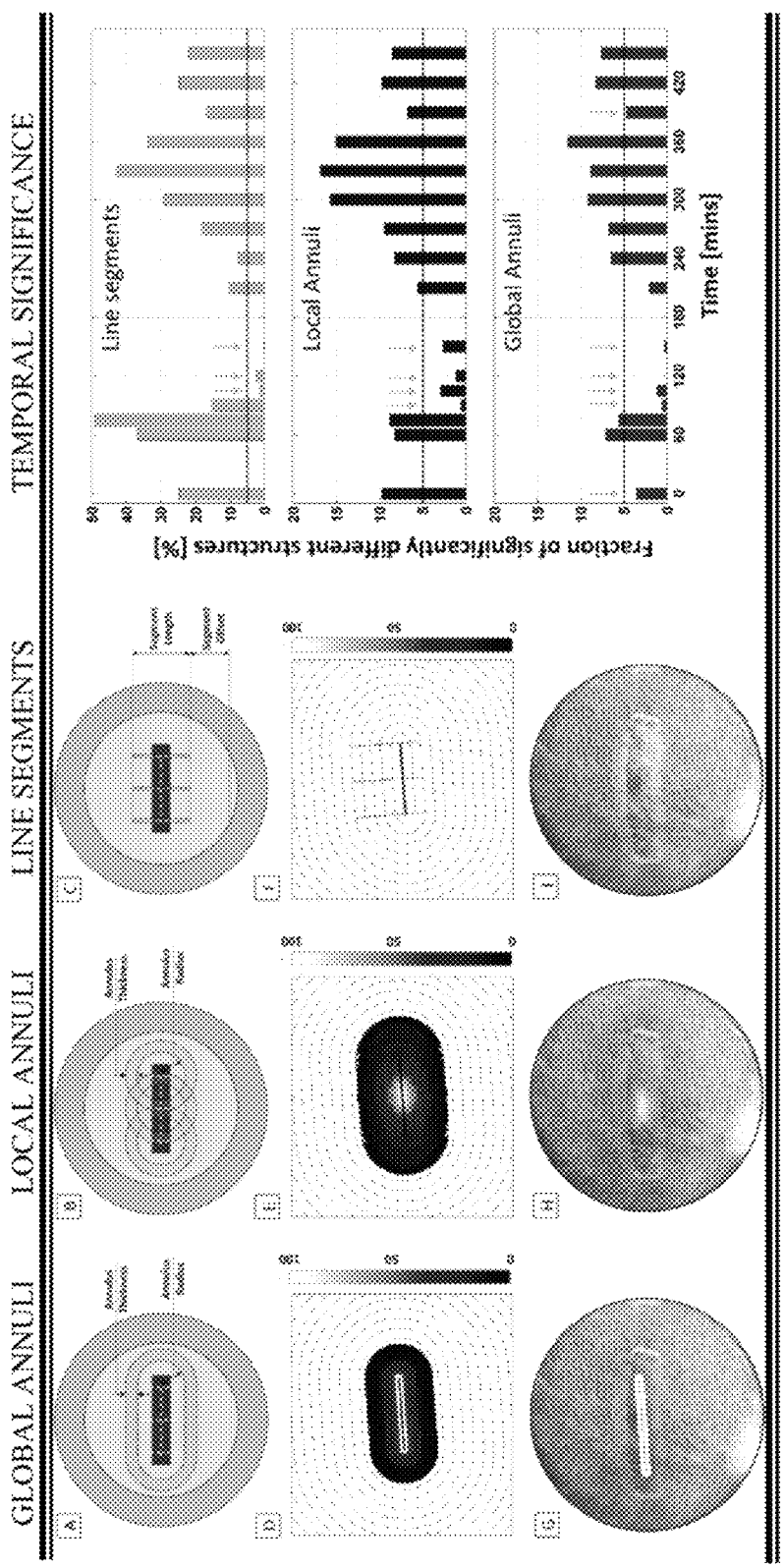
FIG. 18 provides image segmentation for global annuli, local annuli, and line segments for a partial and full thickness burn wound on Day 0; spatial significance, where the number of times a pixel was included in a statistically significant feature is converted to a percentage; also provided is temporal significance of the fraction of significantly different structures that pass a 5% false discovery rate; each of which is generated in accordance with various embodiments.

To leverage this knowledge of physiology, features consisting of orthogonal line cuts (collinear with the location tissue was harvested from for histology) and local and global annuli of constant distance from the wound center were analyzed and a classification function looking at the variation in reflectivity as the length and radius of the lines and annuli was increased was evaluated. After intermodality registration (THz image to visible), intersubject registration (animal to animal), and intrasubject registration (within the same animal) was performed, temporal and spatial significance of the different segmentation methods was performed. As shown in FIG. 18, for global and local annuli segmentation, the center of the wound is spatially significant between a partial and full thickness wound. For orthogonal line segments across a partial thickness and full thickness wound, the bottom of the wound is statistically significant. For all segmentation methods, the temporal significance of the fraction of significantly different structures that pass a 5% false discovery rate is observed within the first 2 hours following burn induction and after 4 hr.

Example 4: In Vivo Reflective THz Imaging of Burn-Induced Edema Correlated with MRI The potential of THz imaging for edema assessment by correlating THz frequency tissue reflectivity measurements with relative proton density measurements captured by $T_2w$ MRI in burn-induced edema models was investigated. It is important to note that MRI is only used here for pre-clinical research purposes, as its cost and limited portability make it inappropriate for TWC characterization in patients, especially critical patients. Burn wounds in rats are known to severely and acutely perturb TWC and, thus, were selected as the model for this correlative study. Partial thickness burns and full thickness burns were induced in vivo to the abdominal skin of rats using an established contact wound protocol that exhibits markedly different TWC perturbations corresponding to burn severity, as detailed in Example 3. Partial thickness, or 2nd degree, burns involve the epidermis and dermis to reticular dermis skin layer (D. Heimbach, et al., *World J. Surg.*, 16(1):10-15, 1992, the disclosure of which is incorporated herein by reference). Full thickness, or 3rd degree, burns involve the whole thickness of the skin and possibly subcutaneous tissue.

Concomitant THz and MRI images of both burn models were acquired with a reflective THz system and 7T MRI prior to thermal insult, 90 min, 210 min, and 270 min following burn induction. In accordance with various embodiments, THz wound imaging has shown that partial thickness and full thickness burns produce pronounced and distinct spatiotemporal changes in THz image contrast (See Example 3). Therefore, similar to THz imaging, it is hypothesized that MRI TWC-based contrast would: I) exhibit unique signal characteristics for each wound model; and II) agree with trends observed in the companion THz burn imagery.

Following histological assessment of burn severity in each wound model, a one-to-multiple cross-correlation across time was performed between THz and depth-dependent MRI imaging, respectively; at all time points, a single reflectivity measurement across the burn region in the THz image was compared to relative proton density measurements performed at multiple burn depths in the companion MRI image to: I) investigate mobile TWC (i.e. edema) as the underlying biophysical driver of observed changes in THz reflectivity and II) quantify in vivo the tissue depths at which THz imaging can potentially probe edema; in accordance with various embodiments.

Materials & Methods
  Injury-Induced Cutaneous Edema:
  All experiments were approved by the Institutional Animal Care and Use Committee (IACUC). Two male Sprague Dawley rats weighing 180-200 g (Harlan laboratories, Hayward, Calif.) were used as preclinical models to investigate the effects of burn-induced edema on reflective THz imaging contrast.

Surgical preparation of the rats began with administration of extrinsic intradermal fiducial markers to allow for image registration between the THz images, visible images, and histology. 72 h prior to burn induction, each rat was anesthetized using isoflurane (4% and 1% for induction and maintenance, respectively), the skin from the abdomen was shaved to expose a 5 cm×5 cm area of bare skin, and three tattoos were applied to the abdomen; intradermal injections of non-metallic green ink were administered via a sterile 28G needle to form the apices of a right triangle. Once tattooed, both subjects were awoken and allowed to recover for 72 hr.

THz and MRI Imaging Systems:
A 7T small bore MRI scanner (Bruker Biospin, Switzerland) was used to acquire MR imagery of in vivo burns (N. Bajwa, et al., *Proc SPIE* 8496:84960X-84960X-7, 2012, the disclosure of which is incorporated herein by reference). To obtain high-resolution images a 160 mm gradient was used to achieve a pixel size of 86 microns in depth in combination with a small surface radiofrequency coil (3 cm in diameter) to improve the signal-to-noise ratio (SNR). High-resolution $T_2w$ multislice multiecho (MSME) MR images of abdominal skin prior to and following burn induction were obtained by varying TE (TR=500 ms, eight TE values including 14, 28, 42, 56, 70, 84, 98, and 112 ms) within a 44×11 mm2 field of view (FOV) and a slice thickness of 2 mm, corresponding to a voxel dimension of 172×86×2000 μm$^3$. A total stack of six axially oriented MRI slices required an image acquisition time of ~40 min. The aforementioned protocol has previously been used to acquire spatially resolved imagery of ex vivo skin burns with high contrast and SNR (N. Bajwa, et al., 2012, cited supra).

A reflective THz imaging system was used to acquire THz images of uninjured skin and burn tissue. In this example, the exemplary THz system operates in reflection mode at a center frequency of 0.525 THz with ~125 GHz bandwidth. The effective center frequency and bandwidth of the system are constrained by the THz source's power spectral density and the detector's spectral responsivity. In accordance with many embodiments, this bandwidth is sufficient to overcome speckle and is sensitive to changes in tissue water content with good spatial resolution. The system consists of a photoconductive switch based THz emitter, Schottky diode detector, and a novel gated receiver for high SNR, high dynamic range measurements of THz power. The Schottky diode detector is mounted in a 0.381×0.1905 mm rectangular waveguide (WR1.5) to limit the system detection to the 400 GHz-700 GHz band. These spectral parameters are chosen in accordance with various embodiments to balance TWC sensitivity and sufficient spatial resolution, while mitigating clutter in the acquired image. The THz beam is handled by quasi-optical imaging system that focuses the radiation to a 1 mm$^2$ diameter spot at a 36 mm standoff distance. THz imagery was generated by raster scanning the imaging subject beneath the fixed, focused THz beam at a 1 ms per-pixel integration time. An image with a 60 mm×60 mm FOV required a scanning time of ~10 min using a 0.5 mm step size.

On the day of the burn study, visible and THz images of the uninjured, tattooed abdominal skin of anesthetized rats in supine position were captured with an SLR camera and the THz imaging system. In comparison, control scans of the animal in prone position were acquired using a $T_2w$ MSME sequence with the 7T animal instrument. A 12 μm thick optical Mylar window (~3.1 cm in diameter), transparent to THz illumination, was lowered onto the abdominal skin during THz imaging to flatten the imaging plane and minimize effects from non-uniform surface contours.

Before MRI imaging, the Mylar window was removed and two 0.75 cm MRI fiducial markers (Radiance filled Ortho-SPOT Packets, Beekley Medical, Bristol, Conn.) were positioned superior and inferior to the designated burn induction area and a visible image was acquired. The rat was then placed on the surface coil in prone position for MRI scanning of the uninjured skin; this positioning of the coil on the abdominal skin increased the SNR.

Upon completion of the control scans, a full thickness and partial thickness burn were induced on the rat abdomens. A 2 mm×19 mm rectangular brass brand was secured to a thermocouple (OMEGA, Stamford, Conn.) to accurately monitor the absolute temperature of the brand. The brand was heated to 200° C. and 130° C. using a hot plate, positioned between the fiducial markers using a high-precision manual z-stage, and applied to the abdomen with a constant pressure for 10 s to induce a full thickness and partial thickness burn, respectively. Each rat received one burn to minimize the total burned body surface area, thus reducing effects of shock on the physiologic wound response.

Visible and THz imaging of a burn region covered a 60 mm×60 mm FOV. THz images only include tissue under the Mylar window, and this measures 11.4 cm2. MRI covered a registered volume of 44 mm×11 mm×92 mm. Parallel THz and MRI imagery were acquired continuously over a 5 h period. The rats were then returned to the vivarium and euthanized 3 days following burn induction because the final status of a burn wound typically manifests 72 h following thermal insult.

It is important to clarify the kind and spatial dimension of information captured in a THz image of tissue versus that in a MRI image of the same specimen. In accordance with various embodiments, THz imaging furnishes a 2D surface reflection map of tissue that arises from the column integrated electromagnetic properties of the tissue down to a depth limited by absorption, system SNR, etc. Consider the recursive field reflection coefficient in EQ. 10 (Z. D. Taylor, et al., *IEEE Trans. Terahertz Sci. Technol.*, 5(2):170-83, 2015; Z. D. Taylor, et al., *IEEE Trans. Terahertz Sci. Technol.*, 5(2):184-96, 2015; the disclosures of which are incorporated herein by reference).

$$\Gamma_i = \frac{\rho_i + \Gamma_{i+1} e^{-j2\delta_i}}{1 + \rho_i \Gamma_{i+1} e^{-j2\delta_i}}, \Gamma_{N+1} = \rho_{N+1} \qquad \text{EQ. 10}$$

Equation 10 describes the field reflectivity of a stack of N homogenous, isotropic layers with uniform thickness sandwiched between two half spaces. $\Gamma_i$ is the field reflectivity of the stack from layer i to N, $\rho_i$ is the field reflectivity from layer i–1 to layer i and $\delta_i$ is the complex path length of layer i. In a skin model, $\Gamma_i$, $\rho_i$, $\delta_i$ are all functions of the layer thickness and the water content at a particular layer. In the limit of optically thin layers, the aggregate reflectivity of skin (which displays a water content gradient) can be simulated by increasing the number of layers until the forward traveling incident radiation has been attenuated to some appreciably small level and then terminating the stack with a half space whose electromagnetic properties are equal to the final stack layer. Using the established formalism, the field reflectivity of the skin is denoted $\Gamma_1$.

In accordance with numerous embodiments, it is assumed that imaging contrast is strongly dependent on tissue water content, and thus the reflectivity of skin is a function of transverse dimension (x,y) and the tissue water content is a function of observation time ($t_m$): $\Gamma_1 \rightarrow \Gamma_1 (t_m,x,y)$. The system utilizes a 0-bias rectifier and thus, in accordance with many embodiments, the system pixel value is a function of the THz reflectivity of the pixel position:

$$R(t_m,x,y) = |\Gamma_1(t_m,x,y)|^2 \qquad \text{EQ. 11}$$

The recursive relation in EQ. 10 continually references the electromagnetics properties of adjacent layers and thus EQ. 11 can be thought of as a column integrated (weighted average) reflectivity with the depth dependent weighting described by the term $e^{-j2\delta_i}$.

Figure 19A:
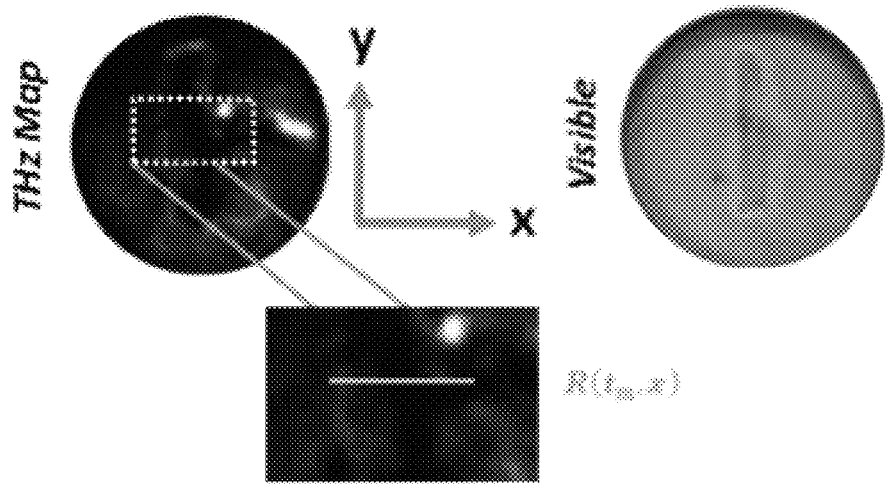
FIGS. 19A and 19B provide spatial dimensions and segmentation of (A) a THz image and (B) its companion MRI image for a full thickness burn at t=90 min, generated in accordance with various embodiments.

Thus, similar to its companion visible image, a THz image is represented only in the horizontal (x) and vertical (y) dimensions and, therefore, does not provide reflectivity resolved in the depth (d) dimension (FIG. 19A). THz image sets are displayed in a standard false color map where black-red-yellow-white denotes increasing reflectivity. For all time-series THz burn images, a white linear contour measuring 5 mm was drawn to transversely segment the burn contact tissue along the x-dimension. In accordance with numerous embodiments, pixel-by-pixel reflectivity values of the white contour were normalized to the maximum THz reflectivity acquired from an aluminum calibration target (i.e., ideal reflector) and zero THz reflectivity measured in the absence of a reflecting target (i.e., air). The calibrating reflector was positioned in the same manner and stand-off distance as abdominal skin during the initial THz system scans. Using the mean value theorem and in accordance with various embodiments, the mean reflectivity of the contour at time $t_m$ along the length of the contour, x, is expressed as $$R(t_m) = \frac{1}{\Delta x} \int_{\Delta x} R(t_m, x) dx \qquad \text{EQ. 12}$$

$R(t_m,x)$ was calculated at all time points for both burn wound models. Using this analysis of THz imagery, a single profile of mean reflectivity associated with the burn image feature (i.e., white linear contour) was plotted as a function of time for both a partial thickness and full thickness burn wound model, in accordance with a number of embodiments.

Figure 19B:
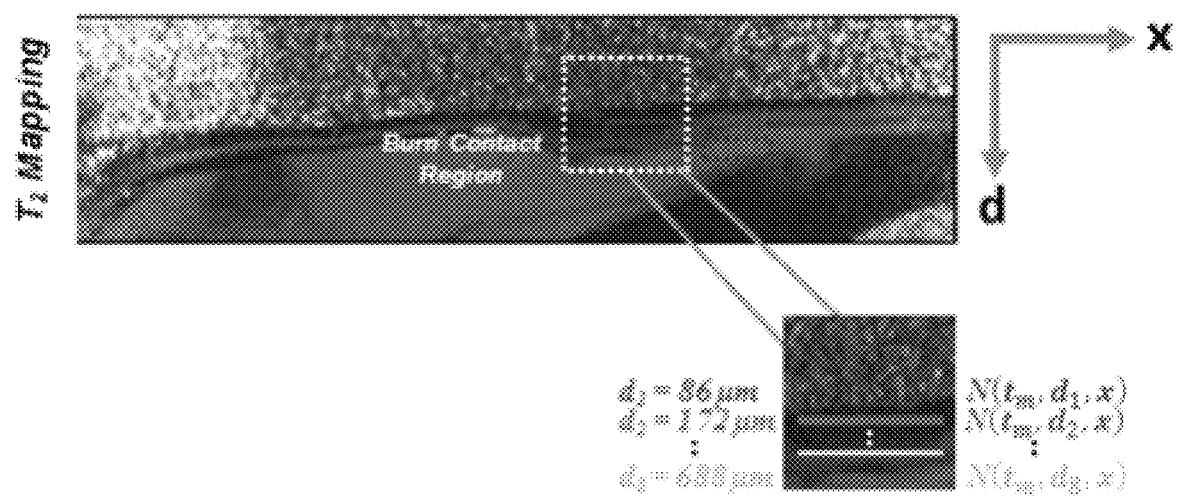

While the companion MRI scan is similarly 2D (FIG. 19B), this image provides the spatial distribution of TWC in burn tissue along the x-dimension and across multiple skin layers (i.e., d-dimension). Specifically, the x-dimension of every $T_2$w and $T_2$-mapping image pair spatially maps to the length of the white linear contour drawn in its companion THz image. Mapping between MRI, visible, and THz imagery was achieved by capturing contiguous MRI slices of known thickness (2 mm) along the y-dimension of the burn, measured to be ~20 mm, that include the MRI fiducial markers. MRI images are displayed in a gray-scale color map where black-grey-white indicates increasing intensity and $T_2$ relaxation time for $T_2$w and $T_2$-mapping images, respectively. The MRI signal, S, for a $T_2$w image is:

$$S = k \cdot N \exp\left(-\frac{T_E}{T_2}\right) \qquad \text{EQ. 13}$$

where k is a function of the instrument's receiver gain, N is proportional to the mobile proton density, $T_2$ is the transverse MR relaxation time, and $T_E$ is the echo time.

Parametric analyses were performed on $T_2$-mapping MRI slices at $T_E=28$ ms. Those MRI slices with the greatest observable contrast in the dermal layer of the burn were selected for image analysis at each time point. These slices mostly reside in the center of the wound, and therefore did not capture the fiducial markers positioned at the extremes of the MRI slice stacks. To analyze mean $T_2$ relaxation time and mean relative proton density (i.e., mobile TWC) as a function of depth in each $T_2$-mapping image, a white contour, measuring 5 mm in length, was drawn along the x-dimension of the burn contact area. The same contour was superimposed at incrementally increasing depths (~86 μm) in the dermis, measuring ~700 μm in thickness.

For all time points (t=0 min, 90 min, 210 min, and 270 min), the mean $T_2$ time and the associated standard deviation was calculated using ImageJ (NIH, Bethesda, Md.) by fitting to relation to EQ. 13 the signal intensity S from the contour at every depth in $T_2$-mapping images. Note that S is a function of the instrument's receiver gain, k, which is optimized for each longitudinal time point. Consequently, N of the burn tissue was normalized to that of the previously described MRI fiducial marker to obtain comparable N values across all time points in the study. Mean proton density at time $t_m$ and depth $d_n$ is expressed as $$N(t_m, d_n) = \frac{1}{\Delta x}\int_{\Delta x} N(t_m, d_n, x)dx \qquad \text{EQ. 14}$$

Using this analysis of MRI imagery, multiple profiles of mean $T_2$ time and relative proton density associated with the image feature (i.e., white linear contour) were plotted as a function of time and depth for both burn wound models.

Collectively, and in accordance with numerous embodiments, this THz and MRI image analysis demonstrates there is a one-to-multiple relationship between THz imaging and MRI data, respectively, at each time point; for both burn types, THz imaging results are plotted as a single temporal profile, whereas MRI imaging results are plotted as unique temporal profiles for each tissue depth. Because only relative proton density is a direct measure of mobile TWC, a one-to-many correlation across time was required between THz reflectivity of the burn region and relative proton density measurements acquired by MRI at specific tissue depths in the same tissue. Using this type of correlation, we can not only investigate how well THz reflectivity correlates with TWC-based MRI measurements, but also determine at which MRI depths in the tissue these correlations are strongest. This analysis addresses the core aims of the study: 1) to investigate TWC-based contrast of THz imaging and 2) determine tissue depths at which THz imaging can probe TWC.

Normalized Cross-Correlation:

Numerous embodiments utilize normalized cross-correlation, which is a method that can be used to compare reflectivity and depth-dependent relative proton density of images acquired with THz imaging and MRI, respectively, by first normalizing these measurements and then calculating the displacement of one relative to the other. This is also known as a sliding dot product. Vectors of time dependent variables used in the normalized cross-correlation are defined as follows:

$$\vec{N}(d_n) = [N(t_1, d_n) N(t_2, d_n) N(t_3, d_n)] \qquad \text{EQ. 15}$$

$$\vec{R}_{THz} = [R(t_1) R(t_2) R(t_3)] \qquad \text{EQ. 16}$$

The cross correlation coefficient of the THz time series with the depth dependent MRI relative proton density series is written as the inner product:

$$\rho(d_n) = \left\langle \frac{\vec{N}(d_n) - \text{mean}(\vec{N}(d_n))}{\|\vec{N}(d_n) - \text{mean}(\vec{N}(d_n))\|}, \frac{\vec{R}_{THz} - \text{mean}(\vec{R}_{THz})}{\|\vec{R}_{THz} - \text{mean}(\vec{R}_{THz})\|} \right\rangle \qquad \text{EQ. 17}$$

where the mean and magnitude of a vector $\vec{v}$ in $\mathbb{R}^M$ is $$\text{mean}(\vec{v}) = \frac{1}{M}\sum_{m=1}^{M} v_m \qquad \text{EQ. 18}$$

$$\|\vec{v}\|^2 = \sqrt{\sum_{m=1}^{M} |v_m|^2} \qquad \text{EQ. 19}$$

The inner product of the two vectors, $\vec{u}$ and $\vec{v}$, in $\mathbb{R}^M$ is:

$$\langle \vec{u}, \vec{v} \rangle = \sum_{m=1}^{M} u_m v_m \qquad \text{EQ. 20}$$

The result is a temporal correlation coefficient (p) between THz reflectivity across the burn and relative proton density at each MRI burn depth for both a partial thickness and full thickness burn wound.

Figure 20:
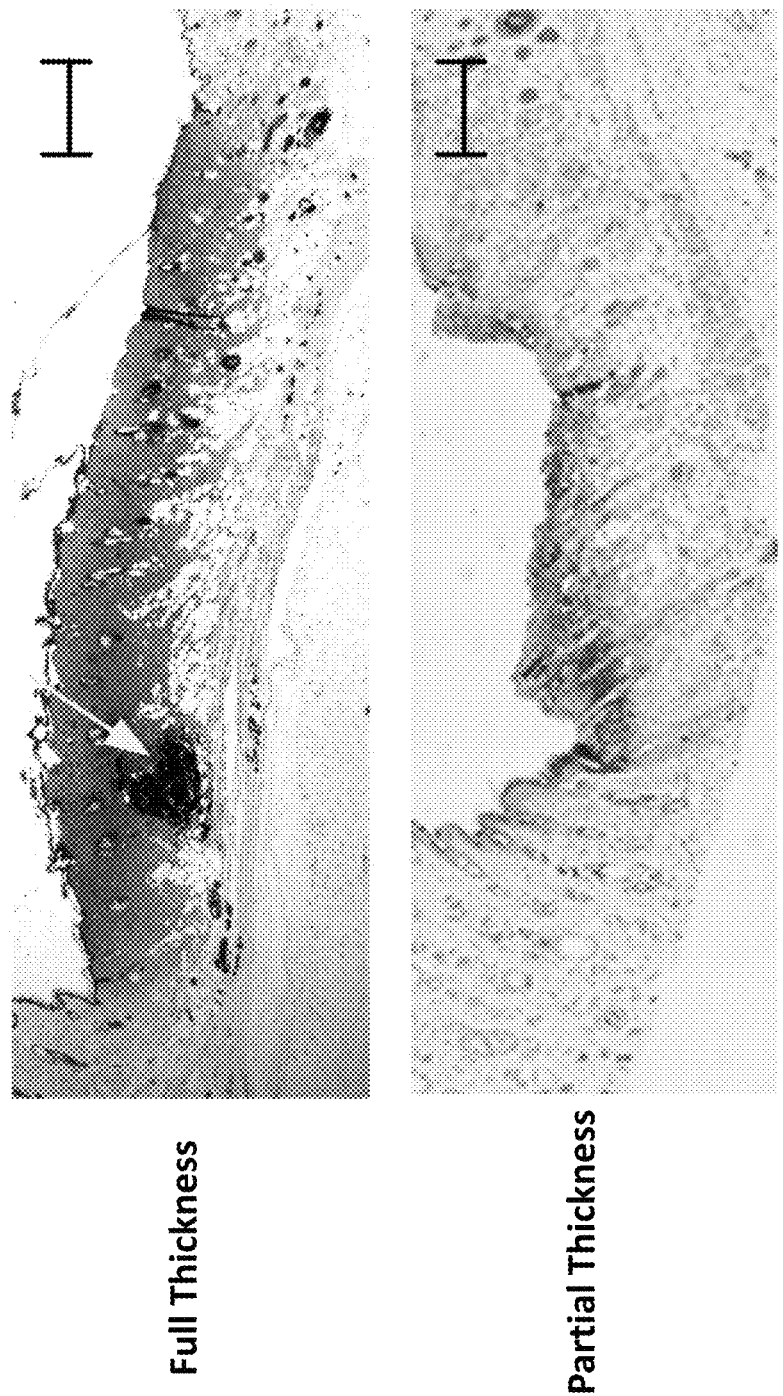
FIG. 20 provides images of H&E staining to assess burn wound severity of a full thickness and partial thickness wound 72 hours post burn induction.

Histological Assessment:

A blind histological analysis of burn tissue harvested at 72 h post injury was compared to visible imagery to assign burn severity. Histological features in burn wounds are known to manifest by 72 hr following thermal insult, and therefore this endpoint was used to harvest tissue and histologically determine burn severity (i.e. partial thickness and full thickness) (FIG. 20). Three regions of the burn wound (i.e., left, center, and right) were harvested, transferred to 10% formalin solution, and submitted for histopathological evaluation. All tissue samples were sectioned orthogonal to the major axis of the burn and some contained an intradermally injected tattoo marker for orientation of the tissue specimen. Six histological slices of 5 μm thickness were acquired from each tissue block, stained with hematoxylin and eosin, and analyzed to determine burn severity. Histology sections included both burned and healthy areas, providing a control area consisting of unburned tissue to which the burned area was compared. A blind investigation of depth of injury was used to confirm that the 130° C. and 200° C. wound were a partial thickness and full thickness burn, respectively. Complete epidermal necrosis, muscle necrosis, collagen discoloration, and occluded vessels were used to characterize a full thickness wound. In regards to depth of injury, these histological features extend into the dermis and subcutaneous layer. In contrast, patent vessels as well as intact skin and muscle tissue that did not exhibit signs of cellular damage were used to classify a partial thickness wound (P. Tewari, et al., *J. Biomed. Opt.*, 17(4):0405031-0405033, 2012, the disclosure of which is incorporated herein by reference).

Results

Figure 21:
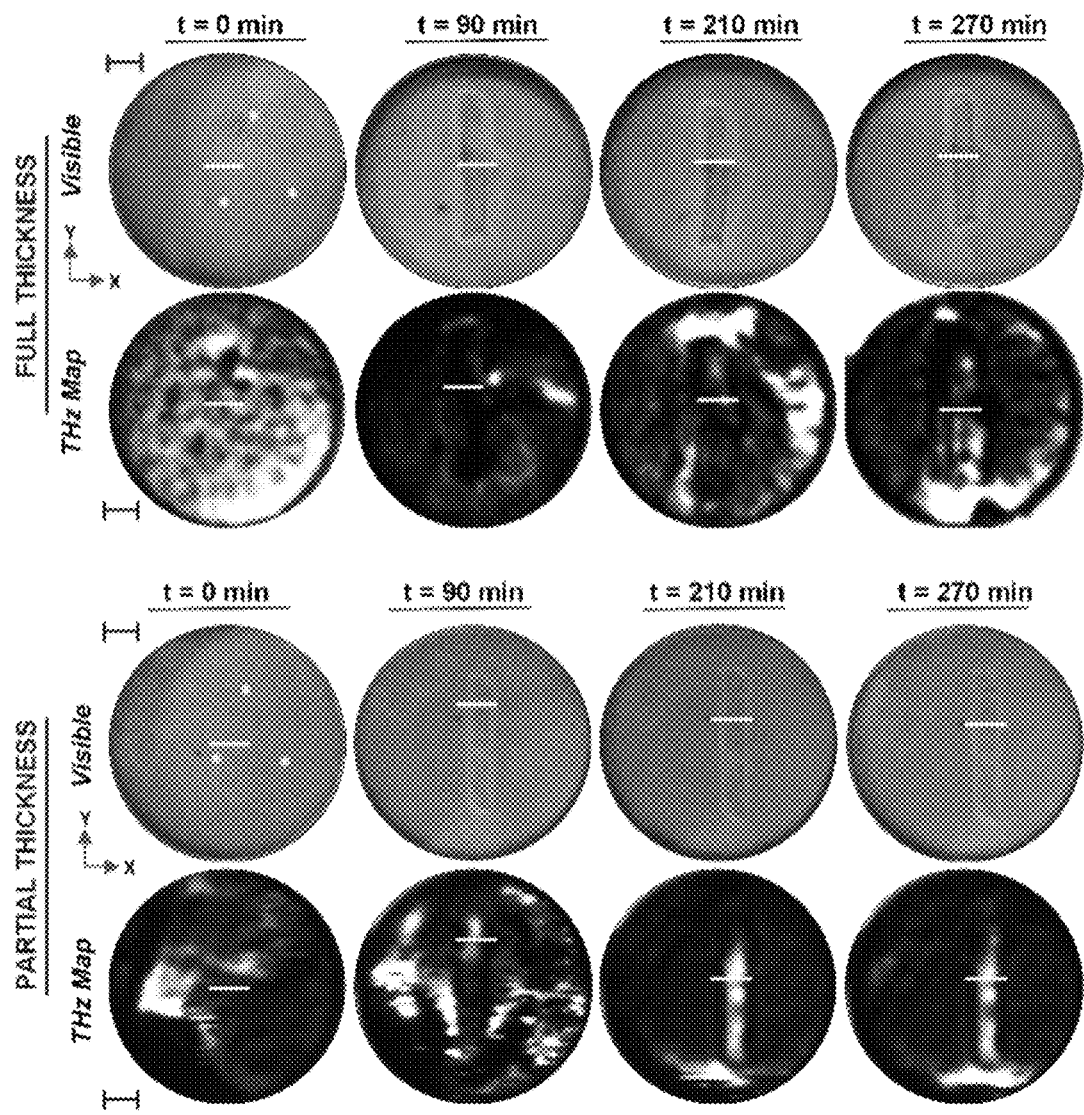
FIG. 21 provides a time-series of 2D THz and visible imagery of full thickness and partial thickness burn wounds in rat abdomen in vivo, generated in accordance with various embodiments.
Figure 22:
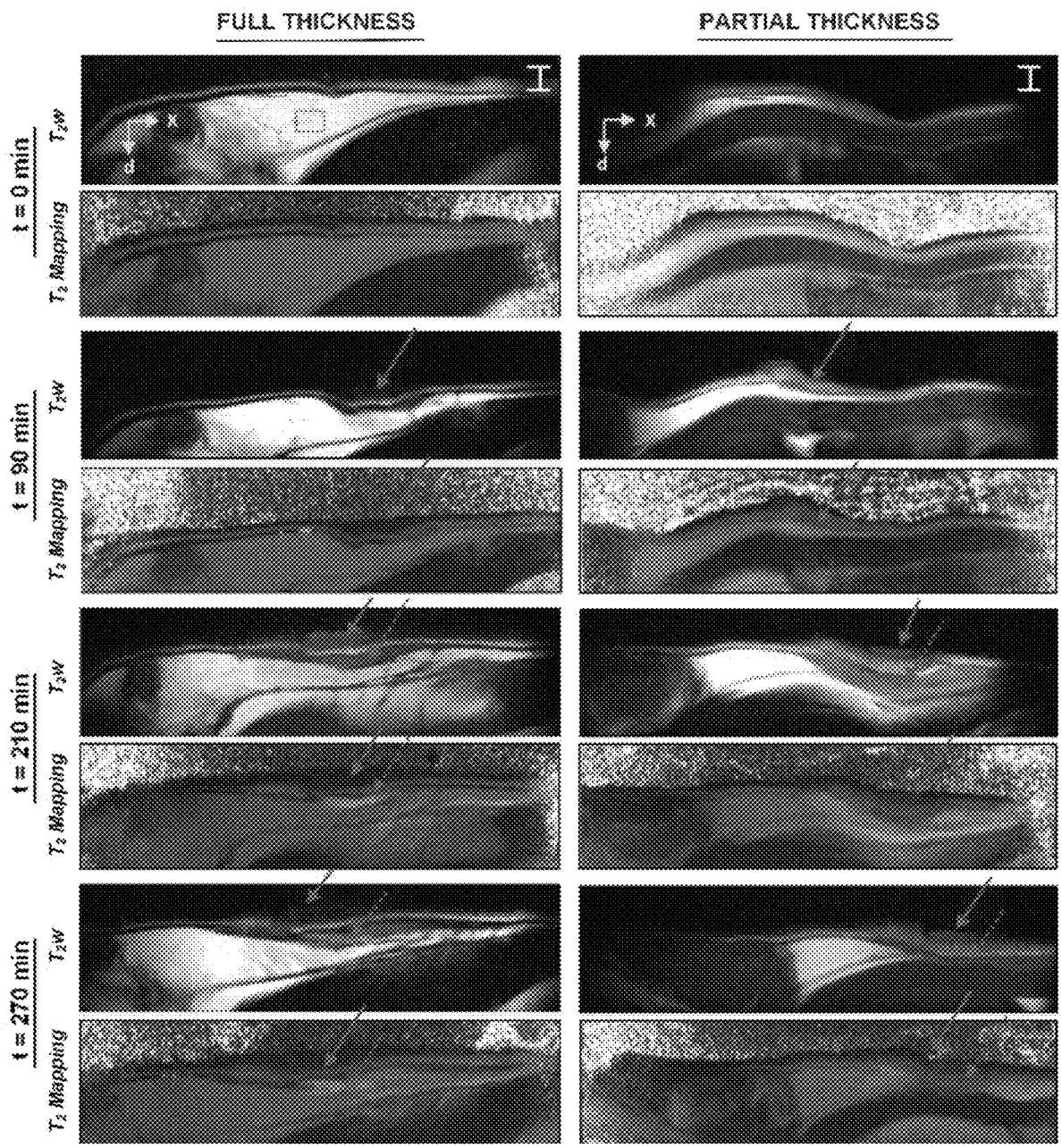
FIG. 22 provides a time-series of companion MRI imagery of full thickness and partial thickness burn wounds in rat abdomen in vivo.

Parallel THz and MRI time-series imagery of a partial thickness burn and full thickness burn induced in the abdominal skin of anesthetized rats were acquired over a 5 hr period (FIGS. 21 and 22). During THz imaging, burn wounds were imaged under a thin (12 μm) film Mylar window, in accordance with various embodiments, to eliminate confounding effects from non-uniform surface contours (FIG. 21). Solid red arrows and dotted red arrows in MRI images of FIG. 22 denote the location of the burn contact area and resultant edema formation in the dermis, respectively.

Visual inspection of the time-series MRI images shows the positions of these arrows are not at their original position. This shift in position is neither arbitrary nor relevant to tissue swelling, but instead due to the difficulty in repositioning the animal after transferring the subject between the MRI scanner and THz imager at each time point. Despite the red indicators not being spatially registered, the burn contact area and resultant edema are successfully captured in the FOV of MRI images for both subjects at all time points.

Figure 23:
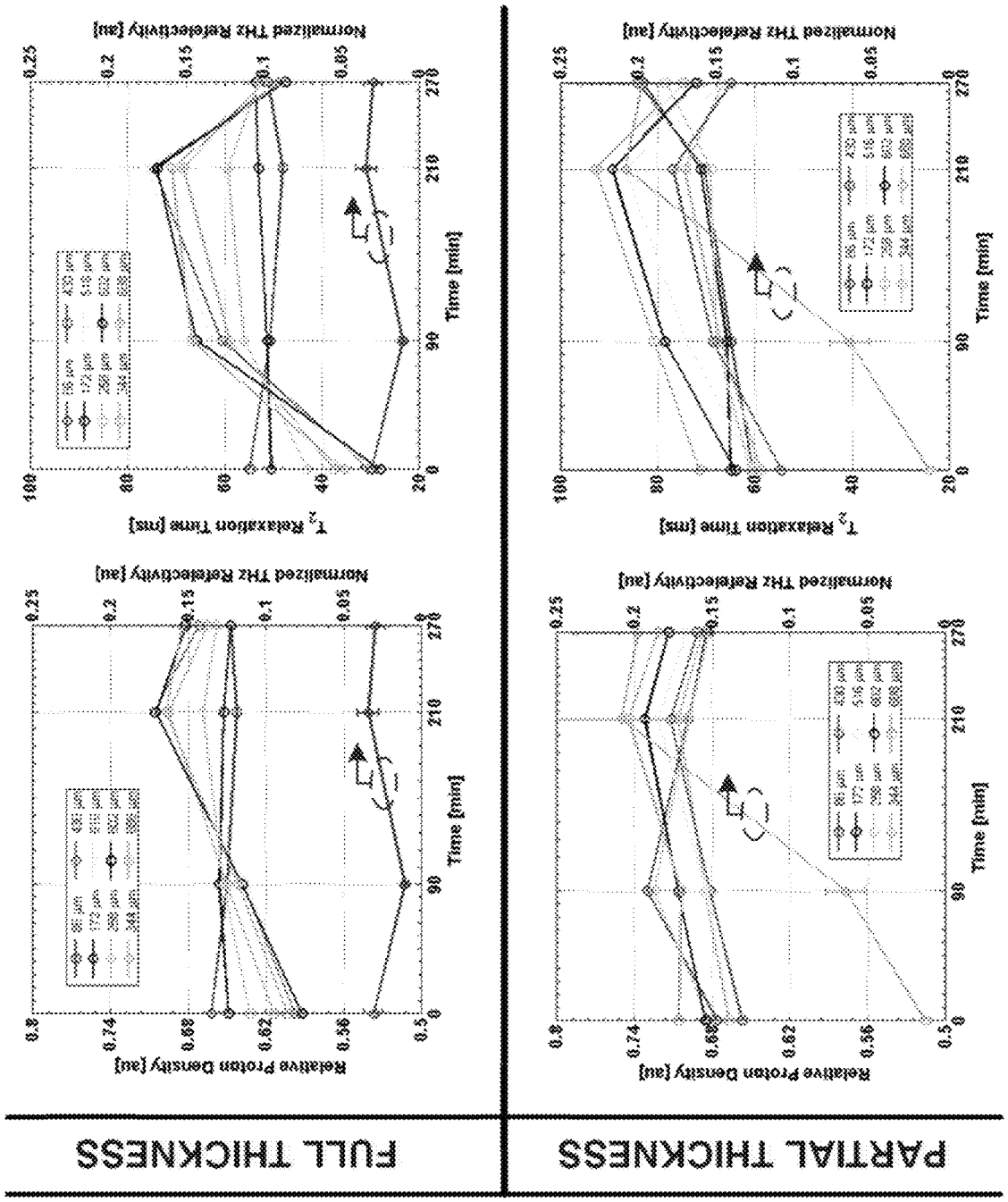
FIG. 23 provides temporal plots of THz and depth-dependent MRI parameters, comparing mean relative proton densities (i.e., mobile TWC or edema) and mean $T_2$ relaxation times at varying skin depths with normal THz reflectivity as a function of time for a full thickness and a partial thickness burn wound, generated in accordance with various embodiments.

Temporal profiles of normalized THz reflectivity were generated for the burn contact site in each wound model (FIG. 23). In comparison, multiple temporal profiles of mean $T_2$ time and relative proton density were generated for specific tissue depths associated with the same burn contact region in spatially mapped MRI image sets (FIG. 23).

THz images of the rat abdomen prior to inducing a full thickness and partial thickness burn (FIG. 21) display mostly uniform THz reflectivity across the FOV. Companion mean $T_2$ times of the epidermis ($T_2=34\pm5$ ms), dermis ($T_2=26\pm7$ ms), and hypodermis ($T_2=57\pm8$ ms) are consistent with previously published in vivo MRI values for skin (t=0 min in FIG. 22) (S. Richard, et al., *J. Invest. Dermatol.*, 97(1):120-25, 1991; S. Richard, et al., *J. Invest. Dermatol.*, 100(5):705-09, 1993; the disclosures of which are incorporated herein by reference).

Following thermal insult (t=90 min), THz reflectivity across the burn region and $T_2$ time and relative proton density of burn tissue at tissue depths >258 µm rise and fall together with a biphasic trend. The evolution of THz reflectivity and MRI tissue measurements is not identical for each wound severity. For a full thickness wound immediately following burn induction, THz imaging captures a drop in THz reflectivity in the wound contact area (FIG. 23) while MRI detects an increase in relative proton density (i.e., mobile TWC) in the same burn region with respect to uninjured skin (t=0 min). This increase in relative proton density is evident across varying depths—between 172 and 688 µm—in the dermis of the burn tissue (FIG. 23).

By comparison, a partial thickness wound is characterized by an increase in both THz reflectivity and relative proton density in the burn contact area for depths >258 µm immediately following thermal injury (FIG. 23). These measurements are also greater in magnitude than those in a full thickness wound. For example, at a depth of 516 µm, relative proton density and T2 time (FIG. 23) for the same region of a partial thickness wound at t=90 min compared to that of uninjured skin are 3.6% and 7% greater, respectively. The corresponding THz reflectivity for a partial thickness burn is calculated to be 7% greater than that of uninjured skin. In contrast, reflectivity and MRI differences between burn tissue and uninjured tissue are not as substantial in a full thickness wound at t=90 min. MRI and THz parameters associated with the burn contact area both peak at t=210 min and visibly decline at t=270 min in each of the two burn severity models. For a depth of 516 µm at t=210 min the THz reflectivity, $T_2$ time, and relative proton density of a partial thickness wound are 20%, 45%, and 7% greater, respectively, than values in uninjured tissue. In contrast, all mean THz and MRI measurements at their temporal peak for a full thickness wound are lower in magnitude; for the corresponding dermal depth at 210 min the THz reflectivity, $T_2$ time, and relative proton density are 1%, 15% and 5% greater, respectively, in a full thickness wound compared to uninjured skin. Finally, a concurrent decline in mean THz reflectivity, $T_2$ time, and relative proton density becomes visible in both burn types by t=270 min (FIG. 23). Accordingly, numerous embodiments utilize THz reflectivity data to diagnose burn wound thickness.

In accordance with numerous embodiment, reflective THz imaging is used to rapidly and non-invasively track fluid shifts in an in vivo injury-induced edema model with excellent contrast and sensitivity. THz reflectivity measurements of the burn contact area rise and fall with companion MRI measurements acquired of the burn tissue region at greater skin depths (>258 µm) as a function of time. Moreover, the biphasic pattern and distinct magnitudes of these measurements for both burn types agree with burn edema pathogenesis commonly observed in partial thickness and full thickness wounds as well as predicted electromagnetic behavior of tissue.

Immediately following burn induction of a full thickness burn (t=90 min), THz imaging captures a drop in THz reflectivity in the wound contact area (FIG. 23) while MRI detects an increase in relative proton density (i.e. mobile TWC) and $T_2$ time in the same burn region with respect to uninjured skin (t=0 min). This increase in both MRI parameters is evident across varying depths—between 172 and 688 µm—in the dermis of the burn tissue (FIG. 23). The inconsistency between measurements acquired with both imaging modalities is not arbitrary but instead explained by burn pathophysiology and how this tissue response markedly varies in the first hour following a full thickness injury: a survey of the literature indicates burn edema pathogenesis of a full thickness wound is first characterized by an immediate, localized drop in mobile TWC due to a transient cessation of vascular perfusion (R. H. Demling, 2005, cited supra; R. H. Demling, 1982, cited supra). This response is only on the order of minutes. With respect to THz-tissue behavior, stratified media modeling of skin predicts that the THz reflectivity of a tissue system imaged at our center operating frequency (~525 GHz) decreases approximately linearly with decreasing TWC. Because THz imaging (~10 min acquisition time) is performed before MRI (1 hr acquisition time), this immediate decrease in TWC for a full thickness burn is observed as a decrease in THz reflectivity. Following this initial, transient drop in TWC, a full thickness wound is known to be characterized by a subsequent increase in TWC. Because an MRI image takes approximately an hour to acquire, TWC captured in these images correspond to the second phase of the full thickness burn edema response: the increase in TWC is reflected by a greater $T_2$ relaxation time and relative proton density at t=90 min with respect to the pre-burn values. After t=90, THz reflectivity trends mirror those observed in companion $T_2$ times and proton density measurements at greater skin depths (>258 µm); both modalities visualize the same phase of the burn edema response, and therefore identical TWC. Because both THz and MRI measurements did not visualize the same TWC content at t=90 min, this time point was excluded in the normalized cross-correlation of the full thickness burn.

THz and MRI measurements for a partial thickness burn at t=90 min both increase with respect to uninjured skin because this wound type is not known to be characterized by an immediate, transient drop in TWC; a partial thickness burn wound is characterized by immediate and greater mobile TWC (i.e., pronounced arteriolar vasodilation), and, therefore, its THz and MRI imagery showed greater THz reflectivity and relative proton density from the time of burn induction.

While both MRI and THz data peak at t=210 min for both burn models (FIG. 23), peak values observed in the partial thickness wound are greater than those of a full thickness wound. These findings demonstrate that peak edema is greater in partial thickness burns than in full thickness burns due to a marked decrease in dermal perfusion as burn depth increases. The difference in the quantity of edema formation between a partial thickness and full thickness burn is based on the local capillary and interstitial changes as well as the general status of the vascular. Most of the vasculature and lymphatics are located in the dermis layer. In a full thickness burn, which affects all the skin layers, the dermal lymphatics are destroyed, impairing the transport of fluid to the burn site. This effect results in decreased blood volume and blood flow to the burn tissue, which, in turn, results in less edema compared to a partial thickness burn (i.e., TWC). Conversely, partial thickness burns only involve the epidermis and some layers of the dermis, and, as a result, the underlying vasculature is less damaged compared to a full thickness wound. This result leads to better vascular perfusion, and therefore more edema (i.e., TWC) in partial thickness burns. As shown by FIG. 23, the partial thickness burn tissue is characterized by higher total water content, that is proton density sensitive. A coincident increase in water binding capacity, that is $T_2$ sensitive, results in greater magnitudes for $T_2$ time in the partial thickness wound. In accordance with multiple embodiments, THz reflectivity of a tissue system of higher TWC (i.e. a partial thickness burn) is greater than that of a tissue system of lower TWC (i.e., a full thickness burn). Deeper layers of partial thickness wounds are also known to have increased edema, which is reflected by the higher mean relative proton densities that characterize MR measurements at greater depths (FIG. 23). The concurrent decline in THz and MRI parameters in both burn severities by t=270 min (FIG. 23) is consistent with the start of the final resorption phase of the edema response.

Figure 24:
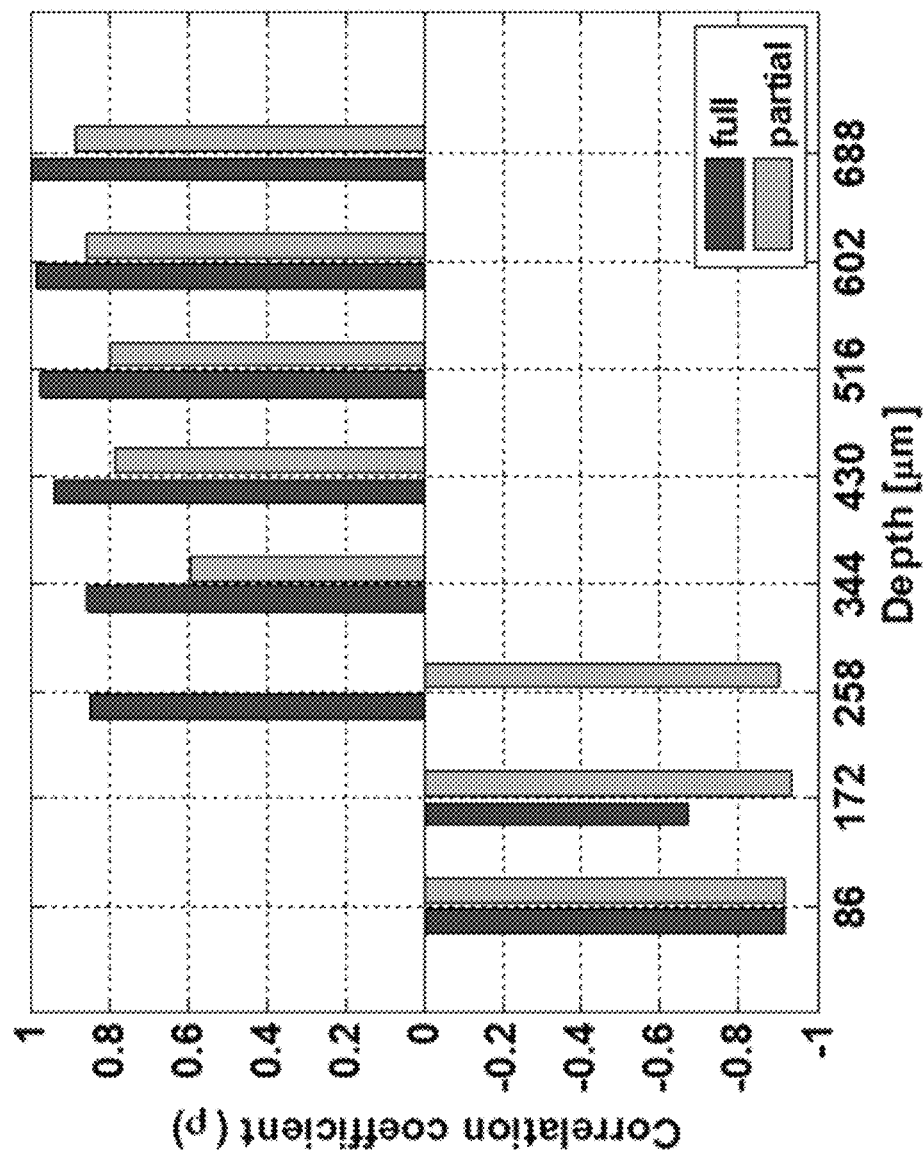
FIG. 24 provides temporal correlation of THz and MRI as function of depth computed from THz reflectivity profiles and relative proton density profiles for a full thickness and partial thickness burn wound, generated in accordance of various embodiments.

Several embodiments are directed to the use of the correlation between THz reflectivity of burn tissue with parallel measurements of depth-dependent relative proton density as a function of time, which is demonstrated in both burn models (FIG. 24). The most important result is that the correlation between THz and MRI measurements is strong for depths greater than ~300 µm; layers of the dermis (300-600 µm) are known to experience the greatest changes in TWC following injury. Specifically, strong positive correlations are evident at greater depths in the dermal tissue: at 688 µm, temporal coefficients (p) computed with normalized cross-correlation are as high as 0.97 and 0.86 for a full and a partial thickness wound, respectively. Depth-dependent variation in p is also correlated between the wound severities. These results suggest that mobile TWC strongly contributes to the observed THz imaging contrast, and that THz imaging tracks movement of water at dermal tissue depths that are relevant to edema assessment. Accordingly, many embodiments are directed to the ability to track movements of dermal tissue TWC to assess edema using reflective THz imaging.

THz reflectivity and companion TWC measurements of the upper dermis (at 86 µm and 172 µm) are anti-correlated. These depths, however, correspond to skin layers and tissue interfaces (i.e., the dermoepidermal junction) that are not known to contribute to the edema response, and, therefore, are less clinically significant and only of scientific interest. Because MRI signal varies markedly at tissue boundaries, anti-correlations at these depths may be due to system-related constraints and not pathophysiology. Conversely, changes in signal may also be due, in part, to wave interference effects.

In accordance with numerous embodiments, a comparative analysis shows that THz imaging can offer rapid measurements on TWC for potential edema assessment and provide these measurements earlier than existing clinical and research techniques (i.e., less than ten minutes). The time frame of edema assessment includes 1) the time when the technique can be implemented and 2) the acquisition time. Contributions from both measurements are of clinical importance for early and rapid detection of fluid shifts following cutaneous injury.

Example 5: Advances in Dielectric Window Selection & Effects on THz Wound Analysis The addition of a dielectric window creates a multilayer system that has interference effects due to internal reflections that vary periodically with frequency, causing the sensitivity to TWC of deeper layers to change relative to surface layers. To explore these effects, the power reflectivity of a tissue system under a window illuminated at 14° incidence angle and evaluated the response over illumination frequencies from 500 GHz-700 GHz was previously modeled (See Example 2). Effective media theory and the double Debye model of water were implemented to compute the TWC sensitivity metrics given the following two cases: a 500 µm thick quartz window (refractive index: 2.1), which is most commonly used by other THz groups, and a 12 µm thick Mylar window (refractive index: 1.5).

The thickness and refractive index of each window are markedly different such that the electromagnetic properties are unique for each substrate. Electromagnetic modeling predicts that the power reflectivity of a tissue system under quartz is frequency-dependent, and, therefore, varies non-linearly with respect to increases in TWC. Conversely, in the case of thin Mylar, a positive correlation was suggested between increases in TWC and THz reflectivity. Electromagnetic modeling, therefore, predicts that THz images taken using different dielectric windows vary not only in hydration sensitivity, but in information content, as the depth probed varies with the optical path length of the imaging system's window. Given these results, THz imaging with multiple windows could potentially be optimized to investigate and differentiate burn wounds of varying severity based on the TWC of specific burn wound regions.

Herein, THz window methodologies to enable visualization of unique and optimal TWC contrast in partial thickness and full thickness wounds in an in vivo rat model were examined. First, an optical window mount was developed to exchange dielectric windows to mitigate effects from surface irregularities in THz imaging. Reflective THz imagery (26 images/subject) of partial thickness and full thickness burn wounds were acquired with a thin-film Mylar window (refractive index: 1.5; thickness: 12 µm) and quartz window (refractive index: 2.1; thickness: 500 µm) to track the distribution of TWC throughout the wound bed over a period of 72 hr. THz burn maps were co-registered to temporally and spatially matched histological assessments to confirm wound severity in both burn models. It was hypothesized that a window methodology in THz burn imaging, in accordance with various embodiments, could be used to maximize TWC sensitivity to specific burn regions (i.e., the burn contact area and the surrounding tissue) depending on the expected tissue system hydration range. Histograms of pixel intensities within the burn contact area and uninjured tissue in THz image sets were computed to determine the effects of dielectric windows on THz burn image contrast.

Reflective THz Imaging System

For this example, the exemplary THz Imaging system utilized a photoconductive switch (PCS) based THz source that is pumped by a 780 nm pulse train created by a frequency-doubled 1550 nm mode-locked laser with a 230 fs pulse width and 20 MHz repetition frequency. The PCS is mounted on the back side of a high resistivity silicon hyper-hemisphere for the free-space output. The resulting THz source beam is collimated by a 76.2 mm effective focal length (EFL), 25.4 mm clear aperture off-axis 90° parabolic (OAP) mirror. A 50.8 mm EFL OAP mirror at a 14° incidence angle is used to focus the beam onto the target. The reflected THz radiation is then collected and collimated by a second 50.8 mm EFL OAP. Finally, a 25.4 mm EFL OAP couples the collected signal to the feedhorn of a WR1.5 waveguide mounted Zero-bias Schottky diode detector (ZBSD). THz pulses are detected and rectified by the ZBSD. Resulting THz signals are coupled to a gated receiver referenced to split the original optical pulses, that are detected with a 1550-nm high-speed photodiode. The THz imaging system acquires pixel-by-pixel data with a 1 ms integration time. The THz image is generated by raster scanning the region of interest beneath a fixed, focused THz beam using x and y stepper motors. An image with a 6 cm×6 cm FOV and 0.5 mm isotropic resolution can be acquired in ~10 min.

Figure 25:
FIG. 25 provides (left) a CAD diagram of an exemplary THz window mount and optical cartridge and (right) a photograph of an exemplary THz window cartridge housing a 500 μm quartz crystalline window in accordance with various embodiments.
Figure 25:
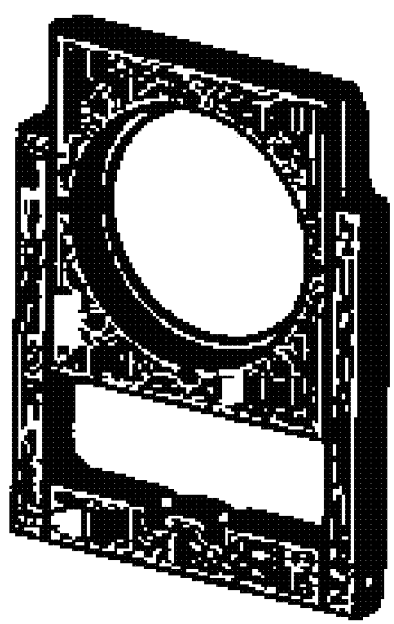

To ensure robust and repeatable target positioning, a cartridge system allowing optical windows with different dielectric properties to be exchanged was designed and fabricated in accordance with numerous embodiments (FIG. 25). Windows are exchanged from a rigid aluminum mount that is positioned orthogonal to the imaging head at a fixed standoff distance. The light weight, slip fit design of the rigid mount allows for easy insertion and removal of different optical cartridges and mimics that of an optical lens tube system to include threading compatible with a 5 cm diameter optical window and retaining ring. In this experiment, the cartridges house 5 cm diameter quartz and Mylar windows, that measure 500 μm and 12.5 μm in thickness, respectively, and an aluminum calibration reflector which is used to track maximum THz reflectivity signal during image acquisition. The center of the cartridges is coincident with the optical axis of the window and the standoff distance between the windows and imaging head are identical.

Animal Preparation

All experiments conformed to the guidelines set out by the Institutional Animal Care and Use Committee (IACUC). Four (n=4) 14 week old male Lewis rats (Harlan Laboratories, Hayward, Calif.) weighing 300-350 g were used as pre-clinical models to investigate effects of burn wound severity on TWC maps acquired with reflective THz imaging.

Animals underwent general anesthesia with inhaled isoflurane and were placed on a water heating pad for temperature regulation at 37±0.5° C. Each rat was shaved from scapula to pelvis to expose a 6×6 cm² area of abdominal skin and three green tattoos were applied to the abdomen; intradermal fiducial tattoo markers allow for image registration between the THz and visible images and histology. Specifically, histological slices of burn tissue that contain a fiducial marker are spatially mapped to the visible time-series imagery to assign burn severity to discrete locations within the burn. Burn protocols often produce mixed severity wounds where the depth of injury can be difficult to characterize, necessitating sampling from multiple sites. Intradermal injections of non-metallic green ink were administered via a sterile 28G needle to form the apices of a right triangle. Once tattooed, the rats were awoken and allowed to recover for 72 hr or until inflammation subsided.

Uninjured Skin:

Prior to burn wound imaging, a THz control (i.e., uninjured skin) study was performed in two rats to observe potential changes in THz reflectivity due to window-related pressure effects in the captured FOV. Anesthetized rats were placed in supine position on the internal heating pad under the THz imaging system, a dielectric window (i.e., either 12.7 μm Mylar or 500 μm quartz) was lowered onto the shaved abdominal skin to flatten the imaging field, and visible and THz images were captured with a SLR camera and the THz imager, respectively, over a 7 hr period, in accordance with many embodiments. Profiles of normalized THz reflectivity values across the skin were generated every 15 min for the first 2 hr and every 30 min for the remaining 7 hr to observe any window-related effects on THz image contrast. For the two remaining rats, a single THz scan and photograph were acquired of the uninjured abdominal skin under the quartz dielectric window. Image acquisition time of THz scans covered a 6×6 cm2 FOV. The scanned area of the abdomen was marked with a black marker, and the anesthetized rats were returned to the surgical field.

Burn Wound Induction:

The rats were then subcutaneously administered buprenorphine (i.e., analgesic), aseptically prepared with three alternating scrubs of betadine and isopropanol, and randomly assigned to receive either a partial thickness or full thickness burn wound (Table 3).

TABLE 3

| Experimental Parameters | | | | |
|---|---|---|---|---|
| Degree | ID | Weight (g) | Quartz/Visible Images (#) | Mylar/Visible Images (#) |
| Partial Thickness | A | 320 | 22/22 | 4/4 |
|  | B | 346 | 22/22 | 4/4 |
| Full Thickness | C | 324 | 22/22 | 4/4 |
|  | D | 348 | 22/22 | 4/4 |

A 2 mm×19 mm rectangular brass brand secured to a thermocouple (OMEGA, Stamford, Conn.) to accurately monitor the absolute temperature of the brand. The brand was heated to 200° C. and 130° C. using a hot plate, positioned between the fiducial markers using a high-precision manual z-stage, and applied to the abdomen with a constant pressure for 10 s to induce a full thickness and partial thickness burn, respectively. Each rat received one burn to minimize the total burned body surface area, thus reducing effects of shock on the physiologic wound response.

A 500 μm optical quartz window was then lowered onto the abdominal skin. Concomitant visible and THz imagery were continuously acquired every 15 min for the first 2 hours and every 30 min for the remaining 7 hrs. Upon scan completion, the quartz window was exchanged with a 12.7 μm Mylar window, and a single THz and visible image were acquired of the wound; because a 12.7 μm Mylar window was used in our previous THz burn imaging studies, concomitant THz burn imagery was acquired with the same thin-film Mylar window. The rat was then awoken and returned to the vivarium in 'care fresh' bedding to ensure minimum discomfort to the wound. An antibiotic (trimethoprim-sulfamethoxazole) was administered orally to prevent possible infection ensuing burn injury. A single follow-up THz scan and photograph were captured at 24 hr, 48 hr, and 72 hr post burn induction. At each time point, the dielectric Mylar and quartz window were lowered onto the wound during THz imaging. After a 72 hr observation period, the rats were euthanized with 4% isoflurane.

Pixel Intensity Distributions of THz Burn Imagery:

In accordance with several embodiments, pixel intensity distributions of time-dependent, serial THz burn imagery were performed to further analyze image contrast. Histograms of pixel intensities were generated for the Mylar and quartz windows from spatially co-registered fields of view (FOV) of: 1) the burn contact area and 2) the surrounding uninjured tissue in a full thickness and partial thickness wound. The surface areas corresponding to the burn contact site and surrounding tissue in the Mylar images at all acquired time points were manually segmented, and histograms of the enclosed pixels were then generated. These manual segmentations were then applied to parallel quartz images to ensure that the compared contrast corresponds to registered, overlapping FOVs. Because the rigid quartz window has a larger clear aperture than the flexible Mylar window, the quartz FOV for the uninjured tissue was eroded post processing to match that of Mylar.

A curved, solid line was superimposed on each plot to represent the cumulative distribution function (CDF) of each histogram. A dotted diagonal line was provided as a reference to gauge the skewness of the distribution-visualized as the difference between the area subtended by the CDF and the dotted line.

To further explore bias of the pixel distributions, the skewness of each histogram was computed using Equation 21, $$s = \frac{N^{-1} \sum_{k=0}^{n} (x_k - \bar{x})^3}{\left[(N-1)^{-1} \sum_{k=0}^{n} (x_k - \bar{x})^2\right]^{3/2}} \quad \text{EQ. 21}$$

where $\bar{x}$ is the pixel population mean and N is the total number of samples in the population. The results were plotted as red and blue bars to indicate the skewness of the pixels obtained with Mylar and quartz, respectively.

Histology:

A blind histological analysis of burn tissue harvested at 72 hr post burn induction was compared to visible and THz imagery to determine wound severity in both burn models. 1.5 cm×2 mm sections of tissue along the rostrocaudal axis were harvested from the left, center, and right regions of each burn, transferred to 10% formalin solution, and submitted for histopathological evaluation. All tissue samples were histologically sectioned sagittally to the major axis of the sample and most contained an intradermal tattoo (i.e., fiducial marker) for orientation and registration of the tissue specimen. Three histological slices of 5 μm thickness were acquired from each tissue block and stained with hematoxylin and eosin (H&E). Histology sections included both injured and uninjured tissue, providing a control area which the burned area could be compared to. Light microscopy was used to examine the burn slices, followed by analysis of the observed structural tissue damage to assign burn severity.

Results

Figure 26:
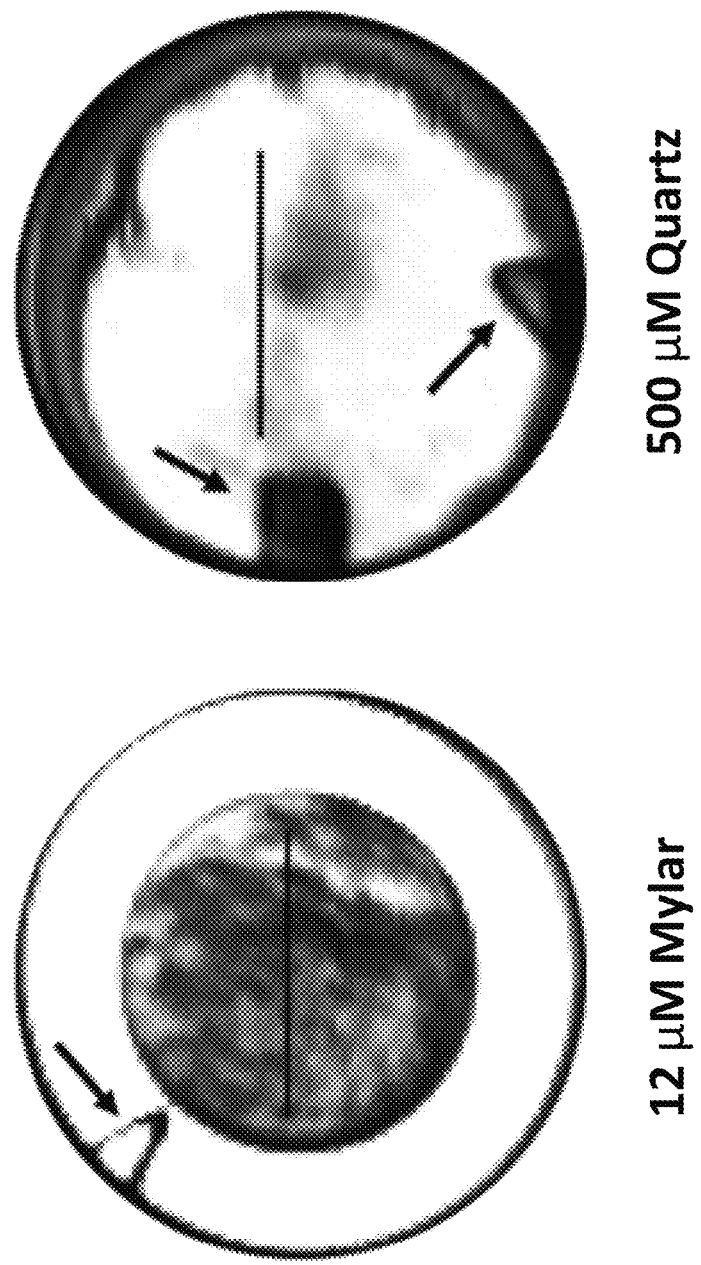
FIG. 26 provides exemplary THz imagery of injured skin at seven hours post burn induction under (left) a 12 μm Mylar and (right) a 500 μm quartz crystalline window, generated in accordance with various embodiments.

In Vivo THz Imaging of Uninjured Skin:

To investigate potential effects from window-related pressure on THz burn imaging contrast, time-series THz imagery of uninjured abdominal skin in two anesthetized rats was continuously acquired using either the quartz or Mylar window over a 7 hr period (FIG. 26). This time window is identical to that used in previously described THz burn imaging examples and is motivated by the evolution of the acute wound response following cutaneous injury. Over this time course, negligible changes in THz image contrast were visually apparent, and therefore a single representative THz image is included for each dielectric window. The "hot" color map associated with THz imagery transforms black to the global minimum THz reflectivity and white to the global maximum THz reflectivity. For THz images acquired with a Mylar window, the field of view (FOV) includes a highly reflective brass ring along the periphery that functions as a calibration target. Both dielectric windows contain absorbing films cut into triangular and square shapes, and these serve as fiducial markers (denoted by a solid black arrow) to enable registration of visible and THz images (FIG. 26). Because both windows were kept stationary during THz scanning, all THz images were inherently registered in each subject.

Figure 27:
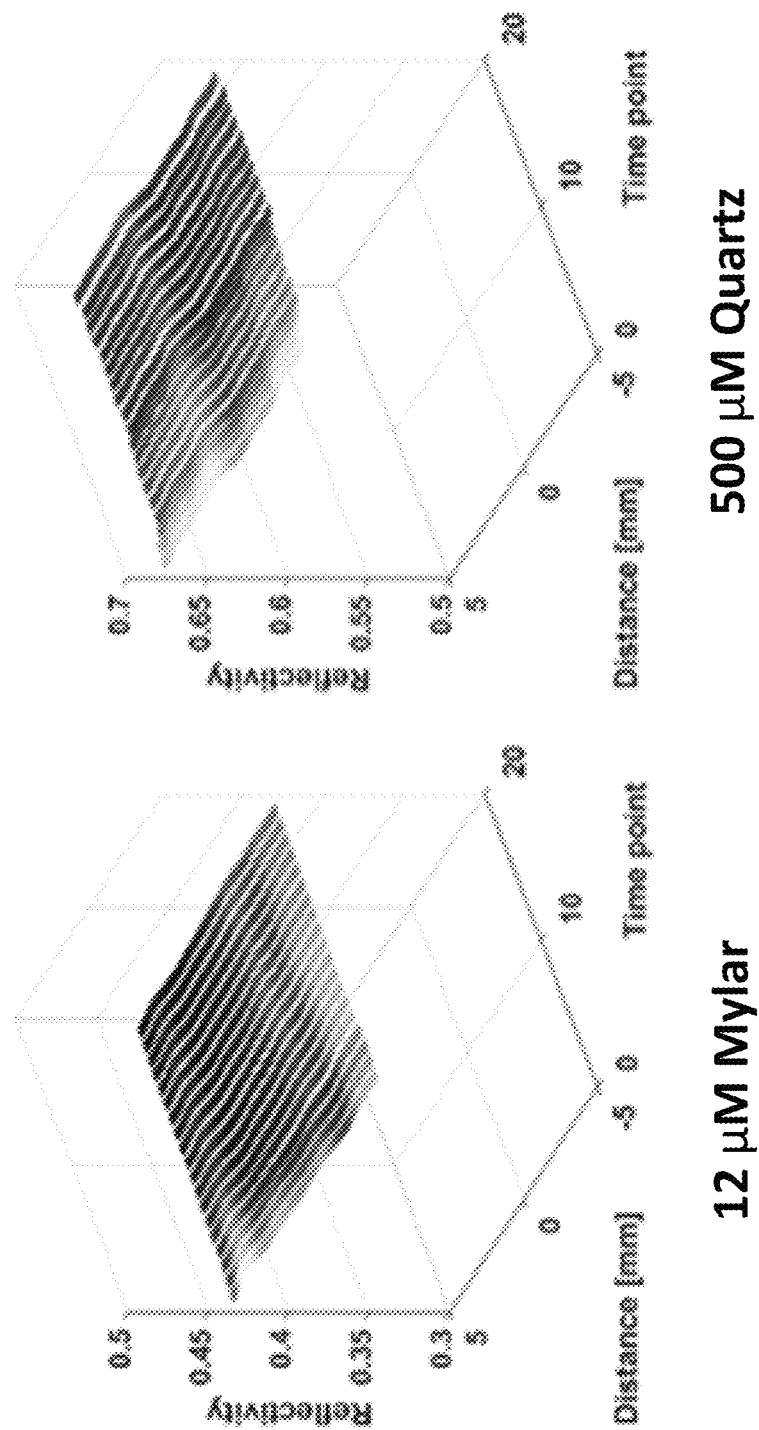
FIG. 27 provides THz reflective profiles that were generated for black horizontal contours that captured uninjured skin imaged under (left) a 12 μm Mylar and (right) a 500 μm quartz crystalline window, generated in accordance with various embodiments.

For all time-series THz imagery acquired over 7 hr, reflectivity profiles were generated for contours, indicated by black horizontal line segments in THz imagery in FIG. 26, that span the uninjured skin (FIG. 27). THz reflectivity values of these contours were normalized to the maximum THz reflectivity acquired from an aluminum calibration target (i.e., ideal reflector) and zero THz reflectivity measured in the absence of a reflecting target (i.e. air). The calibrating reflector was positioned in the same manner and stand-off distance as abdominal skin during the control study.

THz images of the rat abdomens (FIG. 26) under both Mylar and quartz displayed mostly uniform reflectivity across the FOV. Low reflecting areas, such as those evident in the center and periphery of skin imaged with quartz, may have resulted from reduced contact coupling between the window and underlying skin. The observed THz image contrast for both dielectric windows remained mostly unperturbed over the entire 7 hr scanning period. This result was further substantiated by companion THz reflectivity profiles (FIG. 27) that suggested little to no change in reflectivity for skin as a function of time. Normalized THz reflectivity of skin imaged under quartz was greater than that using Mylar due to the greater dielectric constant of quartz.

Figure 28:
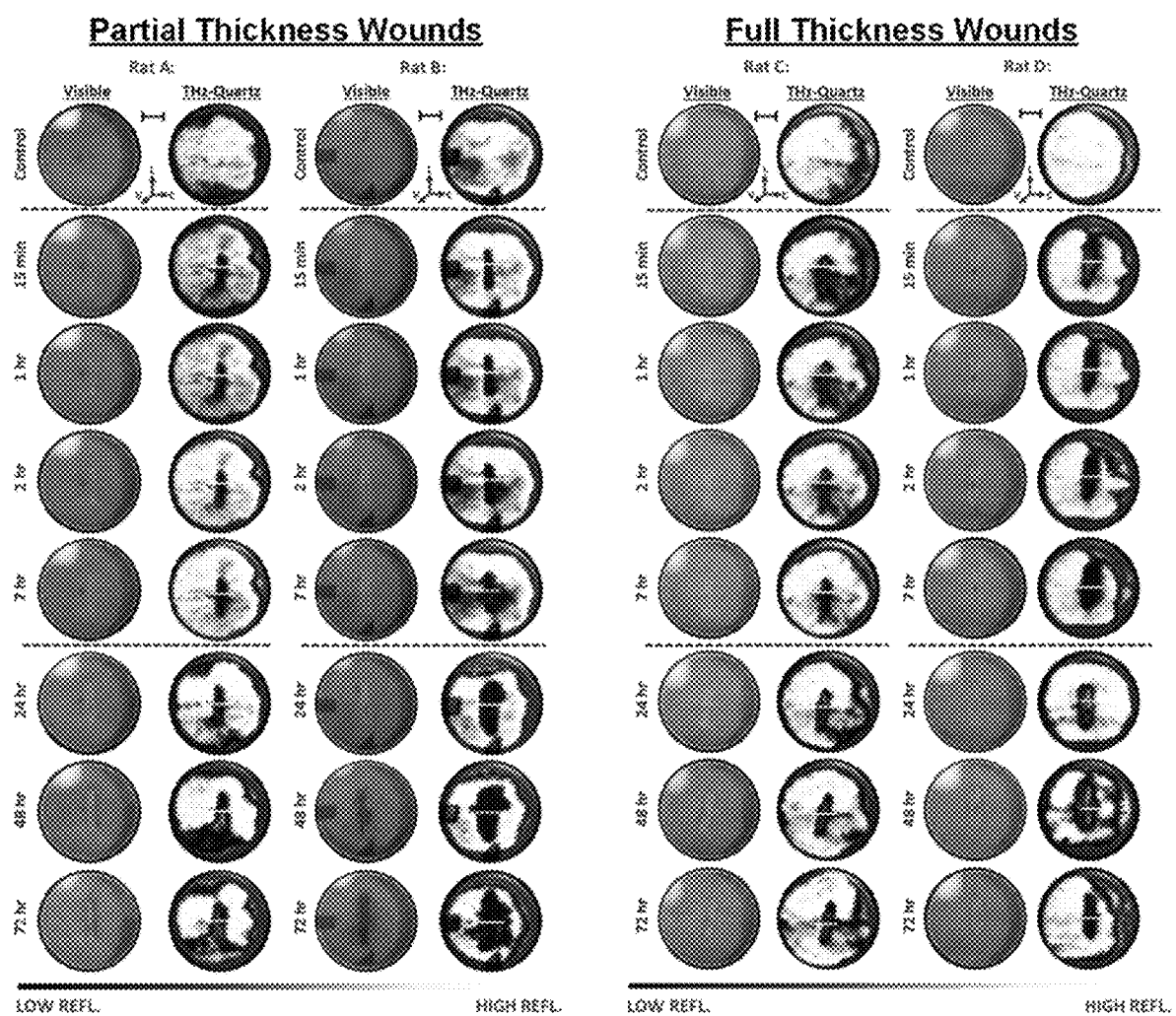
FIG. 28 provides a time-series of longitudinal THz and visible imagery of partial thickness and full thickness burn wound imaged under a 500 μm quartz crystalline window, generated in accordance with various embodiments.

In vivo THz burn imaging and visual observations: In vivo time-series THz and visible imagery of partial thickness (i.e., Rat A and Rat B) and full thickness (i.e., Rat C and Rat D) wounds in the abdominal skin of anesthetized rats was continuously acquired under quartz (FIG. 28). Green ink dots apparent in the visible image sets for all subjects are intrinsic tattoo fiducial markers that were used to compare histological wound outcome at 72 hr with THz frequency reflectivity measurements. Histological features in burn wounds are known to manifest by 72 hr following thermal insult, and therefore this time was used as the endpoint of the THz burn imaging study.

THz images of the rat abdomens prior to burn induction of both wound severities displayed mostly uniform reflectivity across the FOV. As previously described, low reflecting areas evident in the upper right quadrant of the FOV may have resulted from reduced contact coupling between the quartz window and underlying skin. Only the central area of the FOV (i.e., location of burn induction) is analyzed, therefore contributions from non-uniform THz contrast observed in these peripheral regions to reflectivity measurements are minimal.

Figure 29:
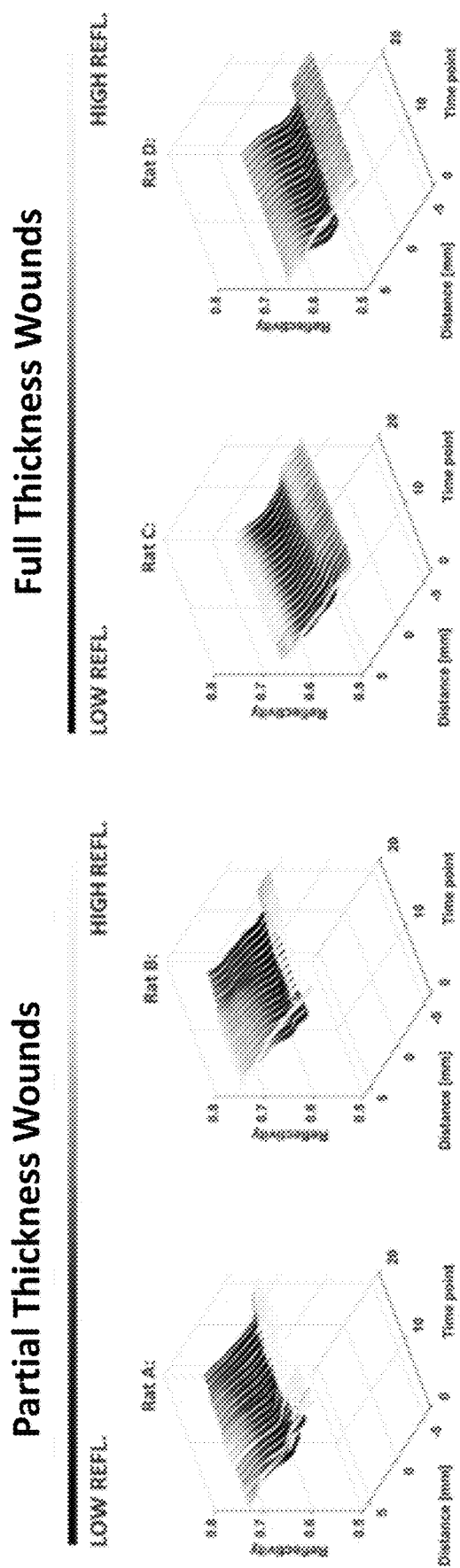
FIG. 29 provides THz reflective profiles that were generated for horizontal contours imaged under a 500 μm quartz crystalline window, generated in accordance with various embodiments.

Immediately following burn induction, THz images for partial thickness and full thickness wounds revealed unique THz contrast as well as identified the spatial location of the burn contact area (FIG. 28). Specifically, local variation in THz reflectivity was evident for this region with respect to the surrounding non-traumatized tissue. In partial thickness wounds (i.e., Rat A and Rat B), both visual inspection of THz imagery and normalized reflectivity profiles generated for the burn contact area indicate reduced reflectivity in this region that persists over 7 hr (FIGS. 28 and 29). Both Rat A and Rat B exhibited an ~11% drop in THz reflectivity with respect to the surrounding normal tissue. In comparison, little to no gross changes in the wound were detectable by visible inspection during the first 7 hr following thermal injury.

By 48 hr post burn induction, anatomical changes at the wound site become visually apparent for partial thickness burns. While the burn in Rat A remains mostly intact, that of Rat B displays early signs of ulceration, in which the topmost skin layer is completely delaminated exposing the underlying dermal tissue. While reduced THz reflectivity characterizes the burn contact region under quartz for both subjects on Day 0, THz imagery for Rat A at 24 hr shows two interesting features at the wound site: a central area of high reflectivity enveloped by a thin annulus of low reflectivity. This THz burn feature continues to grow in dimension by 72 hr, but is absent in Rat B. THz imagery of Rat B at 24 hr reveals low THz reflectivity at the wound contact area, similar to that observed on Day 0, which expands spatially as a function of time.

In accordance with many embodiments, time-series THz imagery of full thickness burn injuries imaged under quartz reveal variation in THz reflectivity that differs markedly from that for partial thickness wounds (FIG. 28). At the outset of injury, THz contrast of the burn contact area for both Rat C and Rat D immediately includes the central wound feature that first manifests in THz imagery of partial thickness wounds at 24 hr. However, the central area appears to be higher in reflectivity and more pronounced in size in full thickness injuries than in partial thickness wounds. In terms of change in reflectivity between the burn contact area and the surrounding uninjured tissue at 7 hr, this difference was lower in full thickness burns. Normalized THz reflectivity profiles that capture this region reveal that this change in reflectivity is ~2 fold lower in full thickness burns than in partial thickness burns (FIG. 29).

Figure 30:
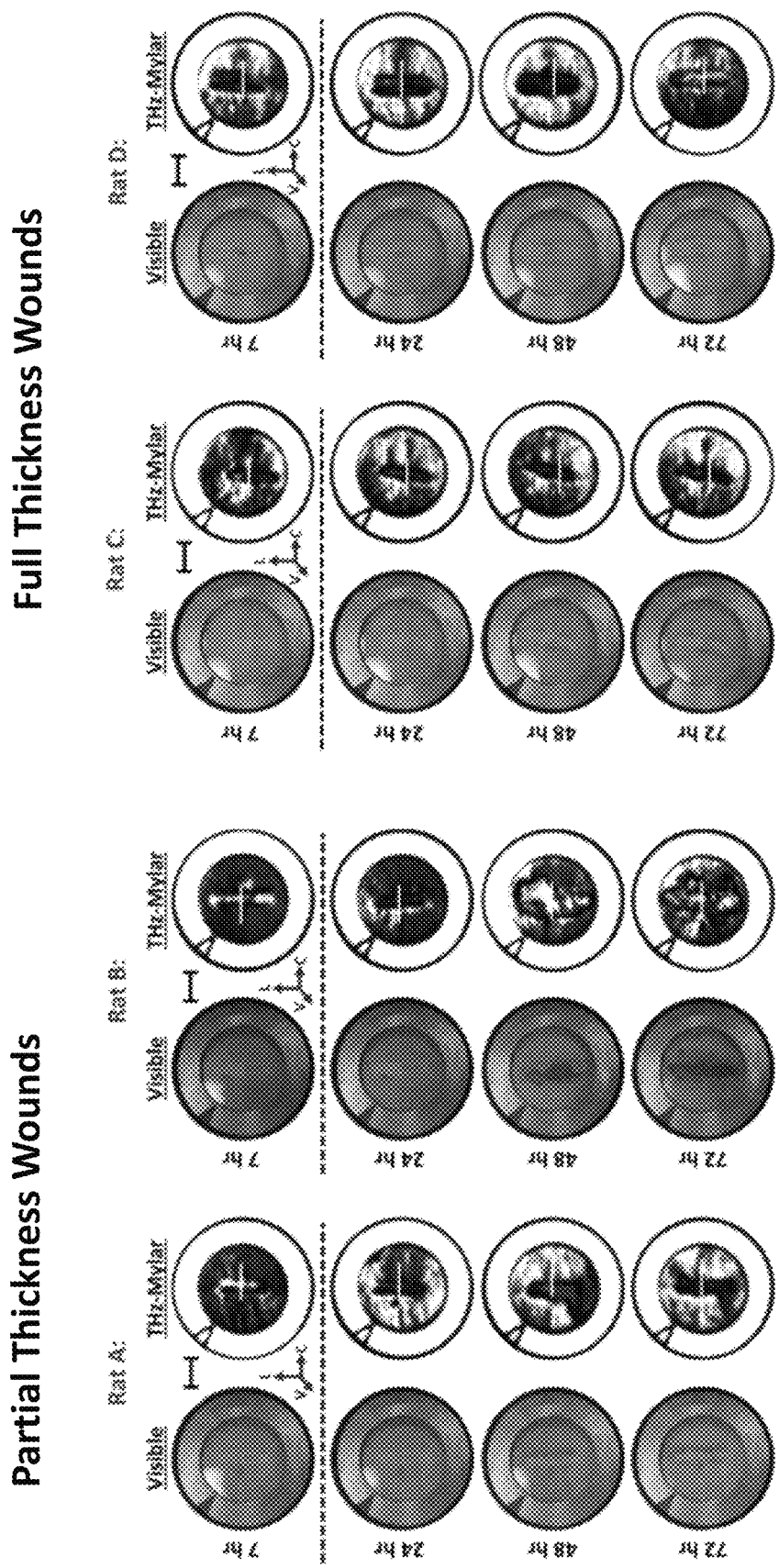
FIG. 30 provides a time-series of longitudinal THz and visible imagery of partial thickness and full thickness burn wound imaged under a 12.7 μm Mylar window, generated in accordance with various embodiments.

Burn images with the 12.7 µm Mylar window showed unique image contrast for both partial thickness and full thickness burn wounds (FIG. 30). These THz reflectivity findings are, in accordance of several embodiments, the inverse of those in parallel quartz burn images. Images of the burn contact region of partial thickness wounds under Mylar are characterized by a localized increase in THz reflectivity compared to that of the surrounding uninjured tissue (FIG. 30); the burn contact region appears as a discrete bright yellow band in both Rat A and Rat B. This result is most pronounced at 7 hr post injury and somewhat diminishes by 72 hr. In contrast, THz imagery of full thickness wounds (FIG. 30) imaged under Mylar reveal decreased reflectivity in the burn contact area at 7 hr that continues to persist in the follow-up scans.

Figure 31:
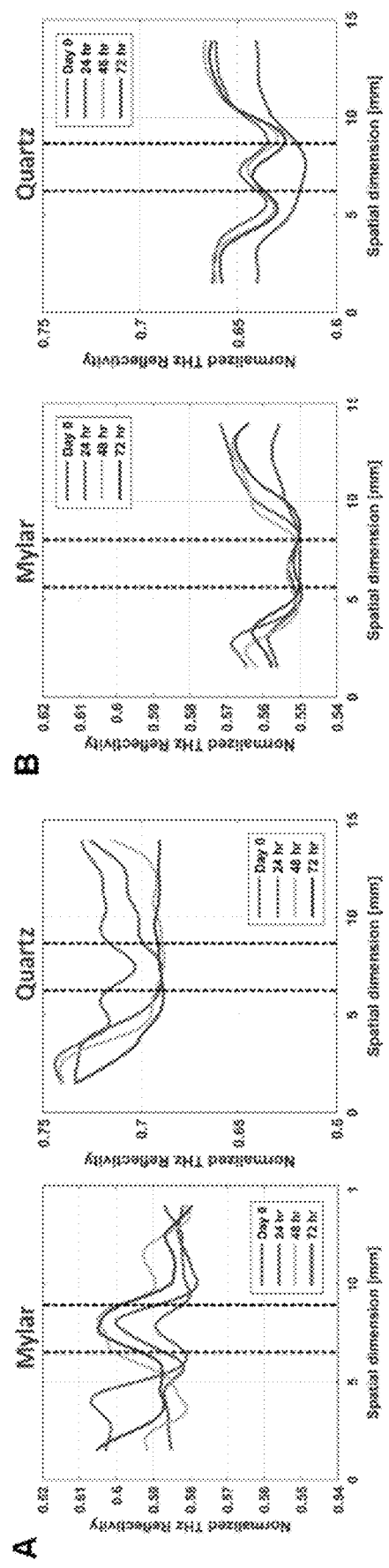
FIG. 31 provides data graphs of seventy-two hour normalized THz reflectivities of partial thickness and full thickness burn wounds under 12.7 μm Mylar window and 500 μm quartz crystalline window, generated in accordance with various embodiments.

Comparison of normalized reflectivity profiles that capture the burn contact area of partial thickness and full thickness wounds quantitatively reinforce findings observed by visual inspection of THz burn imagery acquired with both Mylar and quartz windows (FIG. 31). In FIG. 31, vertical dotted lines indicate the spatial location of the burn margins (determined by co-registering visible and THz imagery), the inner section corresponds to the burn contact area and regions to the left and right of the lines correspond to uninjured tissue. In accordance with various embodiments, THz reflectivity associated with the burn contact region of a partial thickness wound with respect to uninjured tissue results in increased THz reflectivity and decreased THz reflectivity when imaged with a Mylar and quartz window, respectively. This result is consistent over the 72 hr post-burn induction surveillance period and agrees with visual observations of THz burn contrast. In contrast, opposite THz reflectivity findings are true for a full thickness wound imaged with identical dielectric substrates over 72 hr following thermal insult. For example, reflectivity profiles of a full thickness wound imaged with quartz show a local peak THz reflectivity at the wound center, enveloped by two localized THz reflectivity minima. This finding corresponds to the previously mentioned central wound feature observed in time-series THz quartz imagery of full thickness wounds. These distinct THz signatures confer unprecedented conspicuity for burn wound severity.

Figure 32:
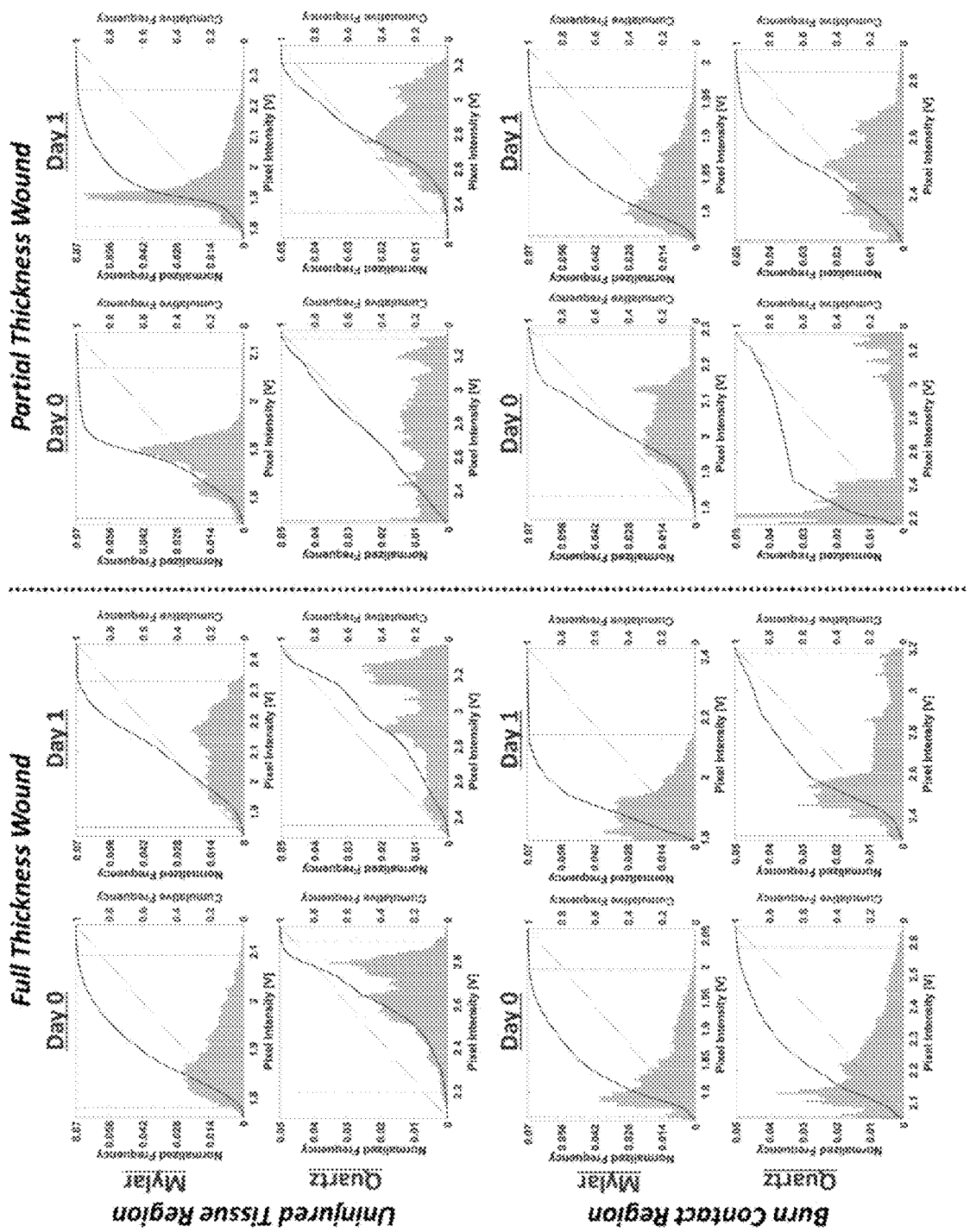
FIG. 32 provides temporal histogram of pixel intensities of Mylar and quartz THz imagery of uninjured skin, the contact area of a full thickness burn, and the contact area of a partial thickness burn, generated in accordance with various embodiments.
Figure 33:
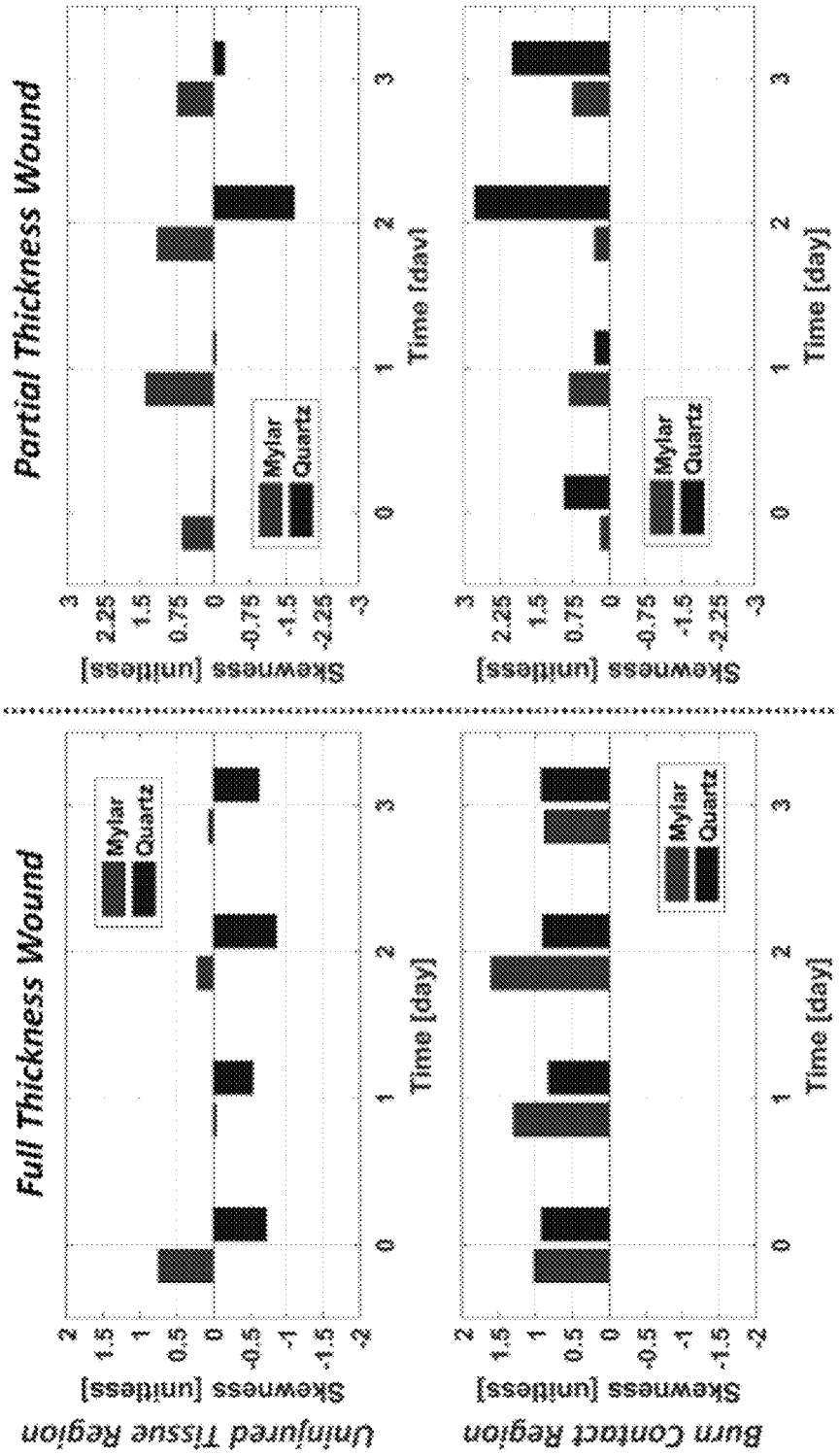
FIG. 33 provides a data graph demonstrating the skewness of Mylar and quartz histograms of uninjured skin, the contact area of a full thickness burn, and the contact area of a partial thickness burn, generated in accordance with various embodiments.

Pixel Intensity Distributions of THz Burn Imagery:

Histograms of pixel intensities of 72 hr Mylar and quartz images of uninjured skin surrounding a full thickness (Rat C) and partial thickness (Rat B) wound are displayed in FIG. 32. These subjects were identical to those used to compare 72 hr Mylar and quartz THz reflectivity profiles between a partial thickness and full thickness wound. For uninjured tissue in THz images of a full thickness wound, the Mylar histogram resembles that of a shifted Rayleigh distribution and demonstrates a stark bias towards darker pixels. Conversely, the quartz histogram for the same tissue region shows a heavy incidence of bright pixels and is somewhat multi-modal. From the plots, it is evident that the pixels of uninjured tissue in a full thickness wound obtained with the Mylar window are biased to the left and the pixels obtained with the quartz window are biased to the right. Histograms of pixel intensities are similarly biased to the left and right for uninjured skin surrounding a partial thickness burn imaged with Mylar and quartz, respectively. Histograms of pixel intensities associated with the burn contact area of each wound severity model are more complex. The burn contact area of a full thickness wound imaged with Mylar shows a higher incidence of dark pixel intensities compared to the same region imaged with Mylar in a partial thickness wound. In contrast, the contact area of a full thickness wound imaged with quartz shows a lower incidence of dark pixels compared to the same region imaged with quartz in a partial thickness wound. For all the acquired THz images of uninjured tissue, the Mylar pixels are always skewed positively (left) and the quartz pixels are always skewed negatively (right), in accordance with several embodiments (FIG. 33). It is also interesting to note that the time dependent variation in the skewness magnitude is correlated between the window types. The difference in skewness of each burn region (uninjured and burn contact area) between a partial thickness and full thickness burn imaged under each window is an indicator of perceivable differences in THz burn image contrast. Given that Day 0 is most clinically relevant for early burn wound assessment, the most important observations are the following: the skewness of the histograms of the uninjured tissue is greater between a full thickness and partial thickness burn imaged under quartz. In contrast, the skewness of the histograms of the burn contact area is greater between a full thickness and partial thickness burn imaged under Mylar.

Results described within this example demonstrate that it is possible to use reflective THz imaging, with the addition of window methodologies, to both track edema processes in vivo and distinguish burn wounds of varying severity based on TWC sensitivity to specific burn regions, in accordance with various embodiments. These THz imaging results are not only repeatable but are also consistent with known burn edema pathogenesis associated with partial thickness and full thickness burn wounds.

In many embodiments, marked differences in THz image contrast between partial thickness and full thickness wounds imaged under Mylar and quartz windows are evident immediately following injury and reflect THz-tissue interactions known to characterize thermal insult of tissue. Electromagnetic modeling of THz-tissue interactions predicts that the THz reflectivity of a tissue system imaged under Mylar at our center operating frequency (~525 GHz) increases approximately linearly with increasing TWC. In contrast, THz reflectivity of a tissue system imaged under quartz at the same operating frequency decreases with increasing TWC. Combining this information with what is known about burn edema pathogenesis, full thickness wounds imaged under both Mylar and quartz should experience changes in reflectivity that are consistent with an immediate, localized drop in TWC (i.e., transient cessation of vascular perfusion), followed by a gradual increase in TWC (i.e., edema), in accordance with multiple embodiments. In more embodiments, reflectivity changes associated with partial thickness wounds imaged with both dielectric windows should reflect immediate and greater TWC (i.e. pronounced arteriolar vasodilation).

Immediate THz reflectivity changes associated with both partial thickness and full thickness wounds imaged with Mylar and quartz windows on Day 0 are consistent with specific trends observed in burn edema pathogenesis. Irrespective of window selection, THz-based TWC variation in partial thickness wounds is greater than that of full thickness wounds. In many embodiments, compared to uninjured skin, lower THz reflectivity associated with the burn contact area of partial thickness wounds imaged under quartz corresponds to an increase in TWC at 7 hr. In more embodiments, higher THz reflectivity of the same region imaged under Mylar represents an increase in TWC at 7 hr. Full thickness wounds imaged with the same windows, in contrast, demonstrate smaller immediate changes in TWC compared to partial thickness injuries. These findings agree with well-established reports of peak edema being greater in partial thickness burns than in full thickness burns due to a marked decrease in dermal perfusion as burn depth increases. Although THz-TWC results observed in follow-up scans may differ among subjects in the same burn group, immediate TWC changes in the burn contact area are on par with each other.

Several embodiments are directed to the building of histograms utilizing the pixel intensities of THz images of wounds. Histograms of pixel intensities of the wound contact area and surrounding non-traumatized tissue in full thickness and partial thickness burns acquired with Mylar and quartz windows agree with trends observed in THz burn imaging contrast as well as edema pathogenesis. Intensity histograms of uninjured tissue regions acquired with a Mylar window for both wound severities are positively skewed, where this tissue region is associated with lower pixel intensities compared to the burn contact area. This corresponds to underexposed THz image contrast around the burn site that is visually apparent in all Mylar burn imagery. The degree of skewness, however, is greater for a partial thickness wound than a full thickness wound, and is consistent with the localized "bright band" characteristic of the burn site in partial thickness wounds. In several embodiments, this feature is predicted to correspond to greater edema in partial thickness wounds. In many more embodiments, intensity histograms of uninjured tissue under quartz are negatively skewed for both wound types, where the wound contact region appears lower in pixel intensity. This result is, again, consistent with reduced THz contrast in the burn contact area of quartz THz images and lower fluid shifts that are typically observed in wounds of this severity.

In many embodiments, Mylar is more sensitive to larger TWC changes while Quartz is more sensitive to smaller TWC changes at a center operating frequency of 0.525 THz. The burn contact area is known to experience larger fluid shifts than the surrounding, non-traumatized region. Mylar, in more embodiments; confers optimal TWC sensitivity to the burn contact area to distinguish both burn wound models. In several more embodiments, quartz is more sensitive to edema in the surrounding, uninjured tissue: the difference in skewness of the histograms of the uninjured tissue region is greater between partial thickness and full thickness burns under quartz than under Mylar. Dielectric window selection, therefore, causes the sensitivity of THz imaging to the TWC of burns to change based on the TWC range of the probed tissue region. THz images acquired with different dielectric windows vary not only in hydration sensitivity, but in information content, as the depth of tissue probed varies with the optical path length of the imaging system's window. The two sets of window images reveal different TWC maps in the burn contact and uninjured regions, suggestive that the quartz dielectric window successfully probed a different depth than the Mylar window.

Collectively, the use of multiple windows in accordance with multiple embodiments enables acquisition of unique and repeatable TWC maps of burn wounds. Because THz burn contrast associated with each window is both unique and consistent with known TWC trends in burn edema pathogenesis, various embodiments are directed to window-driven, high-speed THz imaging for the detection and monitoring of pathological conditions that lead to tissue edema.

Example 6: Non-Invasive THz Imaging of TWC for Flap Viability Assessment

Tissue "flaps" have become essential for the surgical reconstruction of patients with breast cancer, head and neck cancer, large soft tissue defects, and wounds (J. R. Payette, et al., *Plast. Reconstr. Surg.* 115:539-46, 2005; M. Bergkvist, et al., *Microvasc.* Res. 101:20-25, 2015; the disclosures of which are incorporated herein by reference). A flap includes the harvested skin, muscle, soft tissue or bone, and their corresponding neurovascular supply. This tissue is surgically resected and rotated or transferred from a donor site to a recipient site (L. Di Sieno, et al., *J. Biomed. Opt.* 21:025004-025004, 2016, the disclosure of which is incorporated herein by reference). Patency of the underlying arteries and veins is vital for flap survival. In cases of vascular occlusion (i.e., thrombosis), flap outcome directly correlates with the rapid restoration of the vessels' patency; if reduced viability can be identified before 6 hr of thrombosis onset, which typically occurs within 72 hr following surgery, 60-73% of compromised flaps may be salvaged (Q. Yang, et al., *Int. J. Oral Maxillofac. Surg.* 43:1059-63, 2014;

K. T. Chen, et al., *Plast. Reconstr. Surg.* 120:187-95, 2007; the disclosures of which are incorporated herein by reference).

Here, THz imaging of myocutaneous flaps in a pre-clinical rat model to explore the utility of THz-TWC based maps for early flap viability assessment. Six myocutaneous flaps of either high tissue viability (n=3) or low tissue viability (n=3) were surgically created in the dorsal skin of rats and an exemplary reflective THz imaging system was used to track the distribution of TWC across the flap margin over a period of 7 days. This time window was selected based on morphological changes observed in the field of view (FOV) and motivated by the evolution of the wound healing response following cutaneous injury. Rats were selected as our pre-clinical model given thicknesses of rat and human skin layers are most similar compared to those of other animal models. A survey of the literature also shows the rat model has proven useful for studying changes in skin subsequent to surgical elevation of a dorsal skin flap (M. G. Sowa, J. R. Payette, and H. H. Mantsch, *J. Surg. Res.* 86:62-69, 1999, the disclosure of which is incorporated herein by reference). A 2.5×2.5 $cm^2$ excised myocutaneous flap and a 2.5×2.5 $cm^2$ bipedicled myocutaneous flap were selected as a failure and survival model, respectively (R. M. McFarlane, et al., *Plast. Reconstr. Surg.* 35:177-82, 1965, the disclosure of which is incorporated herein by reference). Reflective THz measurements of skin were compared to temporally and spatially matched histology and clinical assessments.

Reflective THz Imaging System

A reflective THz imager, which measures 12 cm×10 cm×8 cm, was used to acquire TWC maps of myocutaneous flaps, in accordance with various embodiments. For this example, the exemplary THz system operates in reflection mode at a center frequency of 0.525 THz with ~125 GHz bandwidth. The effective center frequency and bandwidth of the system are constrained by the THz source's power spectral density and the detector's spectral responsivity. The photoconductive switch (PCS) based THz source is pumped by a 780 nm pulse train created by a frequency-doubled 1550 nm mode-locked laser with a 230 fs pulse width and 20 MHz repetition frequency. The resulting THz source beam is collimated by a 76.2 mm effective focal length (EFL), 25.4 mm clear aperture off-axis 90° parabolic (OAP) mirror. A 50.8 mm EFL OAP mirror at a 14° incidence angle is used to focus the beam onto the target. The reflected THz radiation is then collected and collimated by a second 50.8 mm EFL OAP. Finally, a 25.4 mm EFL OAP couples the collected signal to the feedhorn of a WR1.5 waveguide mounted Zero-bias Schottky diode detector (ZBSD). THz pulses are rectified by the ZBSD and then amplified with 38 dB of gain with a low-noise broadband amplifier. Resulting THz signals are coupled to a gated receiver driven with a reference pulse generated using a beam sampler, 1550-nm high-speed photodiode, and RF pulse amplifier. The THz imaging system acquires pixel-by-pixel data with a 1 ms integration time, and an image is generated by raster scanning the animal model beneath a fixed, focused THz beam using x and y stepper motors. An image with a 6 cm×6 cm FOV requires a scanning time of ~10 min using a 0.5 mm step size.

Tissue Flap Surgery

Figure 34:
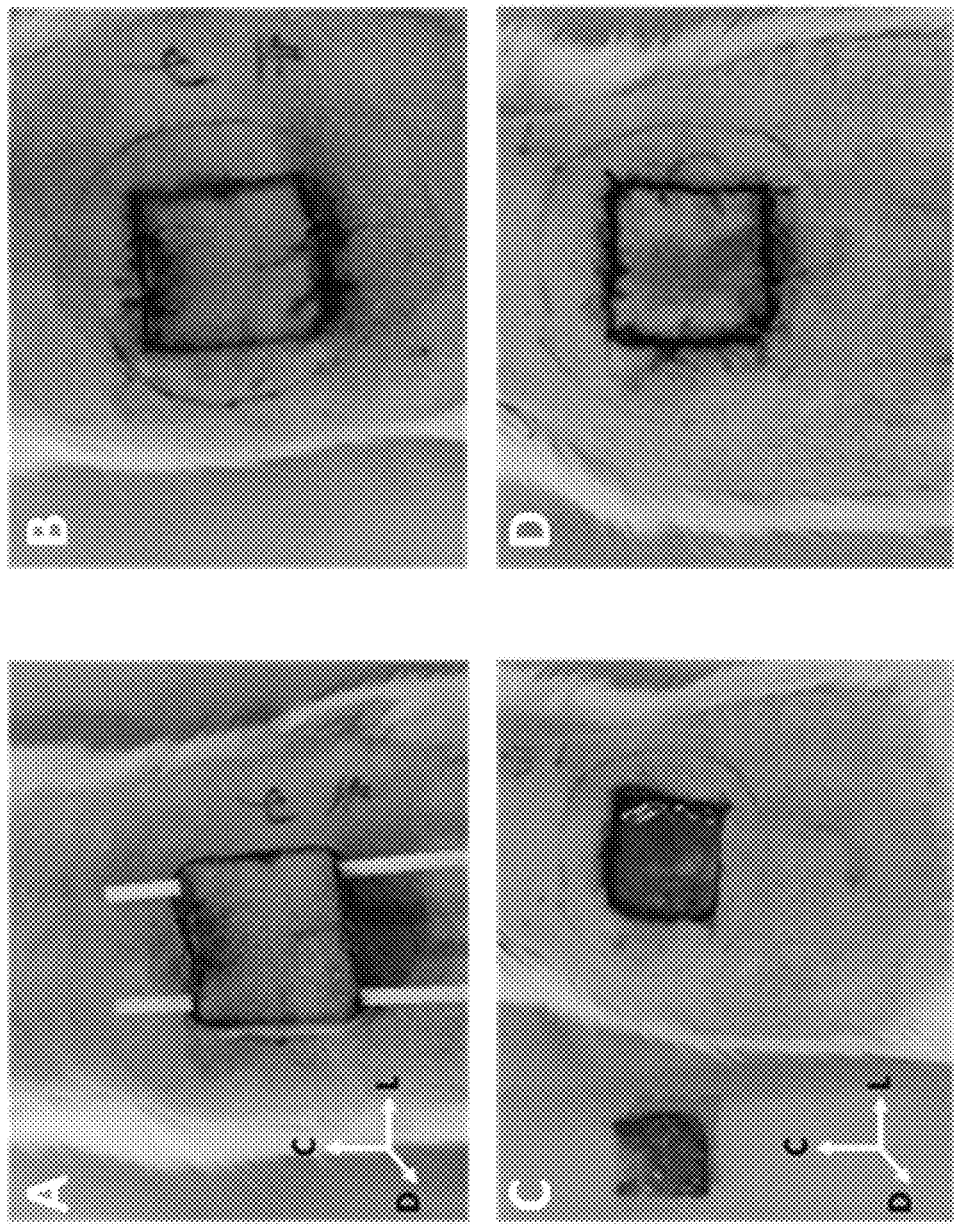
FIG. 34 provides photographs of myocutaneous flap design where (A) is an axially-based bipedicled flap (i.e., survival model) that is produced by incisions and then (B) surgically secured in its anatomical position and (C) is a completely excised myocutaneous skin flap (i.e., failure model) that is produced by incisions and then (D) sutured back in anatomic position; "L," "D," and "C" correspond to later, dorsal, cephalic anatomical direction of the rat.

All experiments were approved by the Institutional Animal Care and Use Committee (IACUC). Six 14 week old male Lewis rats (Charles River Laboratories, Wilmington, Mass.) weighing 250-300 g were used as pre-clinical models to investigate effects of varying flap tissue viability on TWC maps acquired with reflective THz imaging. Here, myocutaneous dorsal flaps of either low or high tissue viability, as shown in FIG. 34, were compared.

All rats were maintained in temperature-regulated environments (24° C.) on a 12-hr light/dark cycle and housed one pair per cage with soft bedding and a microinsolator cover. Animals underwent general anesthesia with inhaled isoflurane and were placed on a water heating pad for temperature regulation at 37±0.5° C. Each rat was shaved from scapula to pelvis to expose a 6×6 $cm^2$ area of dorsal skin. Rats were placed in prone position under the THz imaging system, a 12.7 μm dielectric Mylar window was lowered onto the shaved dorsal skin to flatten the imaging field, and pre-evaluation visible and THz images were captured with a SLR camera and the THz imager, respectively. The scanned area of the dorsum was marked with a black marker, and the anesthetized rat was then returned to the surgical field.

The rats were then aseptically prepared with three alternating scrubs of betadine and isopropanol and randomly assigned to receive either a 2.5×2.5 $cm^2$ excisional myocutaneous flap (n=3) or a bipedicled myocutaneous flap (n=3).

Shown in FIG. 34A, the axially based bipedicled myocutaneous flap was designed as the control for flap survival since all axially based vasculature and the dermal plexus to the flap remained intact through the bipedicled flaps. Using a #15 blade, an incision was made at the cephalic and caudal borders of the designed flap through the panniculus carnosus. The flap was elevated deep to the panniculus carnosus muscular layer to the lateral borders of the designed flap. Simple interrupted 5-0 polypropylene sutures were used to close the incision in anatomic position as shown in FIG. 34B.

As shown in FIG. 34C, the excisional myocutaneous flap was designed as an experimental flap failure since all vasculature was completely ligated when the flap was excised. Using a #15 blade, an incision was made along all borders of the designed flap though the panniculus carnosus. The flap was elevated deep to the panniculus carnosus muscular layer and the myocutaneous flap was completely excised. The flap was allowed to remain extracorporeal for 20 minutes. Again, simple interrupted 5-0 polypropylene sutures were used to close the incision in anatomic position as shown in FIG. 34D. Rats were then allowed to recover from anesthesia and transferred to the vivarium for post-operative monitoring. Post-operatively, all animals received analgesia with subcutaneous injections of carprofen (5 mg/kg) daily for 72 hr.

THz and visible imagery were continuously acquired for one hour after surgery, followed by a single 24 hr, 48 hr, and 7-day post-operative scan. At each time point, the dielectric Mylar window was lowered onto the flap during THz imaging. After a 7-day postoperative observation period, the rats were euthanized and histological specimens harvested.

Clinical Examination

Postoperative monitoring of flap compromise was performed by two head and neck physicians by visual inspection and palpation. Flaps were evaluated on a daily basis for the first 3 days and then finally on day 7 for clinical signs of ischemia and variation in tissue elasticity. On postoperative day 7, the total amount of skin flap necrosis was observed and recorded for each rat.

Histology Design

Figure 35:
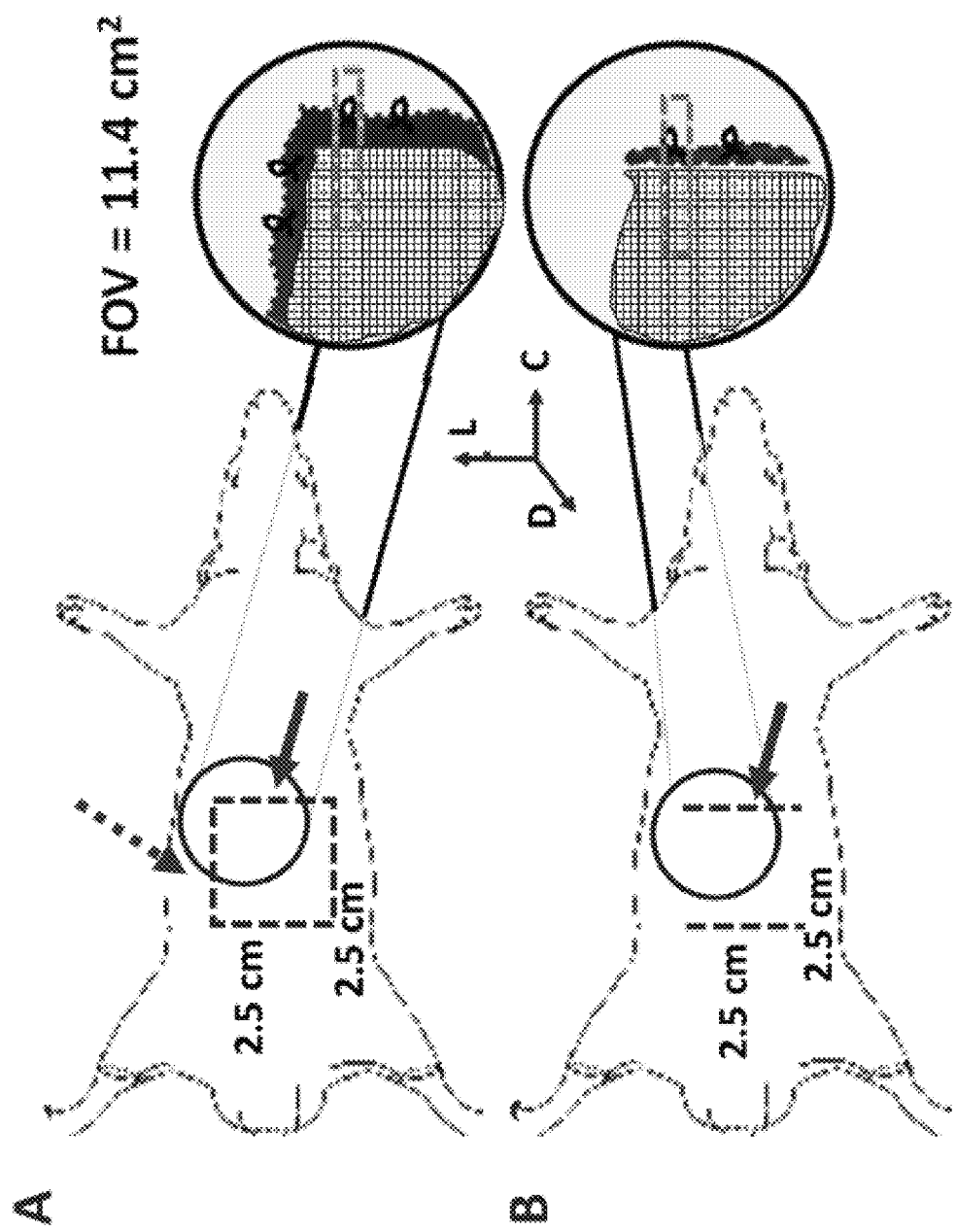
FIG. 35 provides a schematic detailing the histological design for evaluation of tissue viability for (top) an excised flap and (bottom) a bipedicled flap imaged under a Mylar window in accordance with various embodiments.

FIG. 35 shows the design used for histological evaluation of both flap viability models. A blind histological analysis of flap tissue harvested at 7 days post operation was compared to visible and THz imagery to determine tissue viability in tissue flaps, in accordance with multiple embodiments. A 2 mm×2 cm region (dotted green rectangle in FIG. 35) was harvested from the cephalic incision sites of each flap, transferred to 10% formalin solution, and submitted for routine processing for histopathological evaluation.

All tissue samples were histologically sectioned sagittal to the major axis of the sample and contained an intradermal suture for orientation and registration of the tissue specimen. Three histological slices of 5 μm thickness were acquired from each tissue block, stained with hematoxylin and eosin, and analyzed to determine tissue necrosis. Histologic sections included the original flap (i.e., red hatched region under the window in FIG. 35) as well as a myocutaneous margin or non-traumatized tissue (i.e., tan region under the window in FIG. 35) to provide a control area for histologic comparison. Assessment of viability was based on the morphology of the individual cells and patency of vessels (P. N. Manson, et al., "*Ann. Surg.* 198:87-90, 1983, the disclosure of which is incorporated herein by reference). Histological outcome of tissue flaps was compared to visible images, and visible images were compared to their companion THz images. Using this methodology, THz observations were related to histologically verified images of tissue flap viability.

Statistical Analysis:

An independent Student t-test was used to compare pixel-by-pixel reflectivity differences between pre-surgery and 24 hr post-surgery THz images along linear contours for excised flaps and bipedicled flaps. Equal variances were assumed for both flap models and the level of significance was set at $p<0.05$.

Results

Figure 36:
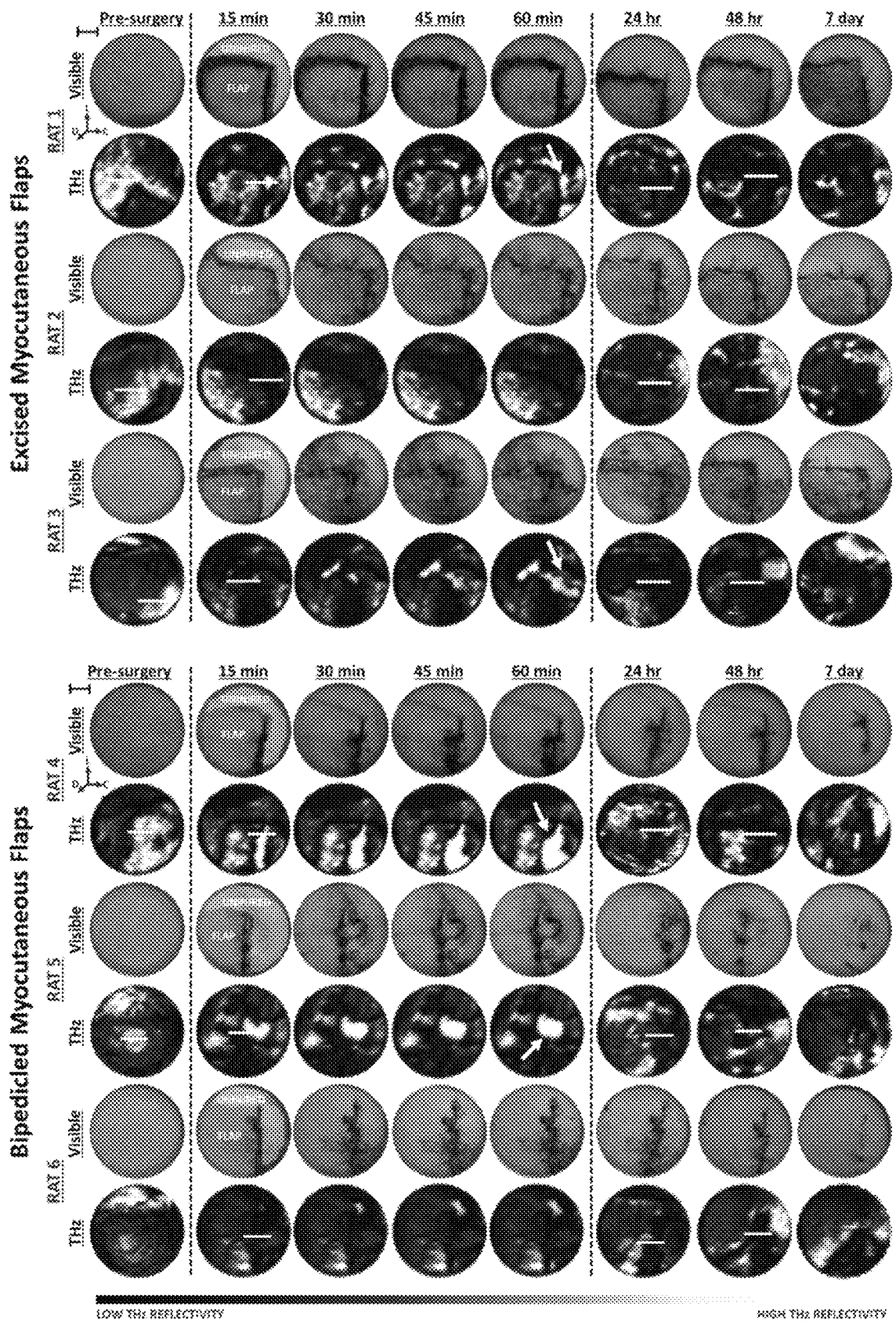
FIG. 36 provides a time-series of in vivo visible and THz imagery of excised myocutaneous flaps and bipedicled myocutaneous flaps imaged under a thin Mylar window over a seven day period, generated in accordance with various embodiments.

In vivo THz flap imaging: FIG. 36 shows in vivo THz time-series imagery of three excised flaps and three bipedicled flaps in the dorsal skin of anesthetized rats was acquired over a 7-day period, generated in accordance of various embodiments. Skin flaps were imaged under a thin (12 μm) film Mylar window to eliminate confounding effects from non-uniform surface topography, and visible and parallel THz images were generated. Because the dimension of the flaps exceeded that of the dielectric window, only the cephalic incision and flap tissue were captured in THz and visible images. The flap tissue and non-injured area are denoted by grey and yellow fields in visible images at 15 min post-surgery, respectively. The "hot" color map associated with THz imagery transforms black to the global minimum THz reflectivity and white to the global maximum THz reflectivity.

During the first 48 hr following surgery, THz reflectivity profiles were generated for 1.5 cm long contours (indicated by white horizontal line segments in THz imagery in FIG. 36) that captured the same region of the cephalic flap margin, in accordance of many embodiments. Clinical acute assessments of flap viability are typically performed for 48 hours post-operatively, and therefore we used this as our acute endpoint for the THz image analysis. In accordance with multiple embodiments, THz reflectivity values of these contours were normalized to the maximum THz reflectivity acquired from an aluminum calibration target (i.e., ideal reflector) and zero THz reflectivity measured in the absence of a reflecting target (i.e., air). Next, the percent change (% Δ) in THz reflectivity was plotted in FIG. 37, which represents the pixel-by-pixel % reflectivity difference between the different post-surgery THz images (15 min, 24 hr, and 48 hr) and the pre-operative THz image along the white line contour shown in FIG. 36. These reflectivity plots, generated in accordance with various embodiments, are referred to as "THz profiles." Lengths of the THz profile to the left and right of the cephalic incision site, that is denoted by a dotted vertical line, correspond to the flap region and surrounding non-traumatized tissue, respectively.

As shown in FIG. 36, THz images of the rat dorsums prior to flap surgery displayed mostly uniform reflectivity across the FOV. Low reflecting areas, such as those evident in the periphery of many flaps, may have resulted from reduced contact coupling between the Mylar window and underlying skin. Specifically, the curvature of the spine in the dorsal skin of these animal models is hypothesized to have contributed to this effect.

Figure 37:
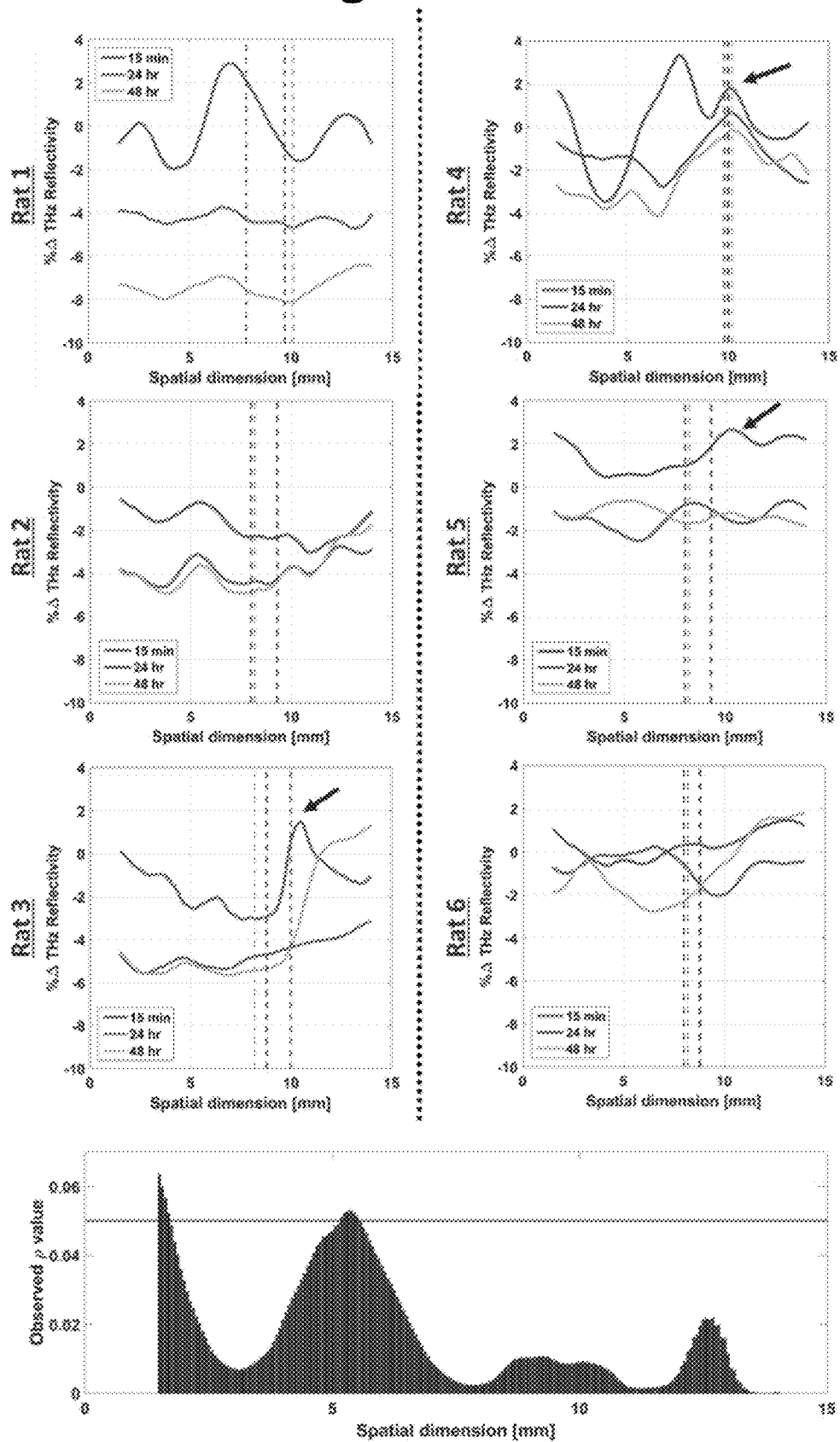
FIG. 37 provides spatial THz reflectivity profiles for THz flap image sets, generated in accordance with various embodiments.

Even with this imaging confounder, and in accordance with multiple embodiments, THz images for all flaps identified the spatial location of the surgical incisions and flap tissue immediately following surgery. As shown in FIG. 36, for THz images of all excised flaps at 15 min-1 hr, the flap tissue is characterized by high reflectivity, bordered by a region of low reflectivity (i.e., the cephalic and lateral incision sites), and finally surrounded by region of high reflectivity (i.e., uninjured tissue). This result is most apparent in rat 2, for which little to no blood leakage was observed at the incision site. In more embodiments, for the bipedicled flap group (see FIG. 36), THz imaging affords the spatial localization of the single cephalic incision. For THz images of most subjects in this group, the incision site appears as a line of low reflectivity bordered by a region of higher reflectivity (i.e. the flap and non-injured tissue). This result is most obvious in rat 6, for which little to no blood leakage was observed at the incision site. Because a bipedicled flap does not include lateral incisions, black lines apparent in THz imagery of this tissue region in FIG. 36 were likely due to either intrinsic surface contours within the rat dorsum or dissection borders deep to the panniculus layer rather than gross features from the bipedicled flap. For rat 1, rat 3, rat 4, and rat 5, the leakage of blood (denoted by solid white arrows) from the incision sites further delineated their respective flap margins; blood, like TWC, is a highly reflective, dispersive polar medium, and therefore a confounder to THz TWC contrast. FIG. 36 shows the accumulation of blood along the flap margin appears as increased THz reflectivity in all post-op images acquired between 15 min and 60 min. Even with the presence of blood, in accordance with several embodiments, the overall reflectivity of the flap region is different between both flap viability groups. Because THz flap imagery acquired 15 min postoperatively was least confounded by blood, THz reflectivity at this time point was analyzed for Day 0. THz reflectivity profiles for the aforementioned rats at the 15 min mark in FIG. 37 illustrate these irregularities, or "hot spots," along the length of the cephalic incision as clearly defined peaks denoted by solid red arrows. With the exception of these peaks and 'troughs' in the reflectivity plots, likely due to uncoupling between the window and skin and the presence of blood, % Δ THz reflectivity between pre-surgery and 15 min post-surgery across the flap for most rats is close to 0%.

Twenty-four hours postoperatively, several embodiments are directed to the contrast of THz images and their accompanying reflectivity profiles which became markedly distinct between both flap models. Visible inspection alone of the THz excised flap imagery in FIG. 36 suggested reduced THz reflectivity in the form of 'dark zones' at the cephalic and lateral incision site as well as the peripheral segment of the flap. Though reflectivity of the cephalic incision was similarly low in THz imagery of bipedicled flaps, likely due to then dried blood, the surrounding tissue contrast was mostly unperturbed. This result was further substantiated by % Δ THz reflectivity profiles for both flap models at 24 hr in FIG.

37. A noticeable decline in THz reflectivity (Rat 1: −4% Δ; Rat 2: −4.5% Δ; Rat3: −5.5% Δ) was apparent in excised flaps (i.e., left of the dotted vertical lines in FIG. 37 which continued to persist by 48 hr ensuing surgery in rat 2 and rat 3. Because of the aforementioned coupling issues between the window and underling tissue for rat 1, the drop in reflectivity is more pronounced at 48 hr. The tissue flap texture and topography also drastically change by 7 days postoperatively in this flap failure model. These factors, therefore, begin to slightly confound contrast observed in THz images of all excised flaps at this time point. Because clinical acute assessments of flap viability are typically performed for 48 hours post-operatively, unusual THz contrast observed at 7 days post-surgery in excised flaps is clinically irrelevant, and therefore can be ignored. In many embodiments, % Δ THz reflectivity of non-traumatized tissue adjacent to all excised flaps (i.e., right of the dotted vertical line in FIG. 37 approached baseline values (0%). This result is particularly evident in both rats 2 and 3. By comparison, most % Δ THz reflectivity for both the flap region and adjacent non-traumatized tissue in bipedicled flaps either remained within the same reflectivity neighborhood or approached that at pre-surgery (0%) at 24 hr following surgery. This result is particularly apparent in THz reflectivity plots for rat 5 and rat 6, neither of which dip below ~2% Δ in reflectivity. This behavior persists at 48 hr and 7 days post-surgery, as there are no gross topographical changes expected in a tissue survival model. Irregularities in THz contrast, such as reduced % Δ THz reflectivity in the form of troughs for plots at 48 hr for rat 4 and rat 6, were likely explained by suboptimal coupling of tissue flaps with the dielectric window, irregular incision geometries, as well as differences in perfusion due to non-uniform flap surgery.

Because 24 hr post-surgery is clinically more important for flap assessment, an independent Student t-test was performed to assess differences in reflectivity between a flap failure model and flap survival model at this time point (see FIG. 37 (bottom panel). Such an analysis has important clinical implications, as gross changes in tissue flap viability are typically visually apparent 48 hr following surgery. In FIG. 37 (bottom panel), the y-axis describes the significance value (rho) of an independent t-test performed between the % Δ THz reflectivity profiles of all bipedicled flaps (n=3) and excised flaps (n=3) at 24 hr post-surgery. As previously explained, % Δ THz reflectivity profiles at 24 hr represent the pixel-by-pixel reflectivity difference between the pre-operative image and post-surgery image at 24 hr along the white line contour. The x-axis in FIG. 37 (bottom panel) represents the spatial dimension of this contour. Differences in THz reflectivity at 24 hr post-surgery between both flap viability models are statistically significant (i.e. p<0.05, denoted by the horizontal red line) along the entire length of the contour. Moreover, in accordance of many embodiments, this statistically significant variation in THz reflectivity between a flap survival and flap failure model is observed 24 hr prior to gross changes in tissue viability using clinical inspection alone.

Figure 38:
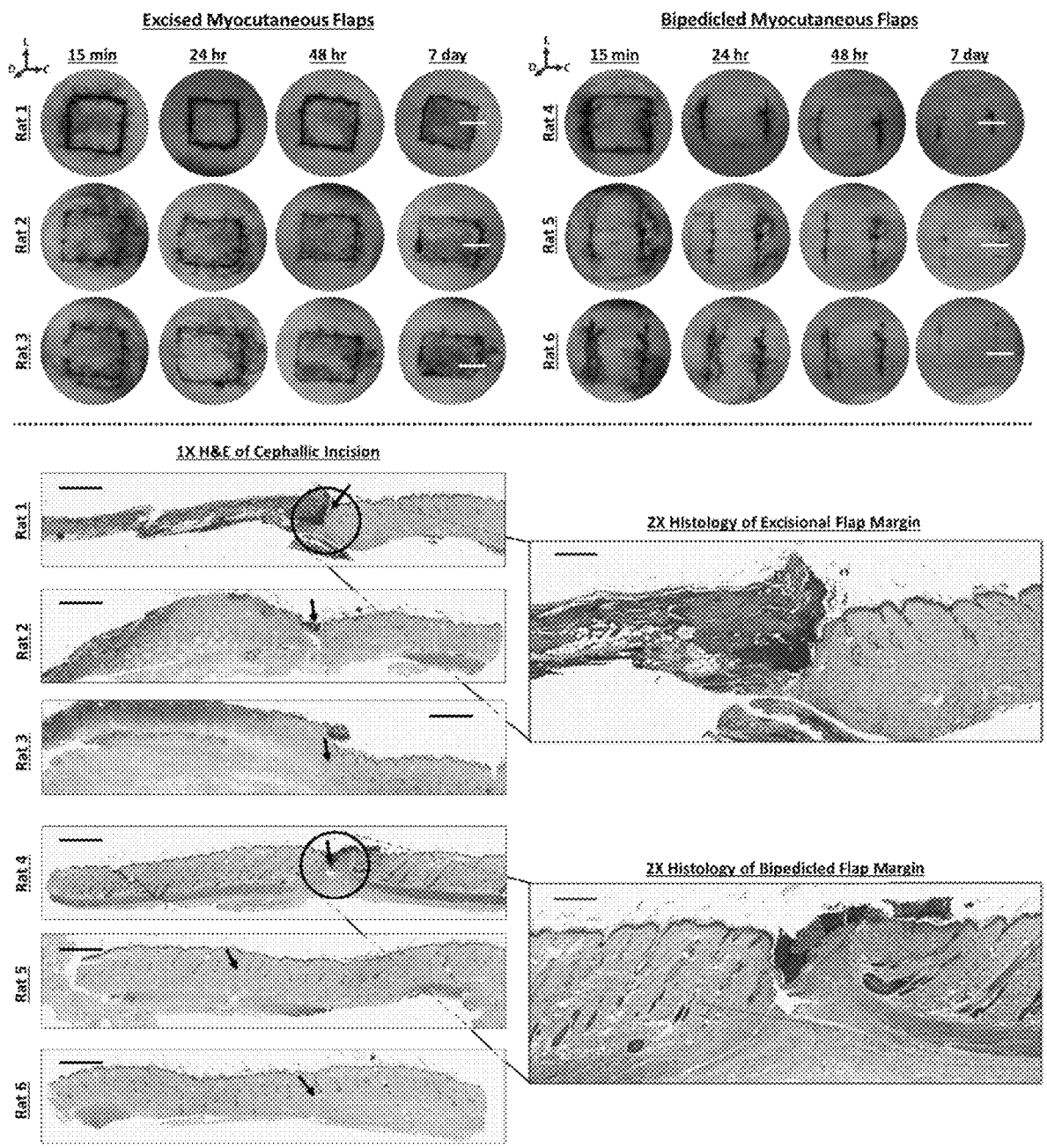
FIG. 38 provides clinical and histological assessment of excised and bipedicled flap viability.

Gross Examination:

Surviving surface areas in each flap viability model were markedly different as shown in FIG. 38. Clinical evaluation of bipedicled flap tissue revealed no signs of ischemia (i.e., cyanosis) and minimal change in skin pliability, all indicative of a surviving flap. Contraction of the cephalic and caudal incisions by Day 7 suggested optimal wound healing likely due to neovascularization and metabolic support from the lateral pedicles. The survival area was estimated to be 100% by two independent observers (JKA and RJ). Conversely, the excised flaps displayed progressive necrosis over 7 days. At 24 hr, the flaps appeared grossly absent of congestion or cyanosis, with no clear demarcation being evident between viable and nonviable tissue. By 48 hr, tissue contraction and cyanosis began to appear near the peripheral segments and on examination accounted for 30%, 40%, and 25% of the flap area in rat 1, rat 2, and rat 3, respectively. This necrosis continued, and by Day 7, a well-defined demarcation line between viable and nonviable tissue was evident. The surviving surface area of the myofascial flap was estimated to be ~0%, 10%, and 20% for rat 1, rat 2, and rat 3, respectively.

Histological Assessment:

Histological verification of tissue viability of both bipedicled and excised flaps was necessary; although a 2.5 cm×2.5 cm bipedicled flap and excised flap were hypothesized to result in a survival and failure model, respectively, there is no confirmation of this result in the literature. FIG. 38 shows histological evaluation of tissue sections from both flap models confirmed viability results that were evident grossly at 7 days following surgery. A blinded pathologist identified all histological sections from cephalic incisions of the excisional flaps as necrotic. Severe, full thickness necrosis of the skin and underlying muscle layers as well as the loss of dermal papilla and sebaceous glands were captured by hypereosinophilia in hematoxylin and eosin (H&E) stained sections, delineating a clear demarcation between the non-traumatized viable tissue. Neovascularization and early collagen deposition were only compromised and apparent in the adjacent, non-injured tissue.

In contrast, caudal and cephalic segments of bipedicled flaps were all completely viable (~0% necrosis) on histological evaluation (see FIG. 38). Both non-injured and flap segments were characterized by intact skin and muscle layers, subcutaneous follicles, and glands. While absent in the samples of the excised flaps, early signs of wound healing, specifically granulation tissue and chronic inflammation, were apparent at the incision margin (denoted by black arrow).

In accordance with numerous embodiments, in vivo THz imaging measurements indicate that TWC of an excised flap and bipedicled flap model, determined to have low and high tissue viability, respectively, is markedly different. Moreover, various embodiments are also directed to the variation in TWC between both flap models is evident as early as 24 hr post-operatively. Following surgical elevation of excised flaps, THz TWC contrast at the cephalic incision site is significantly lower than that of the pre-elevation value. TWC contrast observed in THz imagery at this site continues to progressively decline for the remainder of the 7-day observation period.

Spatiotemporal variations in TWC contrast in THz imagery of the excisional flap model are consistent with both clinical and histological assessments of flap viability. As shown in FIG. 38, there are few visual signs of desiccation or abnormalities (i.e., edema) observed within excised flap tissue 24 hr after the surgical procedure has been completed. Difficulty in visual assessment of edema arises because fluid build-up, that is perceived clinically as an increase in tissue volume, is only visually apparent after tissue volume has doubled. At this same time point, however, the TWC THz map has clearly identified those regions of tissue that were insufficiently hydrated. Since adequate perfusion of the dermal plexus is essential to sustain the functional and structural viability of the skin, it is expected that severely dehydrated tissues will gradually proceed to ischemia, and finally necrose. This progression is grossly observed 48 hr after surgery as well as confirmed histologically on Day 7 in FIG. 38; skin flaps rely on the underlying vascularity of the bed for adequate TWC and nutrients, and therefore wounds that are poorly vascularized, as in the case of an excised injury, will not support the flap. Accordingly, embodiments are directed to the post-surgical diagnosis of flap assessment, wherein a lack TWC suggests insufficient hydration and gradual procession to necrosis.

Conversely, THz TWC contrast across a bipedicled flap remains similar to that at pre-surgery as shown in FIG. 37. This TWC result is likely due to survival mechanisms characteristic to flaps containing pedicles, or an intact blood supply. Clinical and histological evaluation of tissue viability of the bipedicled flaps support this finding. Collectively, THz visualization of differences in flap TWC enables detection of flap status 24 hr prior to clinical assessment in accordance with several embodiments. Specifically, in clinical cases when a pre-evaluation THz scan of TWC is typically unavailable, early detection of TWC changes with respect to the neighboring uninjured tissue could enable expedited surgical re-exploration and potential salvage of failing tissue flaps prior to irreversible ischemia.

Example 7: Predictive Machine-Learning Framework

Figure 39A:
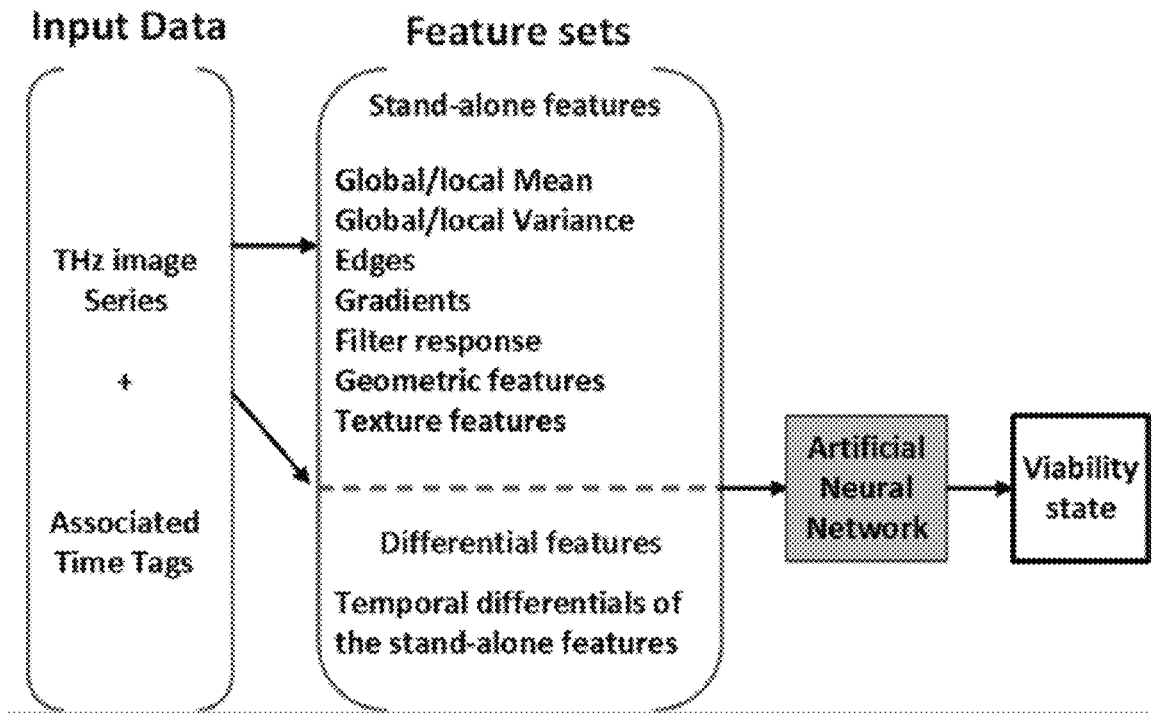
FIGS. 39A and 39B provide schematics for multidimensional longitudinal THz feature based viability prediction in accordance with embodiments, wherein the network structure: (A) consists of a layer of input nodes through which the multi-dimensional MRI-based and auxiliary features are presented (multiple hidden layers that provide a nonlinear mapping and a layer of output nodes, which delivers the outcome of the analysis), and (B) individual node.
Figure 39B:
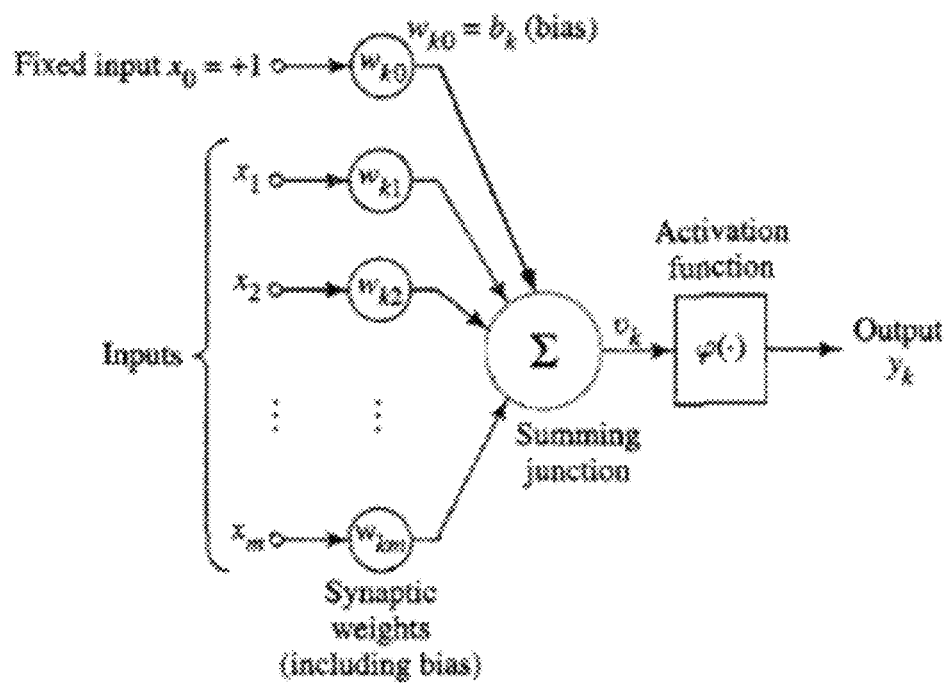

In many embodiments important prognostic features may be identified from THz imagery and utilized to infer/predict viability at various time points in a machine-learning framework. In particular, in many embodiments a hierarchical feature structure (technically known as sparse encoder or sparse version of Hinton's deep belief nets may be utilized. (See, G. E. Hinton, S. Osindero, and Y.-W. Teh, *Neural Computation*, vol. 18, pp. 1527-1554, 2006 Jul. 1 2006, the disclosure of which is incorporated herein by reference.) As conceptualized in Figures FIG. 39, in many embodiments a superset of features derived from longitudinal THz image may be used to train and validate the hierarchical network. Upon estimating the parameters (weights), the parameterized belief net will provide an inference tool that will predict the viability from imaging data. As a special characteristic of the sparse autoencoder structure, the learning process penalizes the number of features contributing significantly to the inference relationship, so that salient features will be automatically discovered. These extracted features will elucidate the most relevant THz derived burn indicator(s).

In many embodiments model function and development process, and specifically the method for determining the network weights. The weight determination process in accordance with embodiments may be considered a supervised learning problem where there is access to training input-output (x, y) examples. Here, the inputs will be extracted features from longitudinal THz imaging (FIG. 39A) and the output will be categorical variability states (though formulated as a binary classification in this proposal, it can be extended to multiple classes to incorporate more general staging/scoring schemes) quantified by histopathology results at the designated time points. The network is used for defining a complex, nonlinear form of hypotheses that $y=h_{w,b}(x)$ with parameters W,b that are fit to the data. For better efficiency and robustness of the learning, the same features may be used as input, and only regression weights (thus the corresponding regression function) may change depending on the time point, the pathology test that was performed, and the viability state acquired. For conciseness, the following description of the network structure has been generalized. The actual network structure will be customized according to the logic in (FIG. 39A) in accordance with embodiments.

Deep learning network structure and parameter estimation: Each node (FIG. 39B) takes $\{x_i\}_{i=1}^{m}$ input (and a +1 term for intercept), and output $y_k = h_{w,b}(x) = \varnothing(W^T x) = \varnothing(\Sigma_{i=1}^{m} W_{ki} x_i + b_k)$, where $\varnothing \mathfrak{R} \rightarrow \mathfrak{R}$ is an activation function that is usually chosen to be the sigmoid function $\varnothing(z) = (1+e^{-z})^{-1}$ to introduce nonlinearity into the regression. A belief network puts together many simple nodes to build a network that maps the input to the nodes on the leftmost layer, known as the input layer, to the output of the nodes on the rightmost layer, the output layer. The process of training the network will be to estimate the parameters (W,b) using a set of known samples by minimizing a cost function. For a specific sample (x, y), the mis-fitting cost function may be based on the squared error (Eq. 22).

$$J_{fit}(W,b;x,y) = \|h_{W,b}(x) - b\|^2 \qquad \text{EQ. 22}$$

Within the network, regularization on the weights W, which will decrease the magnitude of the weights to prevent over-fitting. The regularization (EQ. 23 where l indexes the layer and j and i index the input and output nodes, respectively) may be designed with compressive sensing principle to encourage sparsity in the weights.

$$J_{reg}(W) = \Sigma_l \Sigma_i \Sigma_j |W_{ji}^l| \qquad \text{EQ. 23}$$

This has the effect of automatic features selection since only the features with non-trivial (non-zero) weights actually contribute to the regression. The overall objective is written in EQ. 24.

$$J(W,b) = \Sigma_{i=1}^{M} J_{fit}(w,b;x^j,y^j) + \lambda J_{reg}(W) \qquad \text{EQ. 24}$$

The conjugate gradient descent method may be used to minimize the cost function and determine the parameters W, b, with the partial derivatives computed by back-propagation Uncertainty Quantification, and Validation:

The outcome regression uncertainty will indicate the tradeoff between overall model accuracy and precision. The uncertainty estimate may be obtained by evaluating the per-sample mis-fitting (EQ. 22). The discrepancy between learnt network output and the training samples will be obtained by summing across the training cohort (first term in EQ. 24). As in any regression work, the k-fold cross validation will be performed to reduce model mis-fitting. Based on the planned cohort, a 10-fold cross-validation is planned. The error from the validation process will provide a second uncertainty estimate. The two uncertainty estimates will be used to validate the network structure. When network structures are properly chosen (e.g., in the absence of over-fitting), the two uncertainty measures are expected to agree.

From the resulting classifiers, a rank list will be developed based on the sensitivity and specificity values of each classifier as a function of time up to 3 days post-burn, such that the highest ranked classifiers will offer the greatest sensitivity and specificity at the earliest time points. The earliest time point yielding an effective classifier will be identified as early as a few hours.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method for THz imaging of the total water content of a wound, comprising:
   generating an illumination beam having a frequency that is variable about at least one central wavelength greater than 100 GHz;
   illuminating a wound area with the illumination beam, wherein the frequency produces a plurality of reflected signals from the wound area, and wherein the wound area comprises a cutaneous injury and surrounding tissue, wherein the surrounding tissue is adjacent to the cutaneous injury and defined by a fluctuation of water content;
   detecting the plurality of reflected signals at a first timepoint;
   combining the plurality of reflected signals to obtain a first reflectivity map of the wound area, said first reflectivity map having a combined signal variation indicative of at least the spatially resolved tissue water content of the wound area; and
   assessing severity of the cutaneous injury by characterizing the plurality of reflected signals from the cutaneous injury and by characterizing the plurality of reflected signals from the adjacent surrounding tissue.

2. The method of claim 1, wherein the illumination beam is one of either pulsed or continuous wave.

3. The method of claim 1, wherein the first reflectivity map is further correlated with a separately obtained spatially imaging data selected from the group consisting of visible light imagery and magnetic resonance imaging.

4. The method of claim 1, wherein the type of cutaneous injury is a surgical flap, wherein the first reflectivity map elucidates the nature of the tissue water content gradient of the cutaneous injury and the adjacent surrounding tissue, and wherein the tissue water content gradient of the cutaneous injury and the tissue water content gradient of the adjacent surrounding tissue are each used to assess a viability of the surgical flap.

5. The method of claim 1, wherein the severity of the cutaneous injury is characterized by a classifier trained on wound physiology features.

6. The method of claim 1 further comprising:
   temporally detecting the variation of the plurality of reflected signals such that a change of reflected signals in the cutaneous injury and the surrounding tissue are detected over two or more time points, wherein the two or more time points comprise the first timepoint;
   obtaining the first reflectivity map for the first timepoint and at least a second reflectivity map for each of the two or more time points, each said reflectivity map having a combined signal variation indicative of at least the spatially resolved tissue water content of the wound area; and
   assessing the severity of the cutaneous injury by characterizing a temporal change of plurality of the reflected signals from the cutaneous injury with respect to the adjacent surrounding tissue over the two or more time points.

7. The method of claim 1, wherein the frequency may be varied between 100 GHz and 1 THz.

8. The method of claim 7, wherein the frequency is between 400 and 700 GHz.

9. The method of claim 1, further comprising
   imaging the wound area with a visible light camera to obtain a visible light image; and
   superimposing the first reflectivity map onto the visible light image.

10. The method of claim 9, further comprising marking the wound area with a fiducial marker capable of enhancing alignment of the visible light image and the superimposed first reflectivity map.

11. The method of claim 1, wherein the illumination beam is passed through at least one dielectric window prior illuminating the wound area.

12. The method of claim 11, wherein the dielectric window is comprised of at least one material that is selected from the group consisting of Mylar and quartz.

13. The method of claim 1, further comprising:
    contemporaneously imaging a reflector to obtain a maximum THz reflectivity; and
    normalizing the first reflectivity map to the maximum THz reflectivity.

14. The method of claim 13, wherein the reflector is an aluminum calibration target.

15. The method of claim 1, wherein the cutaneous injury is a burn, wherein the first reflectivity map elucidates the nature of the tissue water content gradient of the cutaneous injury and the adjacent surrounding tissue, and wherein the tissue water content gradient of the cutaneous injury and the tissue water content gradient of the adjacent surrounding tissue are each used to assess the depth of the burn.

16. The method of claim 15, wherein detection a low level of desiccation in the adjacent surrounding tissue indicates a partial thickness burn; and an overall increase of tissue water content in the adjacent surrounding tissue indicates a full thickness burn.

17. The method of claim 15, wherein the assessment of the depth of the burn and the tissue water content gradient is used to medically assess tissue viability within the wound area.

18. A THz tissue water content imaging apparatus comprising:
    an emission source configured to generate an illumination beam having a frequency that is variable about at least one central wavelength greater than 100 GHz;
    a detector configured to receive and record a THz signal;
    one or more transmission optics disposed in optical alignment between the emission source and a target wound area, and configured such that the transmission optics directs the illumination beam to impinge upon a target area on the surface of the wound area, and gathers a reflected THz signal from the target wound area and transmits the reflected THz signal to the detector, wherein the wound area comprises a cutaneous injury and surrounding tissue, wherein the surrounding tissue is adjacent to the cutaneous injury and defined by a fluctuation of water content; and
    an analyzer for using a plurality of reflected THz signals obtained of at least one illumination beam frequency to produce a reflectivity map of the wound area, said reflectivity map having a combined signal variation indicative of at least the spatially resolved tissue water content of the wound area, wherein the analyzer performs the following steps:
        combine the plurality of reflected THZ signals to obtain the reflectivity map of the wound area; and assess severity of the cutaneous injury by characterizing the plurality of reflected signals from the cutaneous injury and by characterizing the plurality of reflected signals from the adjacent surrounding tissue.

19. The apparatus of claim 18, where in the one or more transmission optics utilize compact reflective geometries.

20. The apparatus of claim 18 further comprising a visible light camera configured to obtain a visible light image of the wound area.

21. The method of claim 18, wherein the reflectivity map is further correlated with a separately obtained spatially imaging data selected from the group consisting of visible light imagery and magnetic resonance imaging.

22. The apparatus of claim 18, wherein the transmission optics at least comprise at least two 90° off-axis parabolic mirrors arranged such that the clear apertures of the parabolic mirrors are parallel and such that their focal spots overlap.

23. The apparatus of claim 18, wherein the illumination beam is collimated.

24. The apparatus of claim 18, wherein the illumination beam is one of either pulsed or continuous wave.

25. The apparatus of claim 18, wherein the analyzer utilizes a classifier trained on wound physiology features to assess the severity of the cutaneous injury.

26. The apparatus of claim 18, wherein the cutaneous injury is a burn, wherein the reflectivity map elucidates the nature of the tissue water content gradient of the cutaneous injury and the adjacent surrounding tissue, and wherein the tissue water content gradient of the cutaneous injury and the tissue water content gradient of the adjacent surrounding tissue are each used by the analyzer to assess the depth of the burn.

27. The apparatus of claim 18, wherein the apparatus is capable of producing the reflectivity map of the wound area in under ten minutes.

28. The apparatus of claim 27, wherein the frequency may be varied between 100 GHz and 1 THz.

29. The apparatus of claim 18, wherein at least one dielectric window is provided atop the wound area and is configured such that the illumination beam passes therethrough in illuminating the wound area.

30. The apparatus of claim 29, wherein the at least one dielectric window is comprised of material that is selected from the group consisting of Mylar and quartz.

31. The apparatus of claim 29, wherein a reflector exists within the at least one dielectric window to provide maximal reflectivity.

32. The apparatus of claim 31, wherein the reflector is an aluminum calibration target.

* * * * *